(12) United States Patent
Nii et al.

(10) Patent No.: US 10,396,299 B2
(45) Date of Patent: *Aug. 27, 2019

(54) ORGANIC ELECTROLUMINESCENT DEVICES AND METAL COMPLEX COMPOUNDS

(71) Applicant: UDC IRELAND LIMITED, Dublin (IE)

(72) Inventors: Kazumi Nii, Kanagawa-ken (JP); Kousuke Watanabe, Kanagawa-ken (JP); Tatsuya Igarashi, Kanagawa-ken (JP); Seiji Ichijima, Kanagawa-ken (JP); Toshihiro Ise, Kanagawa-ken (JP)

(73) Assignee: UDC IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/825,566

(22) Filed: Nov. 29, 2017

(65) Prior Publication Data

US 2018/0083208 A1 Mar. 22, 2018

Related U.S. Application Data

(60) Continuation of application No. 14/554,725, filed on Nov. 26, 2014, now Pat. No. 10,153,444, which is a continuation of application No. 13/420,289, filed on Mar. 14, 2012, now Pat. No. 8,940,415, which is a division of application No. 12/395,358, filed on Feb. 27, 2009, now Pat. No. 8,211,553, which is a division of application No. 10/551,653, filed as application No. PCT/JP2004/007882 on Jun. 1, 2004, now Pat. No. 7,569,692.

(30) Foreign Application Priority Data

Jun. 2, 2003 (JP) .................. 2003-157006
Mar. 26, 2004 (JP) .................. 2004-092274

(51) Int. Cl.

| | | |
|---|---|---|
| H01L 51/54 | (2006.01) |
| C09K 11/06 | (2006.01) |
| H01L 51/00 | (2006.01) |
| H01L 51/50 | (2006.01) |
| C07F 15/00 | (2006.01) |
| C07C 251/24 | (2006.01) |
| C07D 213/22 | (2006.01) |
| C07D 213/53 | (2006.01) |
| H01L 51/52 | (2006.01) |
| H05B 33/14 | (2006.01) |

(52) U.S. Cl.
CPC ........ *H01L 51/0087* (2013.01); *C07C 251/24* (2013.01); *C07D 213/22* (2013.01); *C07D 213/53* (2013.01); *C07F 15/0033* (2013.01); *C07F 15/0086* (2013.01); *C07F 15/0093* (2013.01); *C09K 11/06* (2013.01); *H01L 51/0085* (2013.01); *H01L 51/5012* (2013.01); *H01L 51/5016* (2013.01); *H01L 51/5203* (2013.01); *H05B 33/14* (2013.01); *C09K 2211/1029* (2013.01); *C09K 2211/1037* (2013.01); *C09K 2211/1044* (2013.01); *C09K 2211/1059* (2013.01); *C09K 2211/1092* (2013.01); *C09K 2211/182* (2013.01); *C09K 2211/185* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 6,303,231 B1 | 10/2001 | Sawada | |
| 6,303,238 B1 | 10/2001 | Thompson | |
| 6,316,130 B1 | 11/2001 | Heuer | |
| 6,653,654 B1 | 11/2003 | Che | |
| 7,332,232 B2 | 2/2008 | Ma | |
| 7,361,415 B2 | 4/2008 | Che | |
| 7,442,797 B2 | 10/2008 | Itoh | |
| 7,569,692 B2 * | 8/2009 | Nii et al. ............... | C07C 251/24 257/E51.044 |
| 7,728,137 B2 | 6/2010 | Stoessel | |
| 7,732,606 B2 * | 6/2010 | Ise et al. ............. | C07F 15/0086 257/E51.044 |
| 8,202,631 B2 * | 6/2012 | Ise et al. ............. | C07F 15/0086 257/E51.044 |

(Continued)

FOREIGN PATENT DOCUMENTS

| | | |
|---|---|---|
| EP | 0969532 A2 | 1/2000 |
| EP | 1623973 A1 | 2/2006 |

(Continued)

OTHER PUBLICATIONS

Ma. Baldo et al., 'Highly efficient phosphorescent emission from organic electroluminescent devices', Nature, vol. 395, Sep. 10, 1998, pp. 151-154.
Chan, C.-W. et al., 'Covalently Linked Donor-Acceptor Cyclometalated Platinum(II) Complexes. Structure and Luminescent Properties,' J. Am. Chem. Soc. (1993), vol. 115, p. 11245-11253, XP-002976306.
Chassot et al. cis-Bis(2-Phenylpyridine)platinum(II) (CBPPP). A Simple Molecular Platinum Compound, Helvetica Chimica Acta, vol. 66, No. 8, p. 2443-2444 (1983), XP55017704.
Yong-Yue Lin et al., 'Structural, Photophysical, and Electrophosphorescent Properties of Platinum (II) Complexes Supported by Tetradentate N.sub.2O.sub.2 Chelates', Chem. Eur. J. (2003), vol. 9, No. 6, pp. 1263-1272.
Constable, E.C. et al., 'A double helix dinickel(II) complex with a 1,3-phenylene spacer group through spontaneous self organization,' Angewandte Chemie (1992), vol. 104, No. 2, pp. 218-220, XP-002312313, CAPLUS AN 1992:186499, (abstract only).

(Continued)

*Primary Examiner* — Marie R. Yamnitzky
(74) *Attorney, Agent, or Firm* — Riverside Law LLP

(57) ABSTRACT

An organic electroluminescent device, which has a pair of electrodes and at least one organic layer including a luminescent layer between the pair of electrodes, wherein at least one layer between the pair of electrodes comprises at least one metal complex having a tridentate- or higher polydentate-chain structure ligand.

23 Claims, No Drawings

(56) References Cited

U.S. PATENT DOCUMENTS

| | | | |
|---|---|---|---|
| 8,609,259 B2 * | 12/2013 | Igarashi et al. | C07D 471/22 257/E51.044 |
| 8,940,415 B2 | 1/2015 | Nii | |
| 2002/0008233 A1 | 1/2002 | Forrest | |
| 2002/0013306 A1 | 1/2002 | Lowe | |
| 2002/0055014 A1 | 5/2002 | Okada | |
| 2002/0068190 A1 | 6/2002 | Tsuboyama | |
| 2002/0094453 A1 | 7/2002 | Takiguchi | |
| 2002/0179885 A1 | 12/2002 | Che | |
| 2003/0059647 A1 | 3/2003 | Thompson | |
| 2003/0152802 A1 | 8/2003 | Tsuboyama | |
| 2003/0205707 A1 | 11/2003 | Chi-Ming | |
| 2004/0180234 A1 | 9/2004 | Lee | |
| 2005/0123788 A1 | 6/2005 | Huo | |
| 2005/0170206 A1 | 8/2005 | Ma | |
| 2005/0170209 A1 | 8/2005 | Lee | |
| 2006/0063031 A1 | 3/2006 | Brown | |
| 2006/0073359 A1 | 4/2006 | Ise | |
| 2006/0134460 A1 | 6/2006 | Kondakova | |
| 2006/0134461 A1 | 6/2006 | Huo | |
| 2006/0182992 A1 | 8/2006 | Nii | |
| 2006/0264625 A1 | 11/2006 | Nakayama | |
| 2006/0286406 A1 | 12/2006 | Igarashi | |
| 2007/0082284 A1 | 4/2007 | Stoessel | |
| 2007/0103060 A1 | 5/2007 | Itoh | |
| 2008/0001530 A1 | 1/2008 | Ise | |
| 2008/0036373 A1 | 2/2008 | Itoh | |
| 2009/0128008 A1 | 5/2009 | Ise | |
| 8,211,553 B2 | 7/2012 | Nii | |

FOREIGN PATENT DOCUMENTS

| | | | |
|---|---|---|---|
| JP | H059470 A | 1/1993 | |
| JP | H08319482 A | 12/1996 | |
| JP | 2000048960 A | 2/2000 | |
| JP | 2000503982 A | 4/2000 | |
| JP | 0070655 A2 | 11/2000 | |
| JP | 0170395 A2 | 9/2001 | |
| JP | 2001338768 A | 12/2001 | |
| JP | 2002175884 A | 6/2002 | |
| JP | 2002305083 A | 10/2002 | |
| JP | 2002363552 A | 12/2002 | |
| JP | 2003068466 A | 3/2003 | |
| JP | 2003073355 A | 3/2003 | |
| JP | 2003123976 A | 4/2003 | |
| JP | 2003123981 A | 4/2003 | |
| JP | 2003147345 A | 5/2003 | |
| JP | 2003520391 A | 7/2003 | |
| JP | 2004331506 A | 11/2004 | |
| JP | 2004331508 A | 11/2004 | |
| JP | 2005220136 A | 8/2005 | |
| JP | 2005310733 A | 11/2005 | |
| JP | 2007019462 A | 1/2007 | |
| JP | 2007073845 A | 3/2007 | |
| JP | 2007519614 A | 7/2007 | |
| JP | 2008037848 A | 2/2008 | |
| JP | 2008103535 A | 5/2008 | |
| JP | 4110173 B2 | 7/2008 | |
| JP | 2008524848 A | 7/2008 | |
| JP | 4460952 B2 | 5/2010 | |
| WO | 0057676 A1 | 9/2000 | |
| WO | 02060910 | 8/2002 | |
| WO | 03093283 A1 | 11/2003 | |
| WO | 2004039914 A1 | 5/2004 | |
| WO | WO 2004/099339 A1 * | 11/2004 | |
| WO | 2004108857 A1 | 12/2004 | |
| WO | 2005042444 A2 | 5/2005 | |
| WO | 2005042550 A1 | 5/2005 | |

OTHER PUBLICATIONS

European Search Report, dated Feb. 2, 2012, for European Patent Application No. 04735658.9.
JPO Office Action, issued Nov. 11, 2009, for Japanese Application No. 2004-279153, with English translation.
JPO Office Action, dated Nov. 4, 2009, for Japanese Patent Application No. 2004-162849, with English translation.
SIPO Office Action, dated Aug. 4, 2010, for Chinese Application No. 2009-10168315.6, with English translation.
SIPO Office Action, dated Dec. 28, 2011, for Chinese Application No. 2009-10168315.6, with English translation.
USPTO Office Action, dated Aug. 25, 2011, for U.S. Appl. No. 12/395,358 (parent application).
USPTO Restriction/Election Requirement, dated Jun. 10, 2011, for U.S. Appl. No. 12/395,358 (parent application).
USPTO Restriction/Election Requirement, dated Nov. 17, 2008, for U.S. Appl. No. 10/551,653 (parent of parent application).
European Office Action dated Jul. 16, 2012 in the corresponding European Patent Application No. 04735658.9.
Japanese Office Action dated Jul. 31, 2012 in the corresponding Japanese Patent Application No. 2009-293567 with an English translation.
International Search Report, dated Sep. 28, 2004; International Application No. PCT/JP2004/007882.
Office Action dated Feb. 26, 2018 for U.S. Appl. No. 14/554,725; (pp. 1-11).
EP Search Report dated Jul. 18, 2017; EP Applicatin No. EP 17 16 3955 (9 pages).

* cited by examiner

ORGANIC ELECTROLUMINESCENT DEVICES AND METAL COMPLEX COMPOUNDS

This application is a continuation of U.S. patent application Ser. No. 14/554,725, filed on Nov. 26, 2014, which is a continuation of U.S. patent application Ser. No. 13/420,289, filed on Mar. 14, 2012, now U.S. Pat. No. 8,940,415, which is a divisional of U.S. patent application Ser. No. 12/395,358, filed Feb. 27, 2009, now U.S. Pat. No. 8,211,553, which is a divisional of U.S. patent application Ser. No. 10/551,653, filed on Sep. 29, 2005, now U.S. Pat. No. 7,569,692, which is a National Stage of International Application No. PCT/JP2004/07882, filed Jun. 1, 2004, which claims the benefit of priority of Application No. 2004-092274, filed in Japan on Mar. 26, 2004, and Application No. 2003-157006, filed in Japan on Jun. 2, 2003. The entire contents of all of the above applications are hereby incorporated by reference.

TECHNICAL FIELD

The present invention relates to organic electroluminescent devices (luminescent devices or EL devices) to convert electric energy into light. Further, the present invention relates to metal complexes to be used suitably in the organic electroluminescent devices.

BACKGROUND ART

Recently, a variety of types of display devices are actively researched and developed. Among these, much attention is focused on organic electroluminescent (EL) devices. This is because organic EL devices are promising display devices capable of emitting light of high luminance under low applied voltage.

Recently, application of organic EL devices to color displays and white light sources has been actively studied. However, development on high-grade color displays and white light sources requires enhancing the characteristics (performances) of blue-, green-, and red-emitting devices.

On the other hand, as luminescent devices using a red-emitting phosphorescent material, those using a cyclic tetradentate ligand-containing platinum porphyrin complex as a light-emitting material are known by, for example, Nature 395, 151 (1998) and U.S. Pat. No. 6,303,231 B1. However, because these devices are low in maximum luminance (brightness), enhancement of the maximum luminance has been desired.

Further, there are reports on platinum porphyrin complexes containing a bipyridine-series or phenanthroline-series chain tetradentate ligand (see Chem. Eur. J., 9, No. 6, 1264 (2003), U.S. Pat. No. 6,653,654 B1 and WO 03/093283A1). However, these complexes do not compatibly satisfy both durability and luminous characteristics, such as color purity. Accordingly, improvement on these properties is desired. Also with respect to green-emitting luminescent materials and blue-emitting luminescent materials that emit in a shorter wavelength region than the aforementioned luminescent materials, there is a need for development of advanced materials that are excellent in both luminous characteristics and durability.

DISCLOSURE OF THE INVENTION

According to the present invention, there are provided the following means:

[1] An organic electroluminescent device, comprising a pair of electrodes, and at least one organic layer including a luminescent layer between the pair of electrodes, wherein at least one layer between the pair of electrodes comprises at least one metal complex having a tridentate- or higher polydentate-chain structure ligand.

[2] The organic electroluminescent device described in [1], wherein a metal ion in the metal complex is selected from the group consisting of platinum, iridium, rhenium, palladium, rhodium, ruthenium and copper ions.

[3] The organic electroluminescent device described in [1] or [2], wherein the metal complex has no carbon-metal bond.

[4] The organic electroluminescent device described in any one of [1] to [3], wherein the metal complex is a phosphorescent emissive metal complex, and said metal complex is incorporated in the luminescent layer.

[5] The organic electroluminescent device described in any one of [1] to [4], wherein the metal complex is a compound represented by formula (1):

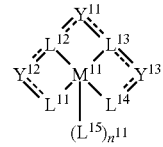

Formula (1)

wherein, $M^{11}$ represents a metal ion; $L^{11}$, $L^{12}$, $L^{13}$, $L^{14}$, and $L^{15}$ each represent a ligand to coordinate to $M^{11}$; $L^{11}$ and $L^{14}$ do not combine together via an atomic group, to form a cyclic ligand; $L^{15}$ does not bond to both $L^{11}$ and $L^{14}$, to form a cyclic ligand; $Y^{11}$, $Y^{12}$, and $Y^{13}$ each represent a linking group, a single bond, or a double bond; a bond between L and $Y^{12}$, a bond between $Y^{12}$ and $L^{12}$, a bond between $L^{12}$ and $Y^{11}$, a bond between $Y^{11}$ and $L^{13}$, a bond between $L^{13}$ and $Y^{13}$, and a bond between $Y^{13}$ and $L^{14}$ each represent a single bond, or a double bond; $n^{11}$ represents 0 to 4.

[6] The organic electroluminescent device described in any one of [1] to [5], wherein the metal complex is a compound represented by formula (2):

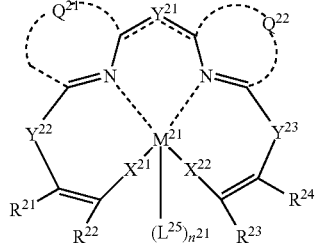

Formula (2)

wherein, $M^{21}$ represents a metal ion; $Y^{21}$ represents a linking group, a single bond, or a double bond; $Y^{22}$ and $Y^{23}$ each represent a single bond or a linking group; $Q^{21}$ and $Q^{22}$ each represent an atomic group necessary to form a nitrogen-containing heterocycle; a bond between $Y^{21}$ and the ring formed with $Q^{21}$, and a bond between $Y^{21}$ and the ring formed with $Q^{22}$ each represent a single bond, or a double bond; $X^{21}$ and $X^{22}$ each represent an oxygen atom, a sulfur atom, or a substituted or unsubstituted nitrogen atom; $R^{21}$, $R^{22}$, $R^{23}$, and $R^{24}$ each represent a hydrogen atom, or a substituent; $R^{21}$ and $R^{22}$, and $R^{23}$ and $R^{24}$, respectively, may bond to each other to form a ring; $L^{25}$ represents a ligand to coordinate to $M^{21}$; $n^{21}$ represents an integer of 0 to 4.

[7] The organic electroluminescent device described in [6], wherein the metal complex is a compound represented by formula (2) in which the ring formed with $Q^{21}$ and the ring formed with $Q^{22}$ each are a pyridine ring, and $Y^{21}$ represents a linking group composed of at least one atom.

[8] The organic electroluminescent device described in [6], wherein the metal complex is a compound represented by formula (2) in which the ring formed with $Q^{21}$ and the ring formed with $Q^{22}$ each are a pyridine ring, $Y^{21}$ represents a single bond or a double bond, and $X^{21}$ and $X^{22}$ each represent a sulfur atom or a substituted or unsubstituted nitrogen atom.

[9] The organic electroluminescent device described in [6], wherein the metal complex is a compound represented by formula (2) in which the ring formed with $Q^{21}$ and the ring formed with $Q^{22}$ each are a 5-membered nitrogen-containing heterocycle.

[10] The organic electroluminescent device described in [6], wherein the metal complex is a compound represented by formula (2) in which the ring formed with $Q^{21}$ and the ring formed with $Q^{22}$ each are a 6-membered heterocycle containing at least two nitrogen atoms.

[11] The organic electroluminescent device described in [1] or [2], wherein the metal complex is a compound represented by formula (9):

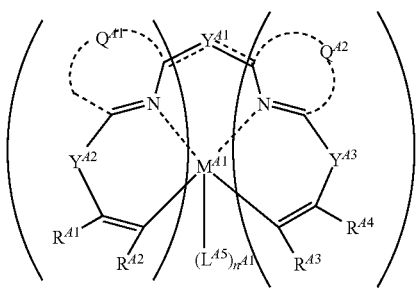

Formula (9)

wherein, $M^{41}$ represents a metal ion; $Q^{41}$ and $Q^{42}$ each represent an atomic group necessary to form a nitrogen-containing heterocycle; $R^{41}$, $R^{42}$, $R^{43}$, and $R^{44}$ each represent a hydrogen atom, or a substituent; $R^{41}$ and $R^{42}$, and $R^{43}$ and $R^{44}$, respectively, may bond to each other to form a ring; $Y^{42}$ and $Y^{43}$ each represent a linking group or a single bond; $Y^{41}$ represents a linking group, a single bond or double bond for linking two bidentate ligands in parentheses together; $L^{45}$ represents a ligand to coordinate to $M^{41}$; $n^{41}$ represents an integer of 0 to 4.

[12] The organic electroluminescent device described in [1] or [2], wherein the metal complex is a compound represented by formula (10):

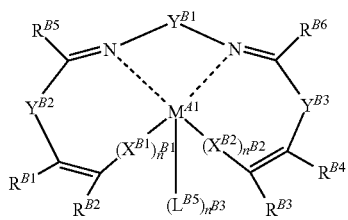

Formula (10)

wherein, $M^{B1}$ represents a metal ion; $Y^{B1}$ represents a linking group; $Y^{B2}$ and $Y^{B3}$ each represent a linking group or a single bond; $X^{B1}$ and $X^{B2}$ each represent an oxygen atom, a sulfur atom, or a substituted or unsubstituted nitrogen atom; $n^{B1}$ and $n^{B2}$ each represent an integer of 0 to 1; $R^{B1}$, $R^{B2}$, $R^{B3}$, $R^{B4}$, $R^{B5}$, and $R^{B6}$ each represent a hydrogen atom, or a substituent; $R^{B1}$ and $R^{B2}$, and $R^{B3}$ and $R^{B4}$, respectively, may bond to each other to form a ring; $L^{B5}$ represents a ligand to coordinate to $M^{B1}$; $n^{B3}$ represents an integer of 0 to 4; and $Y^{B1}$ does not link to $R^{B5}$ or $R^{B6}$.

[13] The organic electroluminescent device described in any one of [1] to [4], wherein the metal complex is a compound represented by formula (8):

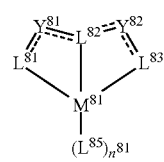

Formula (8)

wherein, $M^{81}$ represents a metal ion; $L^{81}$, $L^{82}$, $L^{83}$, and $L^{85}$ each represent a ligand to coordinate to $M^{81}$; $L^{81}$ and $L^{83}$ do not combine together via an atomic group, to form a cyclic ligand or a tetradentate or higher-polydentate ligand; $L^{85}$ does not directly bond to $L^{81}$ or $L^{83}$, but bonds to via the metal; $Y^{81}$ and $Y^{82}$ each represent a linking group, a single bond, or a double bond; $n^{81}$ represents an integer of 0 to 3.

[14] The organic electroluminescent device described in [13], wherein the metal complex is a compound represented by formula (8) in which $L^{81}$, $L^{82}$, and $L^{83}$ each represent an aromatic carbocycle or heterocycle to coordinate to $M^{81}$ via a carbon atom, or a nitrogen-containing heterocycle to coordinate to $M^{81}$ via a nitrogen atom, and at least one of $L^{81}$, $L^{82}$, and $L^{83}$ is said nitrogen-containing heterocycle.

[15] The organic electroluminescent device described in [1] or [2], wherein the metal complex is a compound represented by formula (X1):

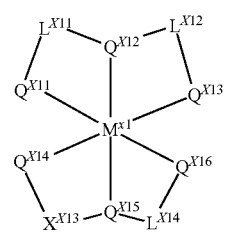

Formula (X1)

wherein, $M^{X1}$ represents a metal ion; $Q^{X11}$, $Q^{X12}$, $Q^{X13}$, $Q^{X14}$, $Q^{X15}$, and $Q^{X16}$ each represent an atom to coordinate to $M^{X1}$ or an atomic group having an atom to coordinate to $M^{X1}$; $L^{X11}$, $L^{X12}$, $L^{X13}$, and $L^{X14}$ each represent a single bond, a double bond, or a linking group; an atomic group consisted of $Q^{X11}$-$L^{X1}$-$Q^{X12}$-$L^{X12}$-$Q^{X13}$ and an atomic group consisted of $Q^{X14}$-$L^{X13}$-$Q^{X15}$-$L^{X14}$-$Q^{X16}$ each represent a tridentate ligand; and a bond between $M^{X1}$ and $Q^{X11}$, a bond between $M^{X1}$ and $Q^{X12}$, a bond between $M^{X1}$ and $Q^{X13}$, a bond between $M^{X1}$ and $Q^{X14}$, a bond between $M^{X1}$ and $Q^{X15}$, and a bond between $M^{X1}$ and $Q^{X16}$ each are a coordinate bond or a covalent bond.

[16] The organic electroluminescent device described in [15], wherein the metal complex represented by formula (X1) is a compound represented by formula (X2):

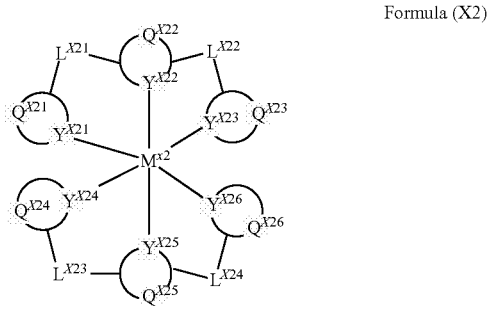

Formula (X2)

wherein, $M^{X2}$ represents a metal ion; $Y^{X21}$, $Y^{X22}$, $Y^{X23}$, $Y^{X24}$, $Y^{X25}$, and $Y^{X26}$ each represent an atom to coordinate to $M^{X2}$; each of $Q^{X21}$, $Q^{X22}$, $Q^{X23}$, $Q^{X24}$, $Q^{X25}$, and $Q^{X26}$ respectively represents an atomic group necessary to form an aromatic ring or heterocyclic ring together with each of $Y^{X21}$, $Y^{X22}$, $Y^{X23}$, $Y^{X24}$, $Y^{X25}$, and $Y^{X26}$, respectively; $L^{X21}$, $L^{X22}$, $L^{23}$, and $L^{X24}$ each represent a single bond, a double bond, or a linking group; and a bond between a bond between $M^{X2}$ and $Y^{X21}$, a bond between $M^{X2}$ and $Y^{X22}$, a bond between $M^{X2}$ and $Y^{X23}$, a bond between $M^{X2}$ and $Y^{X24}$, a bond between $M^{X2}$ and $Y^{X25}$, and a bond between $M^{X2}$ and $Y^{X26}$ each are a coordinate bond or a covalent bond.

[17] The organic electroluminescent device described in [15], wherein the metal complex represented by formula (X1) is a compound represented by formula (X3):

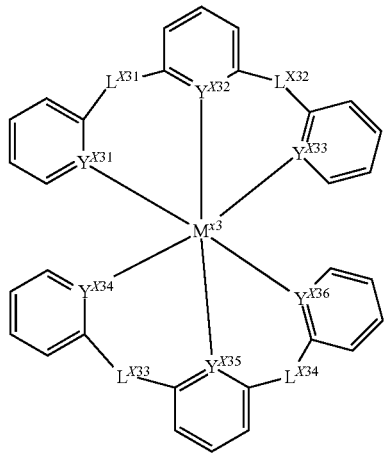

Formula (X3)

wherein, $M^{X3}$ represents a metal ion; $Y^{X31}$, $Y^{X32}$, $Y^{X33}$, $Y^{X34}$, $Y^{X35}$, and $Y^{X36}$ each represent a carbon atom, a nitrogen atom, or a phosphorus atom; $L^{X31}$, $L^{X32}$, $L^{X33}$, and $L^{X34}$ each represent a single bond, a double bond, or a linking group; and a bond between $M^{X3}$ and $Y^{X31}$, a bond between $M^{X3}$ and $Y^{X32}$, a bond between $M^{X3}$ and $Y^{X33}$, a bond between $M^{X3}$ and $Y^{X34}$, a bond between $M^{X3}$ and $Y^{X35}$, and a bond between $M^{X3}$ and $Y^{X36}$ each are a coordinate bond or a covalent bond.

[18] The organic electroluminescent device described in any one of [1] to [17], wherein the organic layer comprises at least one luminescent layer and a hole transporting layer, and the organic layer further comprises at least one layer selected from the group consisting of an exciton-blocking layer, a hole injection layer, a hole-blocking layer and an electron-transporting layer.

[19] The organic electroluminescent device described in any one of [1] to [18], wherein the organic layer comprises at least one luminescent layer, and a host material of the luminescent layer is selected from the group consisting of an amine compound, a metal chelate oxynoid compound (i.e. a compound having a metal-oxygen bond) in which the metal is aluminum, zinc or transition metals, a polyarylene compound, a condensed aromatic carbocyclic compound, and a non-complex aromatic heterocyclic compound.

[20] The organic electroluminescent device described in any one of [1] to [19], wherein the organic layer comprises at least one electron-transporting layer in which an electron-transporting material is selected from the group consisting of a metal chelate oxynoid compound, a polyarylene compound, a condensed aromatic carbocyclic compound and a non-complex aromatic heterocyclic compound.

[21] The organic electroluminescent device described in any one of [1] to [20], wherein the organic layer comprises at least one luminescent layer, and a host material of the luminescent layer is composed of at least two compounds.

[22] A compound represented by formula (11):

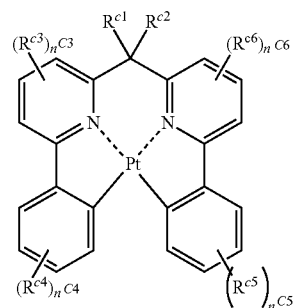

Formula (11)

wherein, $R^{C1}$ and $R^{C2}$ each represent a hydrogen atom or a substituent; $R^{C3}$, $R^{C4}$, $R^{C5}$, and $R^{C6}$ each represent a substituent; $n^{C3}$ and $n^{C6}$ each represent an integer of 0 to 3; $n^{C4}$ and $n^{C5}$ each represent an integer of 0 to 4; when a plurality of $R^{C3}$, $R^{C4}$, $R^{C5}$ or $R^{C6}$ exists, the respective $R^{C3}$s, $R^{C4}$s, $R^{C5}$s or $R^{C6}$s may be the same or different from each other, and, respectively, the $R^{C3}$s, $R^{C4}$s, $R^{C5}$s, or $R^{C6}$s may bond to each other to form a condensed ring.

[23] A compound represented by formula (12):

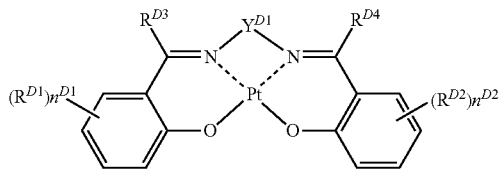

Formula (12)

wherein, $R^{D3}$ and $R^{D4}$ each represent a hydrogen atom or a substituent; $R^{D1}$ and $R^{D2}$ each represent a substituent; $n^{D1}$ and $n^{D2}$ each represent an integer of 0 to 4; when a plurality of $R^{D1}$ or $R^{D2}$ exists, the respective $R^{D1}$s or $R^{D2}$s may be the same or different from each other, and, respectively, the $R^{D1}$s or $R^{D2}$s may bond to each other to form a ring; and $Y^{D1}$ represents a vinyl group that substitutes with 1- and 2-positions, a phenylene group, a pyridine ring, a pyrazine ring, a pyrimidine ring or a methylene group having 1 to 8 carbon atoms.

[24] A compound represented by formula (X1):

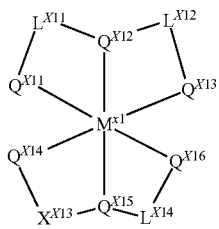

Formula (X1)

wherein, $M^{X1}$ represents a metal ion; $Q^{X11}$, $Q^{X12}$, $Q^{X13}$, $Q^{X14}$, $Q^{X15}$, and $Q^{X16}$ each represent an atom to coordinate to $M^{X1}$ or an atomic group having an atom to coordinate to $M^{X1}$; $L^{X11}$, $L^{X12}$, $L^{X13}$, and $L^{X14}$ each represent a single bond, a double bond, or a linking group; an atomic group consisted of $Q^{X11}$-$L^{X11}$-$Q^{X12}$-$L^{X12}$-$Q^{X13}$ and an atomic group consisted of $Q^{X14}$-$L^{X13}$-$Q^{X15}$-$L^{X14}$-$Q^{X16}$ each represent a tridentate ligand; and a bond between $M^{X1}$ and $Q^{X11}$, a bond between $M^{X1}$ and $Q^{X12}$, a bond between $M^{X1}$ and $Q^{X13}$, a bond between $M^{X1}$ and $Q^{X14}$, a bond between $M^{X1}$ and $Q^{X15}$, and a bond between $M^{X1}$ and $Q^{X16}$ each are a coordinate bond or a covalent bond.

[25] A compound represented by formula (X2):

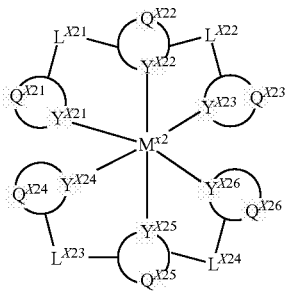

Formula (X2)

wherein, $M^{X2}$ represents a metal ion; $Y^{X21}$, $Y^{X22}$, $Y^{X23}$, $Y^{X24}$, $Y^{X25}$, and $Y^{X26}$ each represent an atom to coordinate to $M^{X2}$; each of $Q^{X21}$, $Q^{X22}$, $Q^{X23}$, $Q^{X24}$, $Q^{X25}$, and $Q^{X26}$ respectively represents an atomic group necessary to form an aromatic ring or heterocyclic ring together with each of $Y^{X21}$, $Y^{X22}$, $Y^{X23}$, $Y^{X24}$, $Y^{X25}$, and $Y^{X26}$, respectively; $L^{X21}$, $L^{X22}$, $L^{X23}$, and $L^{X24}$ each represent a single bond, a double bond, or a linking group; and a bond between $M^{X2}$ and $Y^{X21}$, a bond between $M^{X2}$ and $Y^{X24}$, a bond between $M^{X2}$ and $Y^{X25}$, a bond between $M^{X2}$ and $Y^{X24}$, a bond between $M^{X2}$ and $Y^{X25}$, and a bond between $M^{X2}$ and $Y^{X26}$ each are a coordinate bond or a covalent bond.

[26] A compound represented by formula (X3):

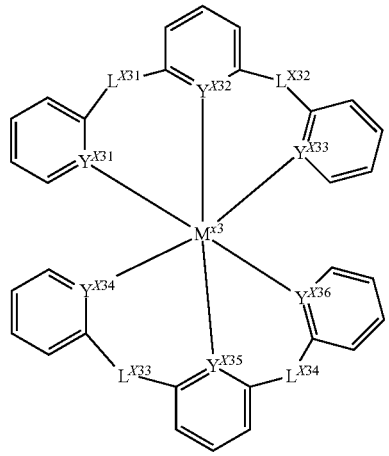

Formula (X3)

wherein, $M^{X3}$ represents a metal ion; $Y^{X31}$, $Y^{X32}$, $Y^{X33}$, $Y^{X34}$, $Y^{X35}$, and $Y^{X36}$ each represent a carbon atom, a nitrogen atom, or a phosphorus atom; $L^{X31}$, $L^{X32}$, $L^{X33}$, and $L^{X34}$ each represent a single bond, a double bond, or a linking group; and a bond between $M^{X3}$ and $Y^{X31}$, a bond between $M^{X3}$ and $Y^{X32}$, a bond between $M^{X3}$ and $Y^{X33}$, a bond between $M^{X3}$ and $Y^{X34}$, a bond between $M^{X3}$ and $Y^{X35}$, and a bond between $M^{X3}$ and $Y^{X36}$ each are a coordinate bond or a covalent bond.

The term "chain ligand" used in this specification means ligands except cyclic ligands such as porphyrin and phthalocyanine. Taken formula (8) as an example, said term means such ligands that $L^{81}$ and $L^{83}$ do not directly connect but are bound via $Y^{81}$, $L^{82}$, $Y^{82}$, and $M^{81}$. Even in the case where $L^{81}$, $Y^{81}$, $L^{82}$, $Y^{82}$, or $L^{83}$ contains a ring structure such as benzene, pyridine, and quinoline, the ligand is referred to as a chain ligand, as long as $L^{81}$ and $L^{83}$ do not directly combine but combine via $Y^{81}$, $L^{82}$, $Y^{82}$, and $M^{81}$. An additional atomic group may exist between $L^{81}$ and $Y^{81}$, or $Y^{81}$ and $L^{82}$ or $L^{82}$ and $Y^{82}$, or $Y^{82}$ and $L^{83}$, to form a ring.

Other and further features and advantages of the invention will appear more fully from the following description.

BEST MODE FOR CARRYING OUT THE INVENTION

The organic electroluminescent device of the present invention (hereinafter sometimes referred to as a device of the present invention) is characterized in that the device contains a pair of electrodes and at least one organic layer including a luminescent layer (the organic layer may consist of organic compounds, or may additionally contain inorganic compounds), between the pair of electrodes, in which any layer between the pair of electrodes contains a phosphorescent emissive metal complex having a tridentate- or higher polydentate-chain ligand.

As the metal complex having a tridentate- or higher polydentate-chain ligand for use in the present invention (hereinafter sometimes referred to as a metal complex of the present invention), metal complexes having from tridentate- to octadentate-chain ligand are preferable, metal complexes having from tetradentate- to octadentate-chain ligand are more preferable, metal complexes having from tetradentate- to hexadentate-chain ligand are furthermore preferable, and metal complexes having tetradentate-chain ligand are most preferable.

The chain ligand for use in the present invention preferably contains at least one nitrogen-containing heterocycle (e.g., pyridine, quinoline, pyrrole rings) to coordinate to the central metal {if formula (1) is taken as an example, said metal is represented by $M^{11}$} via a nitrogen atom.

It is preferable for the metal complex of the present invention not to have a carbon-metal bond. Namely it is preferable that there is no bond between a metal atom and a carbon atom in the metal complex. Specifically illustrating about the term "not to have a carbon-metal bond", the metal compound preferably has any of the bonds described below. That is, a metal-nitrogen bond, a metal-oxygen bond, a metal-sulfur bond, a metal-phosphorus bond, and a metal-selenium bond are preferable. A metal-nitrogen bond, a metal-oxygen bond, a metal-sulfur bond, and a metal-phosphorus bond are more preferable. A metal-nitrogen bond, a metal-oxygen bond, and a metal-sulfur bond are furthermore preferable.

The compound for use in the present invention is not particularly restricted, so long as the compound is a phosphorescent emissive compound. Preferred are compounds to emit phosphorescence preferably at not less than −30° C., more preferably at not less than −10° C., furthermore preferably at not less than 0° C., and particularly preferably at not less than 10° C. The compound may emit fluorescence at the same time. In this case, preferred are compound whose intensity of phosphorescence at 20° C. is not less than 2 times, more preferably not less than 10 times, furthermore preferably not less than 100 times, the intensity of fluorescence.

It is preferable for the phosphorescent material for use in the present invention to have a phosphorescent quantum yield (20° C.) of not less than 10% and the phosphorescent λmax (phosphorescent emission maximum) in the range of from 400 nm to 700 nm, more preferably a phosphorescent quantum yield (20° C.) of not less than 15% and the phosphorescent λmax in the range of from 400 nm to 575 nm, and furthermore preferably a phosphorescent quantum yield (20° C.) of not less than 20% and the phosphorescent λmax in the range of from 400 nm to 560 nm.

The metal complex of the present invention is incorporated in any layer between a pair of electrodes, preferably it is incorporated in a hole injection/hole transporting layer and/or a luminescent layer (light-emitting layer), and more preferably in a luminescent layer. In the case where the metal complex of the present invention is incorporated in the luminescent layer, a density of the phosphorescent emissive compound in the luminescent layer is preferably in the range of from 1 to 30% by mass, more preferably in the range of from 2 to 20% by mass, and further more preferably in the range of from 3 to 15% by mass, based on the mass of the luminescent layer respectively.

A preferable embodiment of the metal complex of the present invention having a tetradentate or higher polydentate ligand is represented by formula (1). The preferable embodiment of the metal complex represented by formula (1) is one represented by formula (2), (5), (9), or (10).

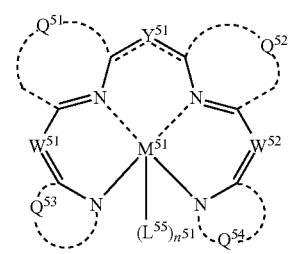

Formula (5)

A preferable embodiment of the metal complex represented by formula (2) is one represented by formula (3).

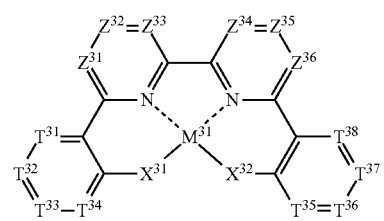

Formula (3)

A preferable embodiment of the metal complex represented by formula (9) is one represented by formula (6) or (7), and a preferable embodiment of the metal complex represented by formula (7) is one represented by formula (11).

A preferable embodiment of the metal complex represented by formula (10) is one represented by formula (12).

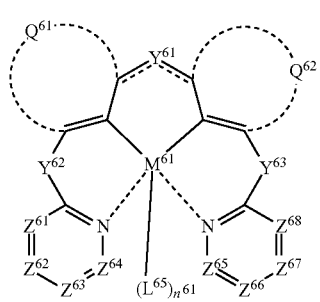

Formula (6)

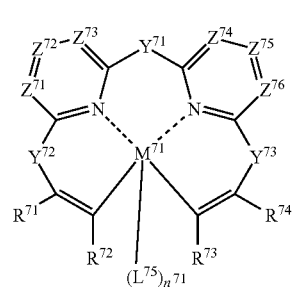

Formula (7)

In the following, the compound represented by formula (1) will be described.

$M^{11}$ represents a metal ion. The metal ion is not particularly restricted, but divalent or trivalent metal ions are preferable. As the divalent or trivalent metal ions, platinum, iridium, rhenium, palladium, rhodium, ruthenium, copper, europium, gadolinium, and terbium ions are preferable. Of these ions, platinum, iridium and europium ions are more preferable; platinum and iridium ions are furthermore preferable; and a platinum ion is particularly preferable.

$L^{11}$, $L^{12}$, $L^{13}$, and $L^{14}$ each represent a ligand to coordinate to $M^{11}$. As the atom that is contained in $L^{11}$, $L^{12}$, $L^{13}$, or $L^{14}$ and coordinates to $M^{11}$, nitrogen, oxygen, sulfur, and carbon atoms are preferable, and nitrogen, oxygen and carbon atoms are more preferable.

The bond to be formed between $M^{11}$ and $L^{11}$, $L^{12}$, $L^{13}$, or $L^{14}$ may be a covalent bond, an ion bond, or a coordination bond. The ligand that is composed of $L^{11}$, $Y^{12}$, $L^{12}$, $Y^{11}$, $L^{13}$, $Y^{13}$, and $L^{14}$ is preferably an anionic ligand (i.e., a ligand that bonds to a metal with at least one anion of the ligand). The number of anions in the anionic ligand is preferably 1 to 3, more preferably 1 or 2, and furthermore preferably 2.

$L^{11}$, $L^{12}$, $L^{13}$, or $L^{14}$ to coordinate to $M^{11}$ via a carbon atom, is not particularly restricted. Examples of these ligands include imino ligands, aromatic carbocyclic ligands (for example, benzene, naphthalene, anthracene, phenanthracene ligands), heterocyclic ligands {for example, thiophene, pyridine, pyrazine, pyrimidine, thiazole, oxazole, pyrrole, imidazole, pyrazole ligands, condensed rings containing these rings (e.g., quinoline, benzothiazole ligands), and tautomers of these rings}.

$L^{11}$, $L^{12}$, $L^{13}$, or $L^{14}$ to coordinate to $M^{11}$ via a nitrogen atom is not particularly restricted. Examples of these ligands include nitrogen-containing heterocyclic ligands {for example, pyridine, pyrazine, pyrimidine, pyridazine, triazine, thiazole, oxazole, pyrrole, imidazole, pyrazole, triazole, oxadiazole, and thiadiazole ligands, condensed rings containing any of these ligands (e.g., quinoline, benzoxazole, benzimidazole ligands), and tautomers of these ligands (the tautomers are defined in the present invention as it means that the following examples are also embraced in the tautomer in addition to ordinary tautomers; for example, the 5-membered heterocyclic ligand of compound (24), the terminal 5-membered heterocyclic ligand of compound (64), and a 5-membered heterocyclic ligand of compound (145) are defined as pyrrole tautomers)}, and amino ligands {for example, alkylamino ligands (those having carbon atoms preferably in the range of 2 to 30, more preferably in the range of 2 to 20, and particularly preferably in the range of 2 to 10; for example, methylamino), arylamino ligands (for example, phenylamino), acylamino ligands (those having carbon atoms preferably in the range of 2 to 30, more preferably in the range of 2 to 20, and particularly preferably in the range of 2 to 10; for example, acetylamino, benzoylamino), alkoxycarbonylamino ligands (those having carbon atoms preferably in the range of 2 to 30, more preferably in the range of 2 to 20, and particularly preferably in the range of 2 to 12; for example, methoxycarbonylamino), aryloxycarbonylamino ligands (those having carbon atoms preferably in the range of 7 to 30, more preferably in the range of 7 to 20, and particularly preferably in the range of 7 to 12; for example, phenyloxycarbonylamino), sulfonylamino ligands (those having carbon atoms preferably in the range of 1 to 30, more preferably in the range of 1 to 20, and particularly preferably in the range of 1 to 12; for example, methane sulfonylamino, benzene sulfonylamino), imino ligands}. These ligands may be further substituted with a substituent.

$L^{11}$, $L^{12}$, $L^{13}$, or $L^{14}$ to coordinate to $M^{11}$ via an oxygen atom is not particularly restricted. Examples of these ligands include alkoxy ligands (those having carbon atoms preferably in the range of 1 to 30, more preferably in the range of 1 to 20, and particularly preferably in the range of 1 to 10; for example, methoxy, ethoxy, butoxy, 2-ethylhexyloxy), aryloxy ligands (those having carbon atoms preferably in the range of 6 to 30, more preferably in the range of 6 to 20, and particularly preferably in the range of 6 to 12; for example, phenyloxy, 1-naphthyloxy, 2-naphthyloxy), heterocyclic oxy ligands (those having carbon atoms preferably in the range of 1 to 30, more preferably in the range of 1 to 20, and particularly preferably in the range of 1 to 12; for example, pyridyloxy, pyrazyloxy, pyrimidyloxy, quinolyloxy), acyloxy ligands (those having carbon atoms preferably in the range of 2 to 30, more preferably in the range of 2 to 20, and particularly preferably in the range of 2 to 10; for example, acetoxy, benzoyloxy), silyloxy ligands (those having carbon atoms preferably in the range of 3 to 40, more preferably in the range of 3 to 30, and particularly preferably in the range of 3 to 24; for example, trimethylsilyloxy, triphenyl silyloxy), carbonyl ligands (for example, ketone ligands, ester ligands, amide ligands), and ether ligands (for example, dialkylether ligands, diarylether ligands, furyl ligands).

$L^{11}$, $L^{12}$, $L^{13}$, or $L^{14}$ to coordinate to $M^{11}$ via a sulfur atom is not particularly restricted. Examples of these ligands include alkylthio ligands (those having carbon atoms preferably in the range of 1 to 30, more preferably in the range of 1 to 20, and particularly preferably in the range of 1 to 12; for example, methylthio, ethylthio), arylthio ligands (those having carbon atoms preferably in the range of 6 to 30, more preferably in the range of 6 to 20, and particularly preferably in the range of 6 to 12; for example, phenylthio), heterocyclic thio ligands (those having carbon atoms preferably in the range of 1 to 30, more preferably in the range of 1 to 20, and particularly preferably in the range of 1 to 12; for example, pyridylthio, 2-benzimidazolylthio, 2-benzoxazolylthio, 2-benzthiazolylthio), thiocarbonyl ligands (for example, thioketone ligands, thioester ligands), and thioether ligands (for example, dialkylthioether ligands, diarylthioether ligands, thiofuryl ligands). Further, these ligands may be further substituted with a substituent.

Preferably, $L^{11}$ and $L^{14}$ each are an aromatic carbocyclic ligand, an alkyloxy ligand, an aryloxy ligand, an ether ligand, an alkylthio ligand, an arylthio ligand, an alkylamino ligand, an arylamino ligand, an acylamino ligand, and a nitrogen-containing heterocyclic ligand (for example, pyridine, pyrazine, pyrimidine, pyridazine, triazine, thiazole, oxazole, pyrrole, imidazole, pyrazole, triazole, oxadiazole, and thiadiazole ligands; a condensed ligand containing any of these ligands (e.g., quinoline, benzoxazole, benzimidazole ligands); and a tautomer of any of these ligands). Of these ligands, an aromatic carbocyclic ligand, an aryloxy ligand, an arylthio ligand, an arylamino ligand, a pyridine ligand, a pyrazine ligand, an imidazole ligand, a condensed ligand containing any of these ligands (e.g., quinoline, quinoxaline, benzimidazole ligands); and a tautomer of any of these ligands are more preferable. An aromatic carbocyclic ligand, an aryloxy ligand, an arylthio ligand, and an arylamino ligand are furthermore preferable with the aromatic carbocyclic ligand and aryloxy ligand being most preferable.

$L^{12}$ and $L^{13}$ each are preferably a ligand to form a coordinate bond with $M^{11}$. As the ligand to form a coordinate bond with $M^{11}$, a pyridine ring, a pyrazine ring, a pyrimidine ring, a triazine ring, a thiazole ring, an oxazole ring, a pyrrole ring, a triazole ring, a condensed ring containing any of these rings (e.g., quinoline, benzoxazole, benzimidazole, and indolenine rings); and a tautomer of any of these rings are preferable. Of these, a pyridine ring, a pyrazine ring, a pyrimidine ring, a pyrrole ring, a condensed ring containing any of these rings (e.g., quinoline, benzpyrrole rings); and a tautomer of any of these rings are preferable. A pyridine ring, a pyrazine ring, a pyrimidine ring, and a condensed ring containing any of these rings (e.g., a quinoline ring) are more preferable. A pyridine ring and a condensed ring containing a pyridine ring (e.g., a quinoline ring) are particularly preferable.

$L^{15}$ represents a ligand to coordinate to $M^{11}$. $L^{15}$ is preferably a monodentate to tetradentate ligand, more preferably an anionic, monodentate to tetradentate ligand. The anionic, monodentate to tetradentate ligand is not particularly restricted, but it is preferably a halogen ligand, a 1,3-diketone ligand (e.g., acetylacetone ligand), a monoanionic bidentate ligand containing a pyridine ligand (e.g., picolinic acid, 2-(2-hydroxyphenyl)-pyridine ligands), and a tetradentate ligand formed with $L^{11}$, $Y^{12}$, $L^{12}$, $Y^{11}$, $L^{13}$, $Y^{13}$ and $L^{14}$; more preferably a 1,3-diketone ligand (e.g., acetylacetone ligand), a monoanionic bidentate ligand containing a pyridine ligand (e.g., picolinic acid, 2-(2-hydroxyphenyl)-pyridine ligands), and a tetradentate ligand formed with $L^{11}$, $Y^{12}$, $L^{12}$, $Y^{11}$, $L^{13}$, $Y^{13}$, and $L^{14}$; furthermore preferably a 1,3-diketone ligand (e.g., acetylacetone ligand), and a monoanionic bidentate ligand containing a pyridine ligand (e.g., picolinic acid, 2-(2-hydroxyphenyl)-pyridine ligands); and particularly preferably a 1,3-diketone ligand (e.g., acetylacetone ligand). The coordination numbers and ligand numbers do not exceed the coordination number of the metal. $L^{15}$ does not bond to both $L^{11}$ and $L^{14}$, to form a cyclic ligand together with them.

$Y^{11}$, $Y^{12}$, and $Y^{13}$ each represent a linking group, a single bond or a double bond. The linking group is not particularly restricted. Examples of the linking group include a carbonyl linking group, a thiocarbonyl linking group, an alkylene group, an alkenylene group, an arylene group, a heteroarylene group, an oxygen atom-linking group, an nitrogen atom-linking group, a silicon atom-linking group, and a linking group comprising a combination of these groups. A bond between $L^{11}$ and $Y^{12}$, a bond between $Y^{12}$ and $L^{12}$, a bond between $L^{12}$ and $Y^{11}$, a bond between $Y^{11}$ and $L^{13}$, a bond between $L^{13}$ and $Y^{13}$ and a bond between $Y^{13}$ and $L^{14}$ each represent a single bond, or a double bond.

$Y^{11}$, $Y^{12}$, and $Y^{13}$ each are preferably a single bond, a double bond, a carbonyl linking group, an alkylene linking group or an alkenylene group. $Y^{11}$ is more preferably a single bond or an alkylene group, and furthermore preferably an alkylene group. $Y^{12}$ and $Y^{13}$ each are more preferably a single bond or an alkenylene group, and furthermore preferably a single bond.

The member numbers of the ring formed by $Y^{12}$, $L^{11}$, $L^{12}$, and $M^{11}$, the ring formed by $Y^{11}$, $L^{12}$, $L^{13}$, and $M^{11}$, and the ring formed by $Y^{13}$, $L^{13}$, $L^{14}$ and $M^{11}$ each are preferably in the range of from 4 to 10, more preferably in the range of from 5 to 7, and furthermore preferably 5 or 6.

$n^{11}$ represents 0 to 4. When $M^{11}$ is a metal that has a coordination number of 4, n is 0. When $M^{11}$ is a metal that has a coordination numbers of 6, $n^{11}$ is preferably 1 or 2, more preferably 1. When $M^{11}$ is a metal that has a coordination number of 6 and $n^{11}$ is 1, $L^{15}$ represents a bidentate ligand. When $M^{11}$ is a metal that has a coordination number of 6 and $n^{11}$ is 2, $L^{15}$ represents a monodentate ligand. When $M^{11}$ is a metal that has a coordination number of 8, $n^{11}$ is preferably 1 to 4, more preferably 1 or 2, and furthermore preferably 1. When $M^{11}$ is a metal that has a coordination number of 8 and $n^{11}$ is 1, $L^{15}$ represents a tetradentate ligand, whereas when $n^{11}$ is 2, $L^{15}$ represents a bidentate ligand. When n is 2 or more, plural $L^{15}$s may be the same or different from each other.

Next, the compound represented by formula (2) will be described.

$M^{21}$ has the same meaning as that of the aforementioned $M^{11}$, with the same preferable range.

$Q^{21}$ and $Q^{22}$ each represent a group for forming a nitrogen-containing heterocycle (a ring containing a nitrogen atom that coordinates to $M^{21}$). The nitrogen-containing heterocycle formed by $Q^{21}$ or $Q^{22}$ is not particularly limited, and examples include a pyridine ring, a pyrazine ring, a pyrimidine ring, a triazine ring, a thiazole ring, an oxazole ring, a pyrrole ring, a triazole ring, a condensed ring containing any of these rings (e.g., quinoline, benzoxazole, benzimidazole, and indolenine rings); and a tautomer of these rings.

The nitrogen-containing heterocycle formed by $Q^{21}$ or $Q^{22}$ is preferably a pyridine ring, a pyrazine ring, a pyrimidine ring, a pyridazine ring, a triazine ring, a pyrazole ring, an imidazole ring, an oxazole ring, a pyrrole ring, a benzazole ring, a condensed ring containing any of these rings (e.g., quinoline, benzoxazole, and benzimidazole rings); and a tautomer of any of these rings. The nitrogen-containing heterocycle formed by $Q^{21}$ or $Q^{22}$ is more preferably a pyridine ring, a pyrazine ring, a pyrimidine ring, an imidazole ring, a pyrrole ring, a condensed ring containing any of these rings (e.g., quinoline ring); and a tautomer of any of these rings. The nitrogen-containing heterocycle formed by $Q^{21}$ or $Q^{22}$ is further preferably a pyridine ring, a condensed ring containing a pyridine ring (e.g., quinoline ring); and particularly preferably a pyridine ring.

$X^{21}$ and $X^{22}$ each are preferably an oxygen atom, a sulfur atom, or a substituted or unsubstituted nitrogen atom. They each are more preferably an oxygen atom, a sulfur atom, or a substituted nitrogen atom; further preferably an oxygen atom or a sulfur atom; and particularly preferably an oxygen atom.

$Y^{21}$ has the same meaning as that of the aforementioned $Y^{11}$, with the same preferable range.

$Y^{22}$ and $Y^{23}$ each represent a single bond or a linking group, and preferably a single bond. The linking group is not particularly restricted. Examples of the linking group include a carbonyl-linking group, a thiocarbonyl-linking group, an alkylene group, an alkenylene group, an arylene group, a hetero arylene group, an oxygen atom-linking group, a nitrogen atom-linking group, and a linking group formed by a combination of any of these linking groups.

As the aforementioned linking group, a carbonyl linking group, an alkylene linking group and an alkenylene linking group are preferable. Of these, a carbonyl linking group and an alkenylene linking group are more preferable with the carbonyl-linking group being furthermore preferable.

$R^{21}$, $R^{22}$, $R^{23}$, and $R^{24}$ each represent a hydrogen atom, or a substituent. The substituent is not particularly limited. Examples of the substituent include an alkyl group (preferably having 1 to 30 carbon atoms, more preferably having 1 to 20 carbon atoms, and particularly preferably having 1 to 10 carbon atoms, e.g., methyl, ethyl, iso-propyl, tert-butyl, n-octyl, n-decyl, n-hexadecyl, cyclopropyl, cyclopentyl, cyclohexyl), an alkenyl group (preferably having 2 to 30 carbon atoms, more preferably having 2 to 20 carbon atoms, and particularly preferably having 2 to 10 carbon atoms, e.g., vinyl, allyl, 2-butenyl, 3-pentenyl), an alkynyl group (preferably having 2 to 30 carbon atoms, more preferably having 2 to 20 carbon atoms, and particularly preferably having 2 to 10 carbon atoms, e.g., propargyl, 3-pentynyl), an aryl group (preferably having 6 to 30 carbon atoms, more preferably having 6 to 20 carbon atoms, and particularly preferably having 6 to 12 carbon atoms, e.g., phenyl, p-methylphenyl, naphthyl, anthranyl), an amino group (preferably having 0 to 30 carbon atoms, more preferably having 0 to 20 carbon atoms, and particularly preferably having 0 to 10 carbon atoms, e.g., amino, methylamino, dimethylamino, diethylamino, dibenzylamino, diphenylamino, ditolylamino), an alkoxy group (preferably having 1 to 30 carbon atoms, more preferably having 1 to 20 carbon atoms, and particularly preferably having 1 to 10 carbon atoms, e.g., methoxy, ethoxy, butoxy, 2-ethylhexyloxy), an aryloxy group (preferably having 6 to 30 carbon atoms, more preferably having 6 to 20 carbon atoms, and particularly preferably having 6 to 12 carbon atoms, e.g., phenyloxy, 1-naphthyloxy, 2-naphthyloxy), a heterocyclic oxy group (preferably having 1 to 30 carbon atoms, more preferably having 1 to 20 carbon atoms, and particularly preferably having 1 to 12 carbon atoms, e.g., pyridyloxy, pyrazyloxy, pyrimidyloxy, quinolyloxy), an acyl group (preferably having 1 to 30 carbon atoms, more preferably having 1 to 20 carbon atoms, and particularly preferably having 1 to 12 carbon atoms, e.g., acetyl, benzoyl, formyl, pivaloyl), an alkoxycabonyl group (preferably having 2 to 30 carbon atoms, more preferably having 2 to 20 carbon atoms, and particularly preferably having 2 to 12 carbon atoms, e.g., methoxycarbonyl, ethoxycarbonyl), an aryloxycarbonyl group (preferably having 7 to 30 carbon atoms, more preferably having 7 to 20 carbon atoms, and particularly preferably having 7 to 12 carbon atoms, e.g., phenyloxycarbonyl), an acyloxy group (preferably having 2 to 30 carbon atoms, more preferably having 2 to 20 carbon atoms, and particularly preferably having 2 to 10 carbon atoms, e.g., acetoxy, benzoyloxy), an acylamino group (preferably having 2 to 30 carbon atoms, more preferably having 2 to 20 carbon atoms, and particularly preferably having 2 to 10 carbon atoms, e.g., acetylamino, benzoylamino), an alkoxycarbonylamino group (preferably having 2 to 30 carbon atoms, more preferably having 2 to 20 carbon atoms, and particularly preferably having 2 to 12 carbon atoms, e.g., methoxycarbonylamino), an aryloxycarbonylamino group (preferably having 7 to 30 carbon atoms, more preferably having 7 to 20 carbon atoms, and particularly preferably having 7 to 12 carbon atoms, e.g., phenyloxycarbonylamino), a sulfonylamino group (preferably having 1 to 30 carbon atoms, more preferably having 1 to 20 carbon atoms, and particularly preferably having 1 to 12 carbon atoms, e.g., methanesulfonylamino, benzenesulfonylamino), a sulfamoyl group (preferably having 0 to 30 carbon atoms, more preferably having 0 to 20 carbon atoms, and particularly preferably having 0 to 12 carbon atoms, e.g., sulfamoyl, methylsulfamoyl, dimethylsulfamoyl, phenylsulfamoyl), a carbamoyl group (preferably having 1 to 30 carbon atoms, more preferably having 1 to 20 carbon atoms, and particularly preferably having 1 to 12 carbon atoms, e.g., carbamoyl, methylcarbamoyl, diethylcarbamoyl, phenylcarbamoyl), an alkyl thio group (preferably having 1 to 30 carbon atoms, more preferably having 1 to 20 carbon atoms, and particularly preferably having 1 to 12 carbon atoms, e.g., methylthio, ethylthio), an aryl thio group (preferably having 6 to 30 carbon atoms, more preferably having 6 to 20 carbon atoms, and particularly preferably having 6 to 12 carbon atoms, e.g., phenylthio), a heterocyclic thio group (preferably having 1 to 30 carbon atoms, more preferably having 1 to 20 carbon atoms, and particularly preferably having 1 to 12 carbon atoms, e.g., pyridyl thio, 2-benzimidazolyl thio, 2-benzoxazolyl thio, 2-benzthiazolyl thio), a sulfonyl group (preferably having 1 to 30 carbon atoms, more preferably having 1 to 20 carbon atoms, and particularly preferably having 1 to 12 carbon atoms, e.g., mesyl, tosyl), a sulfinyl group (preferably having 1 to 30 carbon atoms, more preferably having 1 to 20 carbon atoms, and particularly preferably having 1 to 12 carbon atoms, e.g., methanesulfinyl, benzenesulfinyl), a ureido group (preferably having 1 to 30 carbon atoms, more preferably having 1 to 20 carbon atoms, and particularly preferably having 1 to 12 carbon atoms, e.g., ureido, methylureido, phenylureido), a phosphoric acid amido group (preferably having 1 to 30 carbon atoms, more preferably having 1 to 20 carbon atoms, and particularly preferably having 1 to 12 carbon atoms, e.g., diethyl phosphoamido, phenyl phosphoamido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (preferably having 1 to 30 carbon atoms, more preferably having 1 to 12 carbon atoms, and containing a hetero atom such as nitrogen, oxygen and sulfur, specifically for example, imidazolyl, pyridyl, quinolyl, furyl, thienyl, piperidyl, morpholino, benzoxazolyl, benzimidazolyl, benzthiazolyl, carbazolyl, azepinyl), a silyl group (preferably having 3 to 40 carbon atoms, more preferably having 3 to 30 carbon atoms, and particularly preferably having 3 to 24 carbon atoms, e.g., trimethylsilyl, triphenylsilyl), and a silyloxy group (preferably having 3 to 40 carbon atoms, more preferably having 3 to 30 carbon atoms, and particularly preferably having 3 to 24 carbon atoms, e.g., trimethylsilyloxy, triphenylsilyloxy). These substituents may be further substituted by another substituent.

Preferably, $R^{21}$, $R^{22}$, $R^{23}$, and $R^{24}$, each are an alkyl group, an aryl group, a group that forms a condensed ring (for example, benzo-condensed rings, pyridine-condensed rings) by forming a bond between $R^{21}$ and $R^{22}$, or between $R^{23}$ and $R^{24}$. More preferably, $R^{21}$, $R^{22}$, $R^{23}$, and $R^{24}$, each are a group that forms a condensed ring (for example, benzo-condensed rings, pyridine-condensed rings) by forming a bond between $R^{21}$ and $R^{22}$, or between $R^{23}$ and $R^{24}$.

$L^{25}$ has the same meaning as that of the aforementioned $L^{15}$, with the same preferable range.

$n^{21}$ has the same meaning as that of the aforementioned $n^{11}$, with the same preferable range.

Among metal complexes represented by formula (2), those in which the ring formed by $Q^{21}$ and the ring formed by $Q^{22}$ each are a pyridine ring and $Y^{21}$ represents a linking group; those in which the ring formed by $Q^{21}$ and the ring formed by $Q^{22}$ each are a pyridine ring, $Y^{22}$ represents a single bond or a double bond and $X^{21}$ and $X^{22}$ each represent a sulfur atom or a substituted or unsubstituted nitrogen atom; and those in which the ring formed by $Q^{21}$ and the ring formed by $Q^{22}$ each are a nitrogen-containing 5-membered heterocycle or a nitrogen-containing 6-membered heterocycle containing two or more nitrogen atoms, are preferable.

Next, the compound represented by formula (3) will be described.

$M^{31}$ has the same meaning as that of the aforementioned $M^{11}$, with the same preferable range.

$Z^{31}$, $Z^{32}$, $Z^{33}$, $Z^{34}$, $Z^{35}$, and $Z^{36}$ each represent a substituted or unsubstituted carbon atom or a nitrogen atom, with the substituted or unsubstituted carbon atom being preferable. Examples of the substituent on the carbon atom include those explained in the aforementioned $R^{21}$. Further, $Z^{31}$ and $Z^{32}$, $Z^{32}$ and $Z^{33}$, $Z^{33}$ and $Z^{34}$, $Z^{34}$ and $Z^{35}$, $Z^{35}$ and $Z^{36}$ each may bond to each other via a linking group, to form a condensed ring (for example, a benzo-condensed ring, a pyridine-condensed ring). Alternatively, $Z^{31}$ and $T^{31}$, and $Z^{36}$ and $T^{38}$ each may bond to each other via a linking group, to form a condensed ring (for example, a benzo-condensed ring, a pyridine-condensed ring).

As the aforementioned substituent on the carbon atom, an alkyl group, an alkoxy group, an alkylamino group, an aryl group, a group to form a condensed ring (for example, a benzo-condensed ring, a pyridine-condensed ring) and a halogen atom are preferable. Of these, an alkylamino group, an aryl group and a group to form a condensed ring (for example, a benzo-condensed ring, a pyridine-condensed ring) are more preferable. An aryl group and a group to form a condensed ring (for example, a benzo-condensed ring, a pyridine-condensed ring) are furthermore preferable. A group to form a condensed ring (for example, a benzo-condensed ring, a pyridine-condensed ring) is most preferable.

$T^{31}$, $T^{32}$, $T^{33}$, $T^{34}$, $T^{35}$, $T^{36}$, $T^{37}$ and $T^{38}$ each represent a substituted or unsubstituted carbon atom or a nitrogen atom, with the substituted or unsubstituted carbon atom being preferable. Examples of the substituent on the carbon atom include those explained in the aforementioned $R^{21}$. $T^{31}$ and $T^{32}$, $T^{32}$ and $T^{33}$, $T^{33}$ and $T^{34}$, $T^{35}$ and $T^{36}$, $T^{36}$ and $T^{37}$, $T^{37}$ and $T^{38}$ each may bond to each other via a linking group, to form a condensed ring (for example, a benzo-condensed ring).

As the aforementioned substituent on the carbon atom, an alkyl group, an alkoxy group, an alkylamino group, an aryl group, a group to form a condensed ring (for example, a benzo-condensed ring, a pyridine-condensed ring) and a halogen atom are preferable. Of these, an aryl group, a group to form a condensed ring (for example, a benzo-condensed ring, a pyridine-condensed ring), and a halogen atom are more preferable. An aryl group and a halogen atom are furthermore preferable. An aryl group is most preferable.

$X^{31}$ and $X^{32}$ have the same meanings as those of the aforementioned $X^{21}$ and $X^{22}$, respectively, with the same preferable ranges.

Next, the compound represented by formula (5) will be described.

$M^{51}$ has the same meaning as that of the aforementioned $M^{11}$, with the same preferable range.

$Q^{51}$ and $Q^{52}$ have the same meanings as those of the aforementioned $Q^{21}$ and $Q^{22}$, respectively, with the same preferable ranges.

$Q^{53}$ and $Q^{54}$ each represent a group to form a nitrogen-containing heterocycle (a ring containing a nitrogen to coordinate to $M^{51}$). The nitrogen-containing heterocycle formed by $Q^{53}$ or $Q^{54}$ is not particularly restricted, but preferably a tautomer of pyrrole derivatives, a tautomer of imidazole derivatives (for example, a 5-membered heterocyclic ligand of compound (29)), a tautomer of thiazole derivatives (for example, a 5-membered heterocyclic ligand of compound (30)) and a tautomer of oxazole derivatives (for example, a 5-membered heterocyclic ligand of compound (31)), more preferably a tautomer of pyrrole derivatives, a tautomer of imidazole derivatives and a tautomer of thiazole derivatives, furthermore preferably a tautomer of pyrrole derivatives and a tautomer of imidazole derivatives, and especially preferably a tautomer of pyrrole derivatives.

$Y^{51}$ has the same meaning as that of the aforementioned $Y^{11}$, with the same preferable range.

$L^{55}$ has the same meaning as that of the aforementioned $L^{15}$, with the same preferable range.

$n^{51}$ has the same meaning as that of the aforementioned $n^{11}$, with the same preferable range.

$W^{51}$ and $W^{52}$ each are preferably a substituted or unsubstituted carbon atom or a nitrogen atom. They each are more preferably an unsubstituted carbon atom or a nitrogen atom; further preferably an unsubstituted carbon atom.

Next, the compound represented by formula (9) will be described.

$M^{41}$, $Q^{41}$, $Q^{42}$, $Y^{41}$, $Y^{42}$, $Y^{43}$, $R^{41}$, $A^2$, $R^{43}$, $R^{44}$, $L^{45}$, and $n^{41}$ have the same meanings as those of the aforementioned $M^{21}$, $Q^{21}$, $Q^{22}$, $Y^{21}$, $Y^{22}$, $Y^{23}$, $R^{21}$, $R^{22}$, $R^{23}$, $R^{24}$, $L^{25}$, and $n^{21}$ in formula (2), respectively, with the same preferable ranges.

Next, the compound represented by formula (6) will be described.

$M^{61}$ has the same meaning as that of the aforementioned $M^{11}$, with the same preferable range.

$Q^{61}$ and $Q^{62}$ each represent a group to form a ring. The ring formed by $Q^{61}$ or $Q^{62}$ is not particularly restricted. As the ring, there are illustrated, for example, benzene, pyridine, pyridazine, pyrimidine, thiophene, isothiazole, furane, isoxazole rings and condensed rings thereof.

The ring formed by $Q^{61}$ or $Q^{62}$ is preferably a benzene, pyridine, thiophene, or thiazole ring or a condensed ring thereof, more preferably a benzene or pyridine ring, or a condensed ring thereof, and furthermore preferably a benzene ring and a condensed ring thereof.

$Y^{61}$ has the same meaning as that of the aforementioned $Y^{11}$ with the same preferable range.

$Y^{62}$ and $Y^{63}$ each represent a linking group or a single bond. The linking group is not particularly restricted. Examples of the linking group include a carbonyl-linking group, a thiocarbonyl-linking group, an alkylene group, an alkenylene group, an arylene group, a hetero arylene group, an oxygen atom-linking group, a nitrogen atom-linking group, and a linking group formed by a combination of these linking groups.

Preferably, $Y^{62}$ and $Y^{63}$ each are a single bond, a carbonyl-linking group, an alkylene linking group, or an alkenylene group, more preferably they each are a single bond or an alkenylene group, and further more preferably a single bond.

$L^{65}$ has the same meaning as that of the aforementioned $L^{15}$, with the same preferable range.

$n^{61}$ has the same meaning as that of the aforementioned $n^{11}$, with the same preferable range.

$Z^{61}$, $Z^{62}$, $Z^{63}$, $Z^{64}$, $Z^{65}$, $Z^{66}$, $Z^{67}$, and $Z^{68}$ each represent a substituted or unsubstituted carbon atom or a nitrogen atom with the substituted or unsubstituted carbon atom being preferable. Examples of the substituent on the carbon atom include those explained in the aforementioned $R^{21}$. Further, $Z^{61}$ and $Z^{62}$, $Z^{62}$ and $Z^{63}$, $Z^{63}$ and $Z^{64}$, $Z^{65}$ and $Z^{66}$, $Z^{66}$ and $Z^{67}$, $Z^{67}$ and $Z^{68}$ each may bond to each other via a linking group, to form a condensed ring (for example, a benzo-condensed ring, a pyridine-condensed ring). The ring formed by $Q^{61}$ or $Q^{62}$ may bond to $Z^{61}$ or $Z^{68}$ respectively via a linking bond, to form a ring.

As the aforementioned substituent on the carbon atom, an alkyl group, an alkoxy group, an alkylamino group, an aryl group, a group to form a condensed ring (for example, a benzo-condensed ring, a pyridine-condensed ring) and a halogen atom are preferable. Of these, an alkylamino group, an aryl group and a group to form a condensed ring (for example, a benzo-condensed ring, a pyridine-condensed ring) are more preferable. An aryl group and a group to form a condensed ring (for example, a benzo-condensed ring, a pyridine-condensed ring) are furthermore preferable. A group to form a condensed ring (for example, a benzo-condensed ring, a pyridine-condensed ring) is most preferable.

Next, the compound represented by formula (7) will be described.

$M^{71}$ has the same meaning as that of the aforementioned $M^{11}$, with the same preferable range.

$Y^{71}$, $Y^{72}$, and $Y^{73}$ each have the same meanings as those of the aforementioned $Y^{62}$, with the same preferable ranges.

$L^{75}$ has the same meaning as that of the aforementioned $L^{15}$, with the same preferable range.

$n^{71}$ has the same meaning as that of the aforementioned $n^{11}$, with the same preferable range.

$Z^{71}$, $Z^{72}$, $Z^{73}$, $Z^{74}$, $Z^{75}$, and $Z^{76}$ each represent a substituted or unsubstituted carbon atom or a nitrogen atom, with the substituted or unsubstituted carbon atom being preferable. Examples of the substituent on the carbon atom include those explained in the aforementioned $R^{21}$. Further, $Z^{71}$ and $Z^{72}$, and $Z^{73}$ and $Z^{74}$ each may bond to each other via a linking group, to form a condensed ring (for example, a benzo-condensed ring, a pyridine-condensed ring).

$R^{71}$, $R^{72}$, $R^{73}$, and $R^{74}$ each have the same meanings as those of the aforementioned $R^{21}$, $R^{22}$, $R^{23}$, and $R^{24}$ in formula (2), with the same preferable ranges.

The compound represented by formula (11) will be described below.

$R^{C1}$ and $R^{C2}$ each represent a hydrogen atom or a substituent. The substituent represents an alkyl group or aryl group illustrated as examples of the substituent of $R^{21}$ to $R^{24}$ in formula (2). The substituents represented by $R^{C3}$, $R^{C4}$, $R^{C5}$, and $R^{C6}$ also have the same meanings as those of $R^{21}$ to $R^{24}$ in formula (2). $n^{C3}$ and $n^{C6}$ each represent an integer of 0 to 3. $n^{C4}$ and $n^{C5}$ each represent an integer of 0 to 4. When there are two or more $R^{C3}$s, $R^{C4}$s, $R^{C5}$s or $R^{C6}$s, the respective $R^{C3}$s, $R^{C4}$s, $R^{C5}$s or $R^{C6}$s may be the same or different from each other, and they may bond to each other to form a ring respectively. $R^{C3}$, $R^{C4}$, $R^{C5}$, and $R^{C6}$ each are preferably an alkyl group, an aryl group, a hetero aryl group, and a halogen atom.

Next, the compound represented by formula (10) will be explained.

$M^{B1}$, $Y^{B2}$, $Y^{B3}$, $R^{B1}$, $R^{B2}$, $R^{B3}$, $R^{B4}$, $L^{B5}$, $n^{B3}$, $X^{B1}$, and $X^{B2}$ each have the same meanings as $M^{21}$, $Y^{22}$, $Y^{23}$, $R^{21}$, $R^{22}$, $R^{23}$, $R^{24}$, $L^{25}$, $n^{21}$, $X^{21}$, and $X^{22}$ in formula (2) respectively, with the same preferable ranges. $Y^{B1}$ represents a linking group that is the same as $Y^{21}$ in formula (2), preferably a vinyl group that substitutes with 1- and 2-positions, a phenylene ring, a pyridine ring, a pyrazine ring, a pyrimidine ring or a methylene group having 2 to 8 carbon atoms. $R^{B5}$ and $R^{B6}$ each represent a hydrogen atom or a substituent. The substituent represents an alkyl group, aryl group or heterocyclic group illustrated as examples of the substituent of $R^{21}$ to $R^{24}$ in formula (2). However, $Y^{B1}$ does not link to $R^{B5}$ or $R^{B6}$. $n^{B1}$ and $n^{B2}$ each represent an integer of 0 to 1.

Next, the compound represented by formula (12) will be explained.

The substituents represented by $R^{D1}$, $R^{D2}$, $R^{D3}$, and $R^{D4}$ each have the same meanings as $R^{B5}$ and $R^{B6}$ in formula (10) with the same preferable ranges. $n^{D1}$ and $n^{D2}$ each represent an integer of 0 to 4. $Y^{D1}$ represents a vinyl group that substitutes with 1- and 2-positions, a phenylene ring, a pyridine ring, a pyrazine ring, a pyrimidine ring or a methylene group having 1 to 8 carbon atoms.

A preferable embodiment of the metal complex containing a tridentate ligand according to the present invention is illustrated by formula (8).

Next, the compound represented by formula (8) will be described.

$M^{81}$ has the same meaning as that of the aforementioned $M^{11}$, with the same preferable range.

$L^{81}$, $L^{82}$, and $L^{83}$ have the same meanings as those of the aforementioned $L^{11}$, $L^{12}$, and $L^{14}$, respectively, with the same preferable ranges.

$Y^{81}$ and $Y^{82}$ have the same meanings as those of the aforementioned $Y^{11}$ and $Y^{12}$, respectively, with the same preferable ranges.

$L^{85}$ represents a ligand to coordinate to $M^{81}$. $L^{85}$ is preferably a monodentate to tridentate ligand, and more preferably a monodentate to tridentate anionic ligand. The monodentate to tridentate anionic ligand is not particularly restricted, but preferably a halogen ligand, a tridentate ligand formed by $L^{81}$, $Y^{81}$, $L^{82}$, $Y^{82}$, and $L^{83}$, and more preferably a tridentate ligand formed by $L^{81}$, $Y^{83}$, $L^{82}$, $Y^{82}$, and $L^{83}$. $L^{85}$ does not directly bond to $L^{81}$ or $L^{83}$, but bonds to via the metal. The coordination numbers and ligand numbers do not exceed the coordination number of the metal.

$n^{81}$ represents from 0 to 5. When $M^{81}$ is a metal that has a coordination number of 4, $n^{81}$ is 1 and $L^{85}$ is a monodentate ligand. When $M^{81}$ is a metal that has a coordination number of 6, $n^{81}$ is preferably from 1 to 3, more preferably 1 or 3, and furthermore preferably 1. When $M^{81}$ is a metal that has a coordination number of 6 and $n^{81}$ is 1, $L^{85}$ is a tridentate ligand. When $M^{81}$ is a metal that has a coordination number of 6 and $n^{81}$ is 2, $L^{85}$s are a monodentate ligand and a bidentate ligand. When $M^{81}$ is a metal that has a coordination number of 6 and $n^{81}$ is 3, $L^{85}$ is a monodentate ligand. When $M^{81}$ is a metal that has a coordination number of 8, $n^{81}$ is preferably from 1 to 5, more preferably 1 or 2, and furthermore preferably 1. When $M^{81}$ is a metal that has a coordination number of 8 and $n^{81}$ is 1, $L^{85}$ is a pentadentate ligand; when $n^{81}$ is 2, $L^{85}$s are a tridentate ligand and a bidentate ligand; when $n^{81}$ is 3, $L^{85}$s are a tridentate ligand and two monodentate ligands, or they are two bidentate ligands and a monodentate ligand; when $n^{81}$ is 4, $L^{85}$s are a bidentate ligand and three monodentate ligands; when $n^{81}$ is 5, $L^{85}$s are five monodentate ligands. When $n^{81}$ is 2 or more, plural $L^{85}$s may be the same or different from each other.

A preferable embodiment of the compound represented by formula (8) is when $L^{81}$, $L^{82}$ and $L^{83}$ in formula (8) each represent an aromatic carbocycle or heterocycle to coordinate to $M^{81}$ via a carbon atom, or a nitrogen-containing heterocycle to coordinate to $M^{81}$ via a nitrogen atom, providing that at least one of $L^{81}$, $L^{82}$ and $L^{83}$ is said nitrogen-containing heterocycle. Examples of the aromatic carbocycle or heterocycle to coordinate to $M^{81}$ via a carbon atom, and nitrogen-containing heterocycle to coordinate to $M^{81}$ via a nitrogen atom are the same as the examples of the ligands to coordinate to $M^{11}$ via a carbon atom and the ligands to coordinate to $M^{11}$ via a nitrogen atom, which are illustrated in formula (1), with the same preferable ranges. $Y^{81}$ and $Y^{82}$ each are preferably a single bond or a methylene group.

Other preferable embodiments of the compound represented by formula (8) are those represented by formula (13) or (14).

Formula (13)

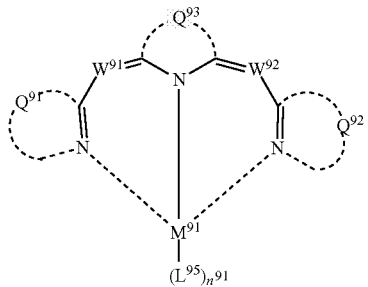

Formula (14)

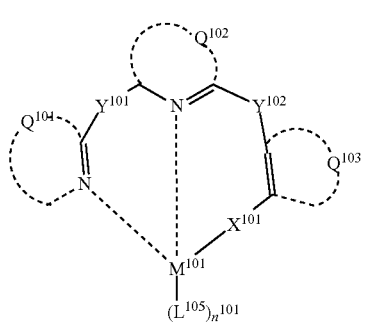

Next, the compound represented by formula (13) will be described.

$M^{91}$ has the same meaning as that of the aforementioned $M^{81}$, with the same preferable range.

$Q^{91}$ and $Q^{92}$ each represent a group to form a nitrogen-containing heterocycle (a ring containing a nitrogen to coordinate to $M^{91}$). The nitrogen-containing heterocycle formed by $Q^{91}$ or $Q^{92}$ is not particularly restricted, but preferably a pyridine, pyrazine, pyrimidine, pyridazine, triazine, thiazole, oxazole, pyrrole, pyrazole, imidazole, or triazole ring or a condensed ring containing any of these rings (e.g., quinoline, benzoxazole, benzimidazole, and indolenine rings); or a tautomer of any of these rings.

The nitrogen-containing heterocycle formed by $Q^{91}$ or $Q^{92}$ is preferably a pyridine, pyrazole, thiazole, imidazole, or pyrrole ring or a condensed ring containing any of these rings (e.g., quinoline, benzothiazole, benzimidazole, and indolenine rings) or a tautomer of any of these rings, more preferably a pyridine or pyrrole ring or a condensed ring containing any of these rings (e.g., quinoline ring) or a tautomer of any of these rings, still more preferably a pyridine ring and a condensed ring containing a pyridine ring, and particularly preferably a pyridine ring.

$Q^{93}$ represents a group to form a nitrogen-containing heterocycle (a ring containing a nitrogen to coordinate to $M^{91}$). The nitrogen-containing heterocycle formed by $Q^{93}$ is not particularly restricted, but preferably a tautomer of a pyrrole, imidazole or triazole ring or a condensed ring containing any of these rings (e.g., benzpyrrole ring), and more preferably a tautomer of a pyrrole ring, or a tautomer of a condensed ring containing a pyrrole ring (e.g., benzpyrrole ring).

$W^{91}$ and $W^{92}$ have the same meanings as those of the aforementioned $W^{51}$ and $W^{52}$, respectively, with the same preferable ranges.

$L^{95}$ has the same meaning as that of the aforementioned $L^{85}$, with the same preferable range.

$n^{91}$ has the same meaning as that of the aforementioned $n^{81}$, with the same preferable range.

Next, the compound represented by formula (14) will be described.

$M^{101}$ has the same meaning as that of the aforementioned $M^{81}$, with the same preferable range.

$Q^{102}$ has the same meaning as that of the aforementioned $Q^{21}$, with the same preferable range.

$Q^{101}$ has the same meaning as that of the aforementioned $Q^{91}$, with the same preferable range.

$Q^{103}$ represents a group to form an aromatic ring. The aromatic ring formed by $Q^{103}$ is not particularly restricted, but preferably a benzene, furane, thiophene, or pyrrole ring or a condensed ring containing any of these rings (e.g., naphthalene ring), more preferably a benzene ring or a condensed ring containing a benzene ring (e.g., naphthalene ring), and particularly preferably a benzene ring.

$Y^{101}$ and $Y^{102}$ each have the same meanings as those of the aforementioned $Y^{22}$, with the same preferable ranges.

$L^{105}$ has the same meaning as that of the aforementioned $L^{85}$, with the same preferable range.

$n^{101}$ has the same meaning as that of the aforementioned $n^{81}$, with the same preferable range.

$X^{101}$ has the same meaning as that of the aforementioned $X^{21}$, with the same preferable range.

The compound of the present invention may be a low molecular compound, or may be an oligomer compound or a polymer compound having a weight-average molecular weight calculated in terms of polystyrene preferably in the range of 1,000 to 5,000,000, more preferably in the range of 2,000 to 1,000,000, and furthermore preferably in the range of 3,000 to 100,000. With respect to the polymer compound, the structure represented, for example, by formula (1) may be contained in a main chain of the polymer, or in a side chain of the polymer. Further, the polymer compound may be a homopolymer or a copolymer. The compound of the present invention is preferably a low molecular compound.

Another preferable embodiment of the metal complex having a tridentate ligand of the present invention is a metal complex represented by formula (X1). Among the metal complexes represented by formula (X1), metal complexes represented by formula (X2) are preferable, and metal complexes represented by formula (X3) are more preferable.

The compound represented by formula (X1) will be described.

$M^{X1}$ represents a metal ion. The metal ion is not particularly restricted, but a monovalent to trivalent metal ion is preferable, a divalent or trivalent metal ion is more preferable, and a trivalent metal ion is furthermore preferable. Specifically, platinum, iridium, rhenium, palladium, rhodium, ruthenium, copper, europium, gadolinium, and terbium ions are preferable. Of these ions, platinum, iridium and europium ions are more preferable, platinum and iridium ions are furthermore preferable, and an iridium ion is particularly preferable.

$Q^{X11}$, $Q^{X12}$, $Q^{X13}$, $Q^{X14}$, $Q^{X15}$, and $Q^{X16}$ each represent an atom to coordinate to $M^{X1}$ or an atomic group having an atom to coordinate to $M^{X1}$. When $Q^{X11}$, $Q^{X12}$, $Q^{X13}$, $Q^{X14}$, $Q^{X15}$, or $Q^{X16}$ represents an atom to coordinate to $M^{X1}$, specific examples of the atom include a carbon atom, a nitrogen atom, an oxygen atom, a silicon atom, a phosphorus atom, and a sulfur atom; and preferably, the atom is a nitrogen atom, an oxygen atom, and a sulfur atom, or a phosphorus atom, and more preferably a nitrogen atom or an oxygen atom.

When $Q^{X11}$, $Q^{X12}$, $Q^{X13}$, $Q^{X14}$, $Q^{X15}$, or $Q^{X16}$ represents an atomic group having an atom to coordinate to $M^{X1}$, examples of the atomic group to coordinate to $M^{X1}$ via a carbon atom include an imino group, an aromatic hydrocarbon ring group (e.g., benzene, naphthalene), a heterocyclic ring group (e.g., thiophene, pyridine, pyrazine, pyrimidine, pyridazine, triazine, thiazole, oxazole, pyrrole, imidazole, pyrazole, triazole), a condensed ring including any of these rings, and a tautomer of any of these rings.

Examples of the atomic group to coordinate to $M^{X1}$ via a nitrogen atom include a nitrogen-containing heterocyclic ring group (e.g., pyridine, pyrazine, pyrimidine, pyridazine, triazine, thiazole, oxazole, pyrrole, imidazole, pyrazole, triazole), an amino group {e.g., an alkylamino group (having carbon atoms preferably in the range of 2 to 30, more preferably in the range of 2 to 20, and particularly preferably in the range of 2 to 10; for example, methylamino), an arylamino group (for example, phenylamino), an acylamino group (having carbon atoms preferably in the range of 2 to 30, more preferably in the range of 2 to 20, and particularly preferably in the range of 2 to 10; for example, acetylamino, benzoylamino), an alkoxycarbonylamino group (having carbon atoms preferably in the range of 2 to 30, more preferably in the range of 2 to 20, and particularly preferably in the range of 2 to 12; for example, methoxycarbonylamino), an aryloxycarbonylamino group (having carbon atoms preferably in the range of 7 to 30, more preferably in the range of 7 to 20, and particularly preferably in the range of 7 to 12; for example, phenyloxycarbonylamino), a sulfonylamino group (having carbon atoms preferably in the range of 1 to 30, more preferably in the range of 1 to 20, and particularly preferably in the range of 1 to 12; for example, methane sulfonylamino, benzene sulfonylamino)}, and an imino group. These groups may be further substituted with a substituent.

Examples of the atomic group to coordinate to $M^{X1}$ via an oxygen atom include an alkoxy group (having carbon atoms preferably in the range of 1 to 30, more preferably in the range of 1 to 20, and particularly preferably in the range of 1 to 10; for example, methoxy, ethoxy, butoxy, 2-ethylhexyloxy), an aryloxy group (having carbon atoms preferably in the range of 6 to 30, more preferably in the range of 6 to 20, and particularly preferably in the range of 6 to 12; for example, phenyloxy, 1-naphthyloxy, 2-naphthyloxy), a heterocyclic oxy group (having carbon atoms preferably in the range of 1 to 30, more preferably in the range of 1 to 20, and particularly preferably in the range of 1 to 12; for example, pyridyloxy, pyrazyloxy, pyrimidyloxy, quinolyloxy), an acyloxy group (having carbon atoms preferably in the range of 2 to 30, more preferably in the range of 2 to 20, and particularly preferably in the range of 2 to 10; for example, acetoxy, benzoyloxy), a silyloxy group (having carbon atoms preferably in the range of 3 to 40, more preferably in the range of 3 to 30, and particularly preferably in the range of 3 to 24; for example, trimethylsilyloxy, triphenylsilyloxy), a carbonyl group (for example, ketone group, ester group, amide group), and an ether group (for example, dialkylether group, diarylether group, furyl group).

Examples of the atomic group to coordinate to $M^{X1}$ via a sulfur atom include an alkylthio group (having carbon atoms preferably in the range of 1 to 30, more preferably in the range of 1 to 20, and particularly preferably in the range of 1 to 12; for example, methylthio, ethylthio), an arylthio group (having carbon atoms preferably in the range of 6 to 30, more preferably in the range of 6 to 20, and particularly preferably in the range of 6 to 12; for example, phenylthio), a heterocyclic thio group (having carbon atoms preferably in the range of 1 to 30, more preferably in the range of 1 to 20, and particularly preferably in the range of 1 to 12; for example, pyridylthio, 2-benzimidazolylthio, 2-benzoxazolylthio, 2-benzthiazolylthio), a thiocarbonyl group (for example, thioketone group, thioester group), and a thioether group (for example, dialkylthioether group, diarylthioether group, thiofuryl group).

Examples of the atomic group to coordinate to $M^{X1}$ via a phosphorus atom include a dialkylphosphino group, a diarylphosphino group, a trialkylphosphine, a triarylphosphine, a phosphinine group. These groups may be further substituted.

As the atomic group represented by $Q^{X11}$, $Q^{X12}$, $Q^{X13}$, $Q^{X14}$, $Q^{X15}$, or $Q^{X16}$, preferred are an aromatic hydrocarbon ring group to coordinate via a carbon atom, an aromatic heterocycle group to coordinate via a carbon atom, a nitrogen-containing aromatic heterocycle group to coordinate via a nitrogen atom, an alkyloxy group, an aryloxy group, an alkylthio group, an arylthio group, a dialkylphosphino group; more preferred are an aromatic hydrocarbon ring group to coordinate via a carbon atom, an aromatic heterocycle group to coordinate via a carbon atom, and a nitrogen-containing aromatic heterocycle group.

$L^{X11}$, $L^{X12}$, $L^{X13}$, and $L^{X14}$ each represent a single bond, a double bond, or a linking group. The linking group is not particularly restricted. Preferred examples of the linking group include a linking group comprising any of carbon, nitrogen, oxygen, sulfur, and silicon atoms. Specific examples of the linking group are shown below, but the present invention is not limited to these.

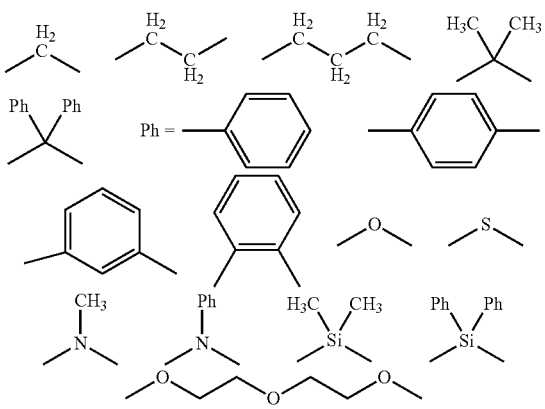

These linking groups may be further substituted by a substituent. Examples of the substituent include those explained as the substituents represented by $R^{21}$ to $R^{24}$ in formula (2), with the same preferable range. As $L^{X11}$, $L^{X12}$, $L^{X13}$ or $L^{X14}$, preferred are a single bond, a dimethylmethylene group, a dimethylsilylene group.

The metal complex represented by formula (X1) is more preferably a metal complex represented by formula (X2). Next, the metal complex represented by formula (X2) will be described below.

$M^{X2}$ has the same meaning as that of the aforementioned $M^{X1}$ in formula (X1), with the same preferable range. $Y^{X21}$, $Y^{X2}$, $Y^{X23}$, $Y^{X24}$, $Y^{X25}$, and $Y^{X26}$ each represent an atom to coordinate to $M^{X2}$. A bond between $Y^{X21}$ and $M^{X2}$, a bond between $Y^{X22}$ and $M^{X2}$, a bond between $Y^{X23}$ and $M^{X2}$, a bond between $Y^{X24}$ and $M^{X2}$, a bond between $Y^{X25}$ and $M^{X2}$, and a bond between $Y^{X26}$ and $M^{X2}$ may each be a coordinate bond or a covalent bond. Specific examples of $T^{X21}$, $Y^{X22}$, $Y^{X23}$, $Y^{X24}$, $Y^{X25}$, or $Y^{X26}$ include a carbon atom, a nitrogen atom, an oxygen atom, a sulfur atom, a phosphorus atom, and a silicon atom; and preferred are a carbon atom and a nitrogen atom. Each of $Q^{X21}$, $Q^{X22}$, $Q^{X23}$, $Q^{X24}$, $Q^{X25}$, and $Q^{X26}$ respectively represents an atomic group necessary to form an aromatic hydrocarbon ring or aromatic heterocycle together with each of $Y^{X21}$, $Y^{X22}$, $Y^{X23}$, $Y^{X24}$, $Y^{X25}$, and $Y^{X26}$, respectively. Examples of the aromatic hydrocarbon ring or aromatic heterocycle formed by these groups include benzene, pyridine, pyrazine, pyrimidine, pyridazine, triazine, pyrrole, pyrazole, imidazole, triazole, oxazole, thiazole, oxadiazole, thiadiazole, thiophene, and furane rings. Preferred are benzene, pyridine, pyrazine, pyrimidine, pyrazole, imidazole, and triazole rings; more preferred are benzene, pyridine, pyrazine, pyrazole, and triazole rings; and particularly preferred are benzene and pyridine rings. These rings may further include a condensed ring, or may have a substituent.

$L^{X21}$, $L^{X22}$, $L^{X23}$, and $L^{X24}$ have the same meanings as those of the aforementioned $L^{X11}$, $L^{X12}$, $L^{X13}$, and $L^{X14}$ in formula (X1), with the same preferable ranges.

The metal complex represented by formula (X1) is furthermore preferably a metal complex represented by formula (X3). Next, the metal complex represented by formula (X3) will be described below.

$M^{X3}$ has the same meaning as that of the aforementioned $M^{X1}$ in formula (X1), with the same preferable range. $Y^{X31}$, $Y^{X32}$, $Y^{X33}$, $Y^{X34}$, $Y^{X35}$, and $Y^{X36}$ each represent an atom to coordinate to $M^{X3}$. A bond between $Y^{X31}$ and $M^{X3}$, a bond between $Y^{X32}$ and $M^{X3}$, a bond between $Y^{X33}$ and $M^{X3}$, a bond between $Y^{X34}$ and $N^{X3}$, a bond between $Y^{X35}$ and $M^{X3}$, and a bond between $Y^{X36}$ and $M^{X3}$ may each be a coordinate bond or a covalent bond. Specific examples of $Y^{X31}$, $Y^{X32}$, $Y^{X33}$, $Y^{X34}$, $Y^{X35}$, or $Y^{X36}$ include a carbon atom, a nitrogen atom, and a phosphorus atom; and preferred are a carbon atom and a nitrogen atom. $L^{X31}$, $L^{X32}$, $L^{X33}$, and $L^{X34}$ have the same meanings as those of the aforementioned $L^{X11}$, $L^{X12}$, $L^{X13}$, and $L^{X14}$ in formula (X1), with the same preferable ranges.

Specific examples of the compound of the present invention are shown below, but the present invention is not limited to these compounds.

Compound (1)

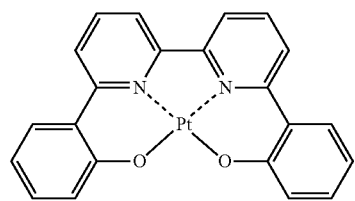

Compound (2)

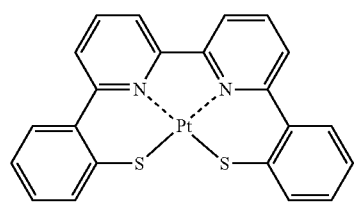

Compound (3)

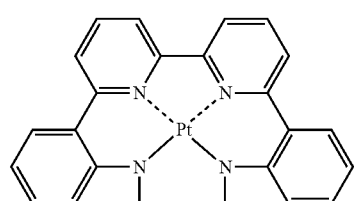

Compound (4)

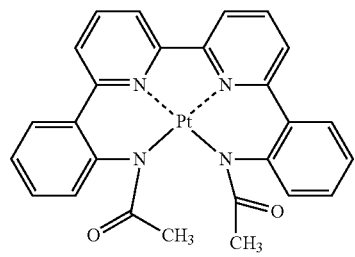

Compound (5)

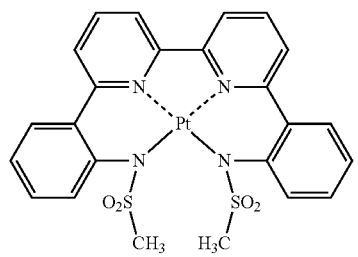

Compound (6)

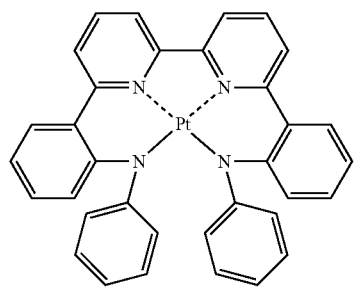

Compound (7)

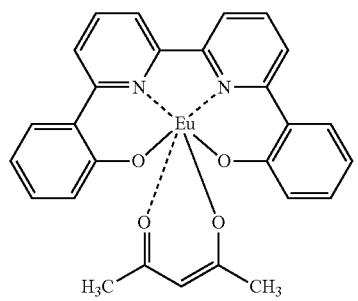

Compound (8)

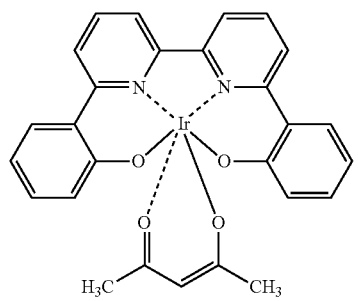

Compound (9)

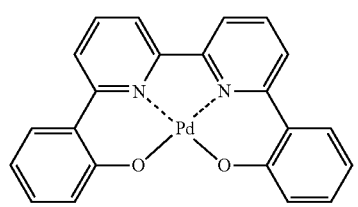

Compound (10)
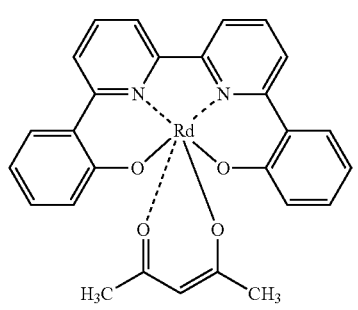
Compound (11)
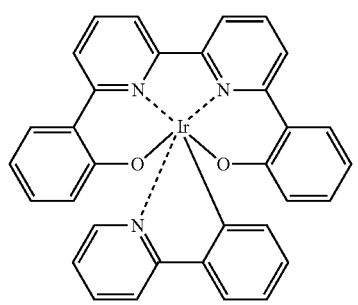
Compound (12)
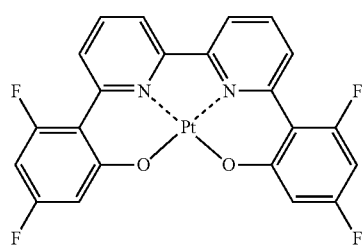
Compound (13)
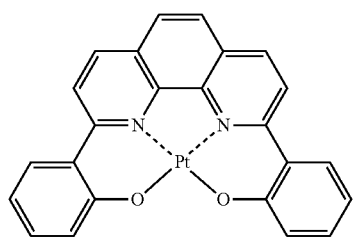
Compound (14)
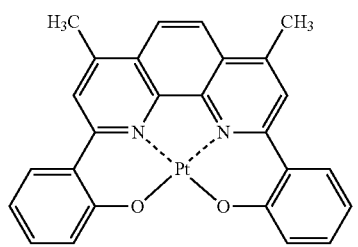
Compound (15)
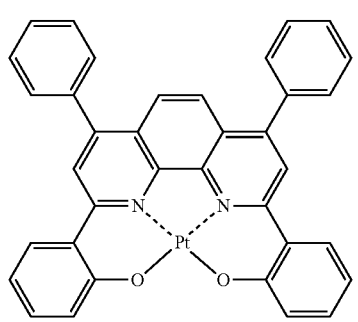
Compound (16)
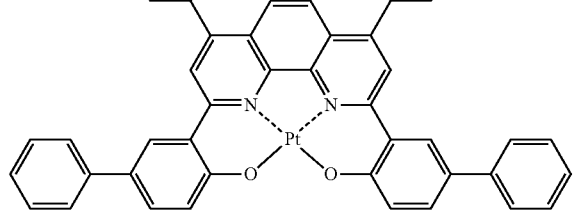
Compound (17)
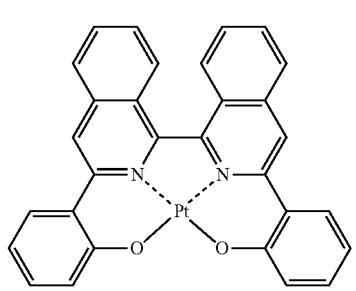
Compound (18)
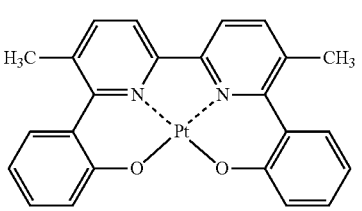
Compound (19)
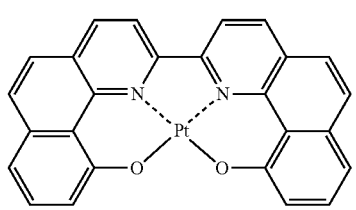
Compound (20)
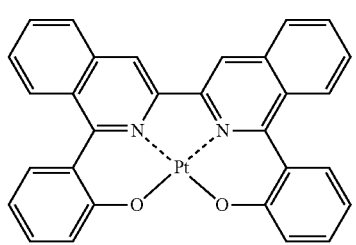
Compound (21)
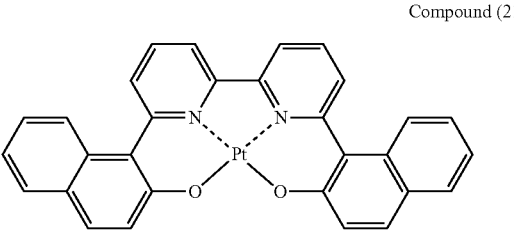

-continued
Compound (22)
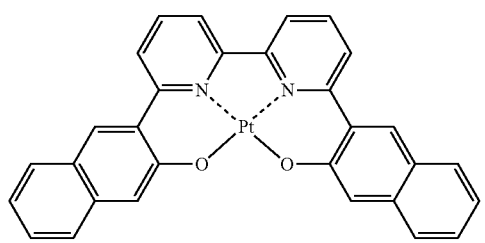
Compound (23)
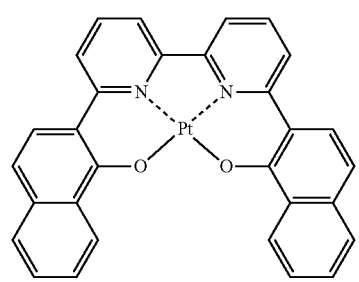
Compound (24)
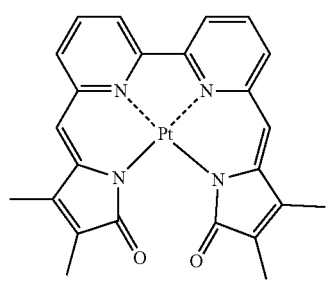
Compound (25)
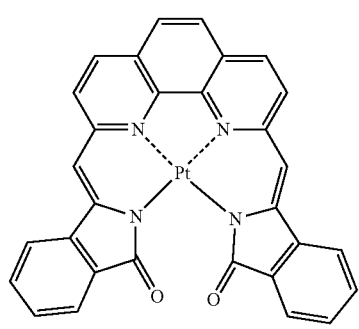
Compound (26)
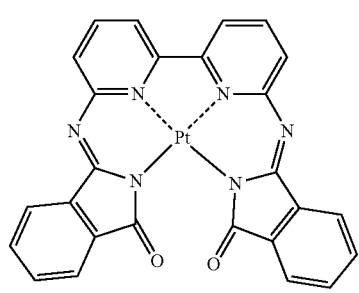
Compound (27)
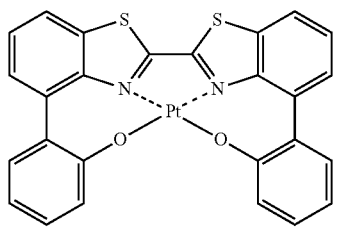
Compound (28)
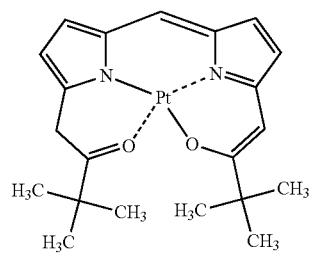
Compound (29)
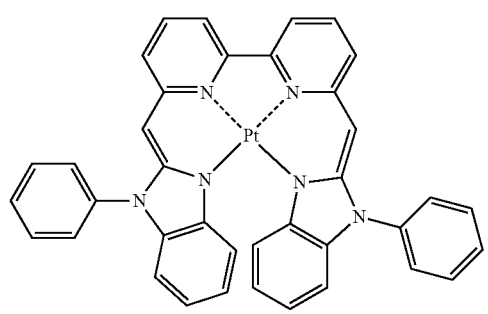
Compound (30)
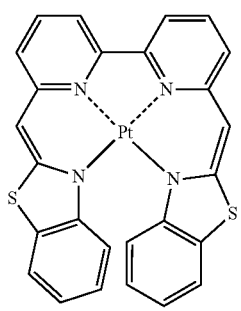
Compound (31)
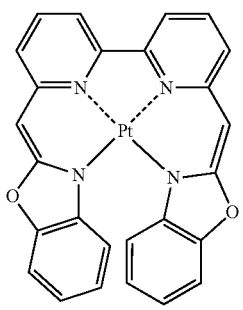

Compound (32)
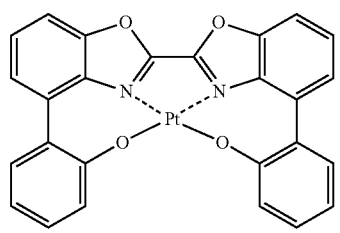
Compound (33)
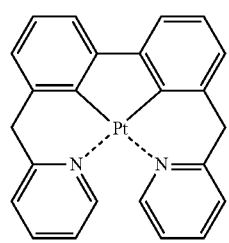
Compound (34)
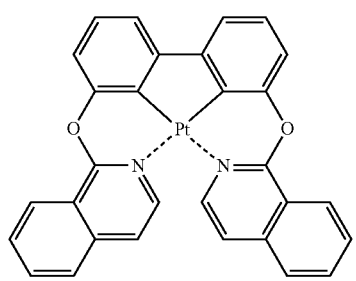
Compound (35)
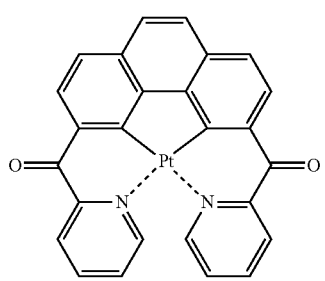
Compound (36)
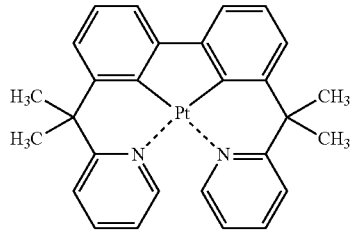
Compound (37)
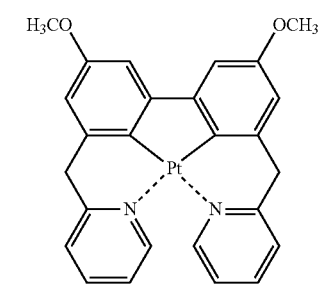
Compound (38)
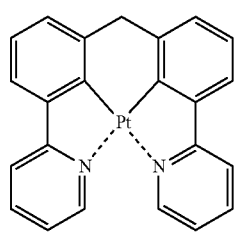
Compound (39)
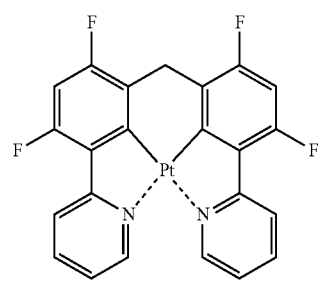
Compound (40)
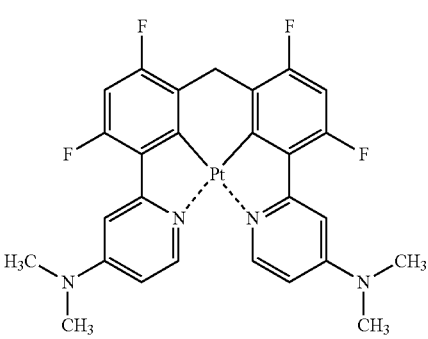
Compound (41)
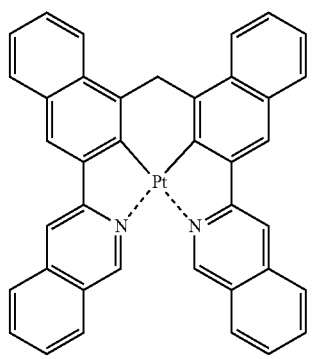
Compound (42)
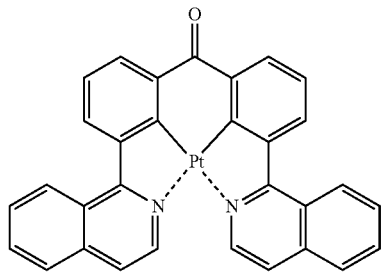

Compound (43)
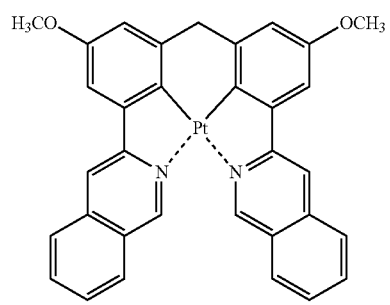
Compound (44)
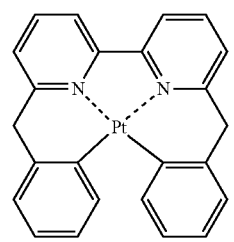
Compound (45)
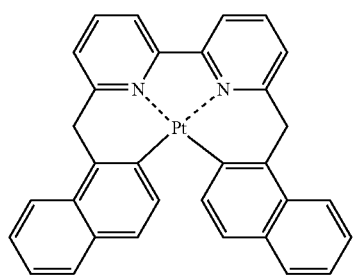
Compound (46)
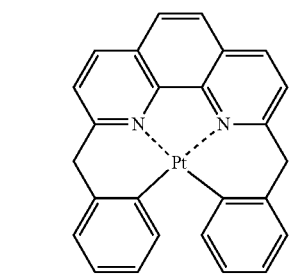
Compound (47)
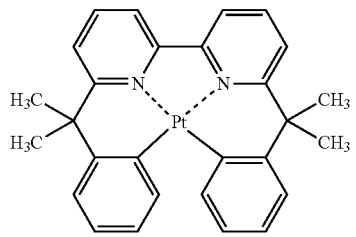
Compound (48)
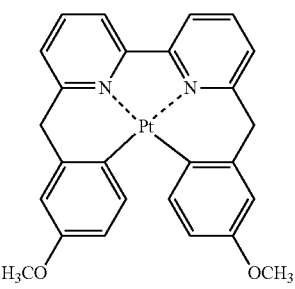
Compound (49)
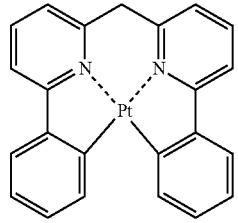
Compound (50)
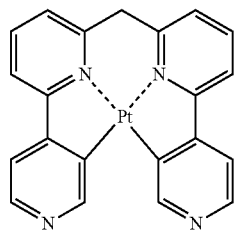
Compound (51)
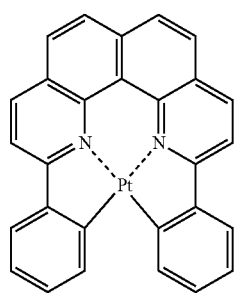
Compound (52)
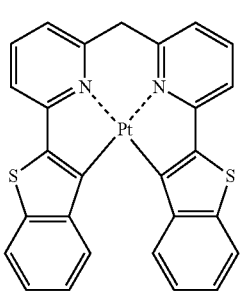
Compound (53)
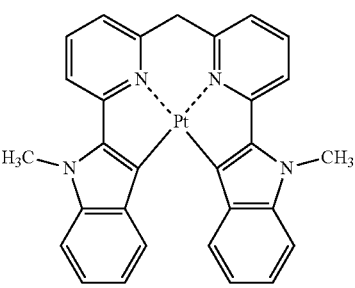
Compound (54)
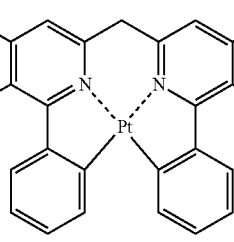

-continued
Compound (55)
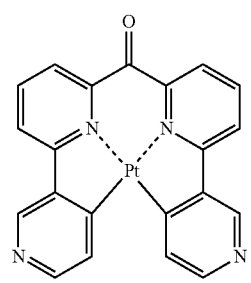
Compound (56)
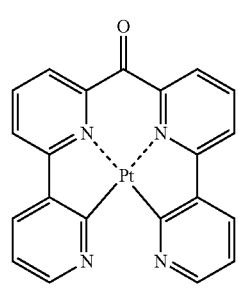
Compound (57)
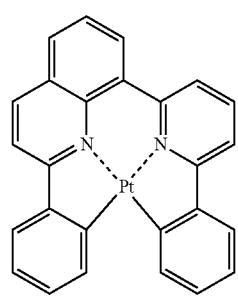
Compound (58)
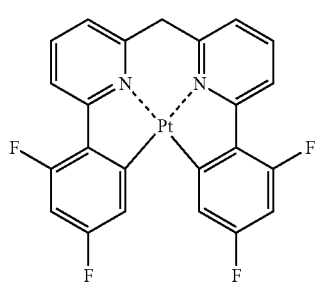
Compound (59)
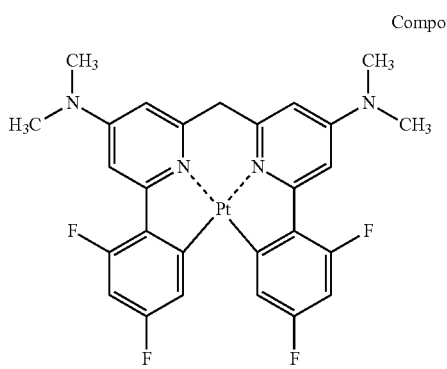
-continued
Compound (60)
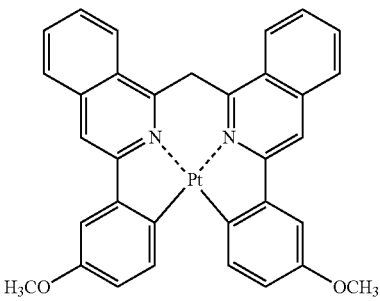
Compound (61)
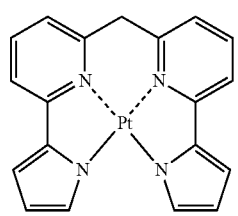
Compound (62)
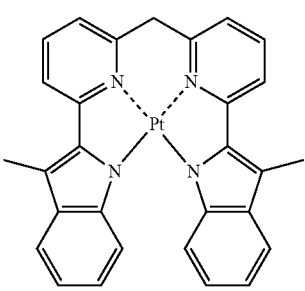
Compound (63)
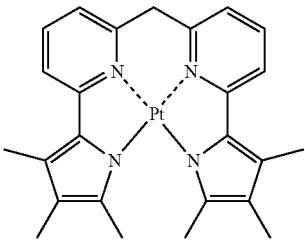
Compound (64)
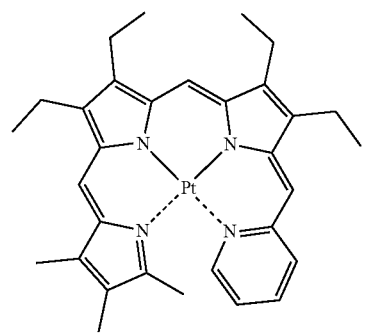

Compound (65)
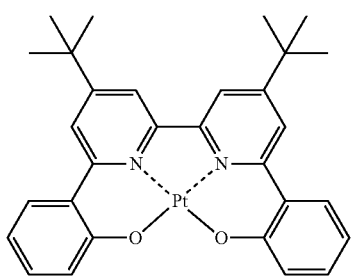
Compound (66)
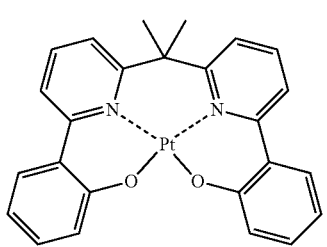
Compound (67)
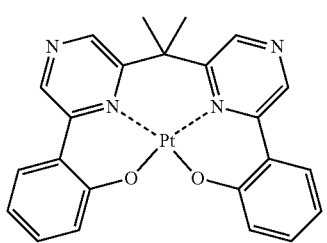
Compound (68)
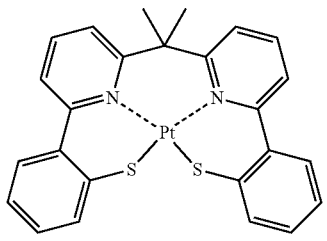
Compound (69)
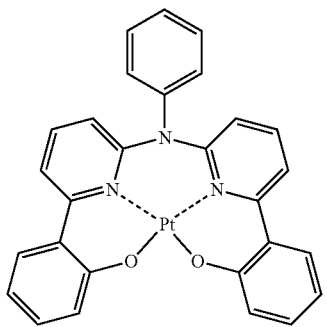
Compound (70)
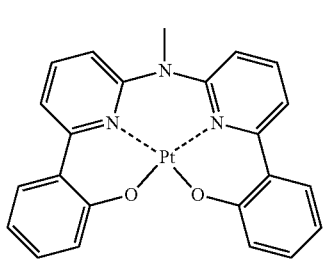
Compound (71)
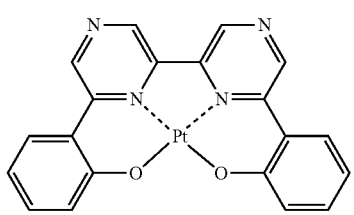
Compound (72)
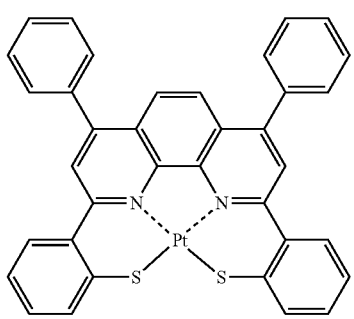
Compound (73)
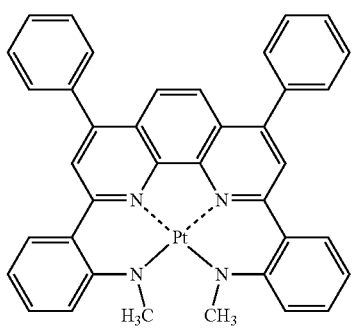
Compound (74)
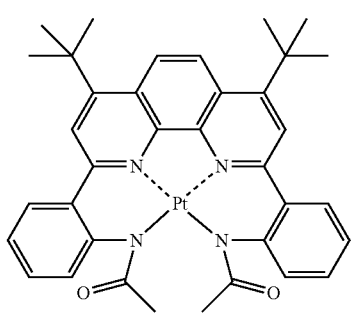
Compound (75)
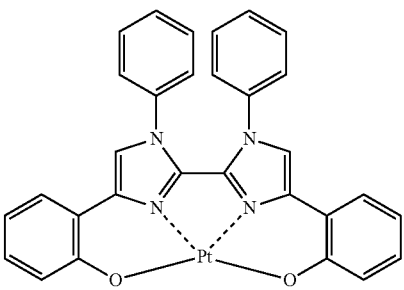

-continued
Compound (76)
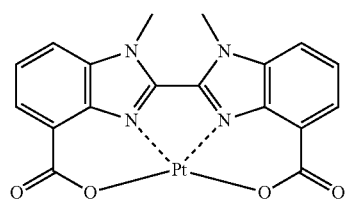
Compound (77)
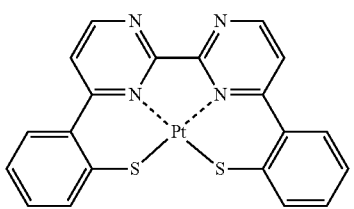
Compound (78)
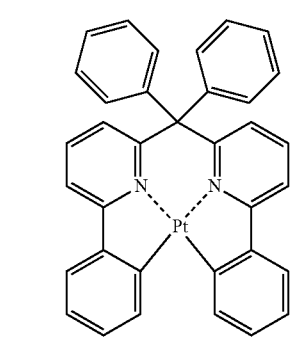
Compound (79)
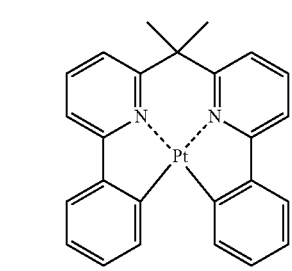
Compound (80)
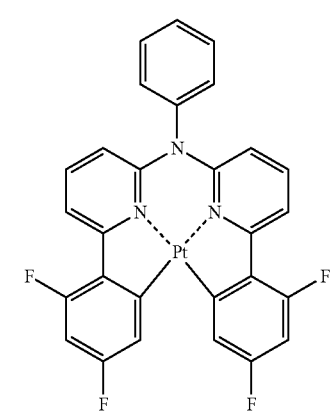
-continued
Compound (81)
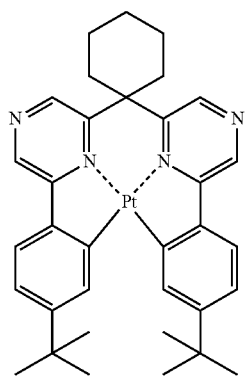
Compound (82)
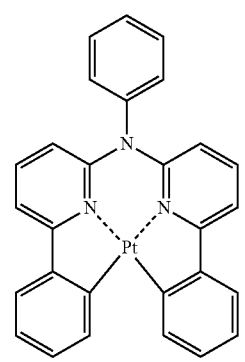
Compound (83)
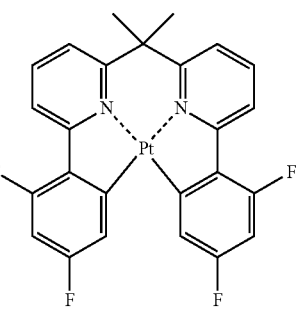
Compound (84)
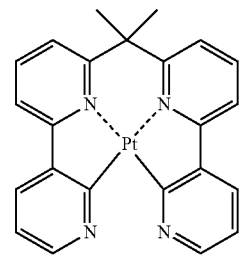
Compound (85)
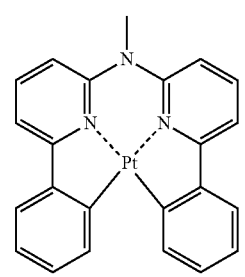

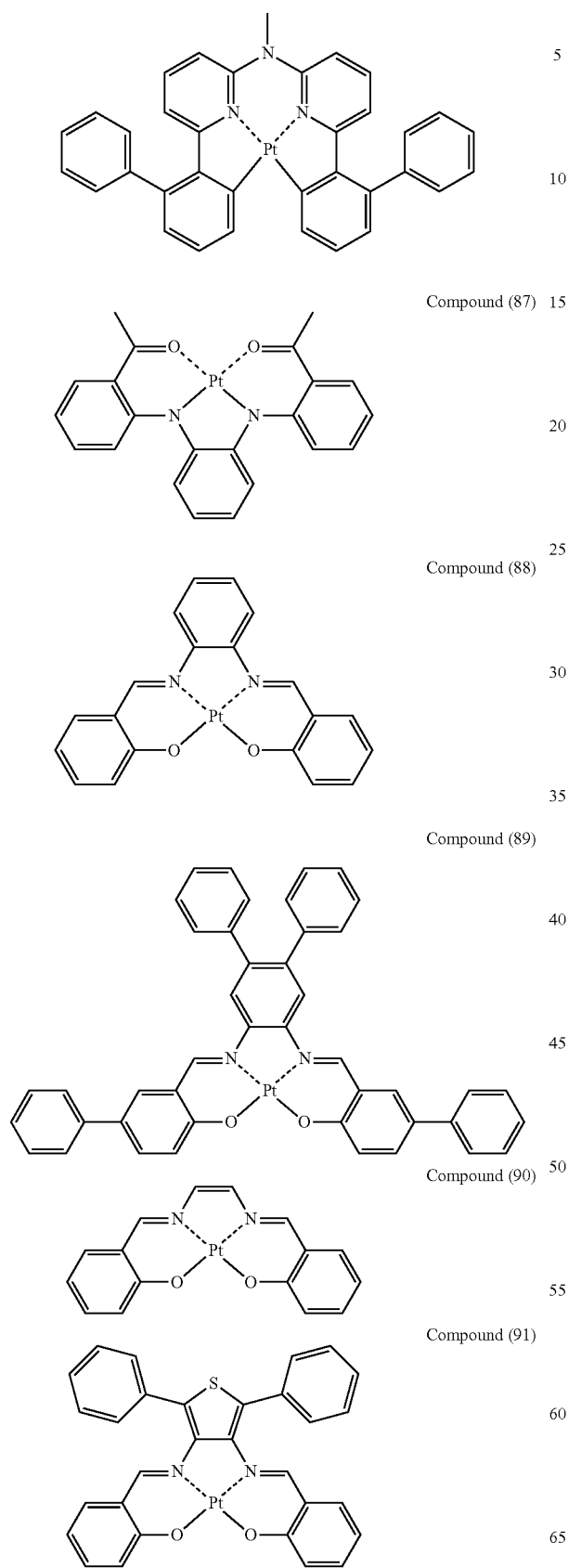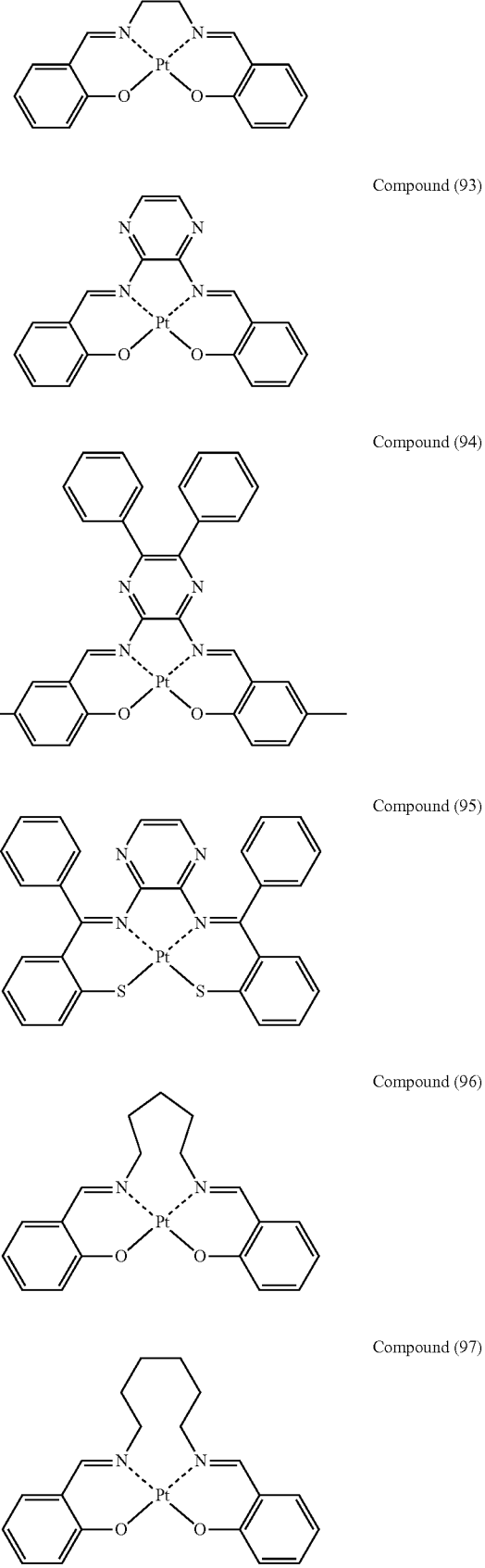

Compound (98)
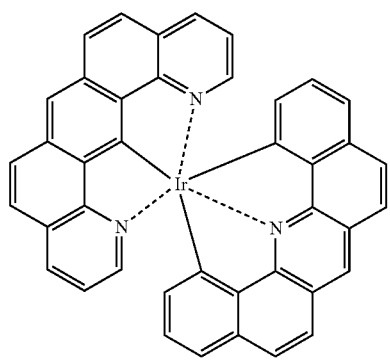
Compound (99)
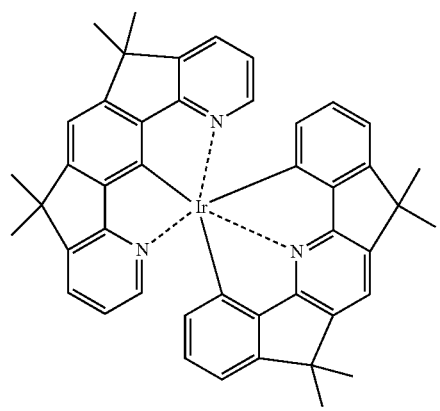
Compound (100)
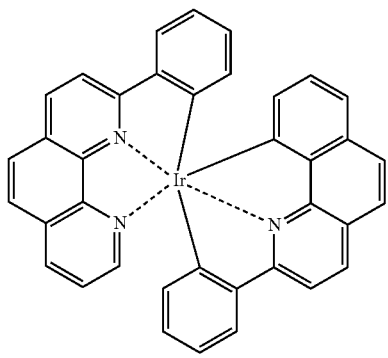
Compound (101)
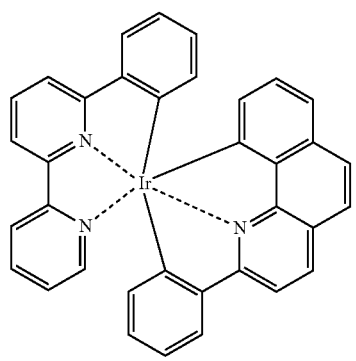
Compound (102)
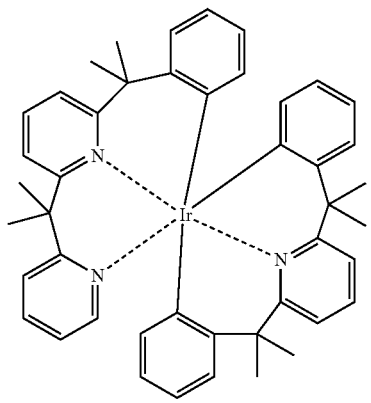
Compound (103)
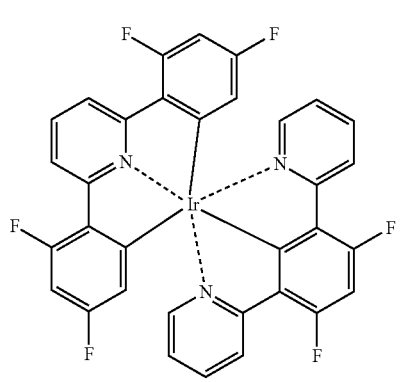
Compound (104)
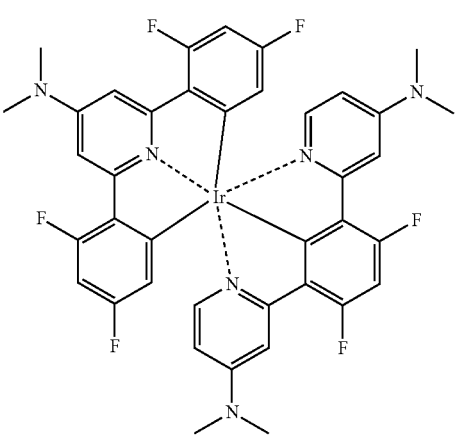
Compound (105)
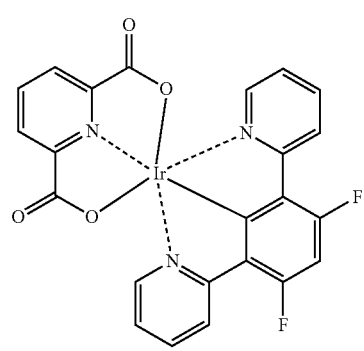

Compound (106)
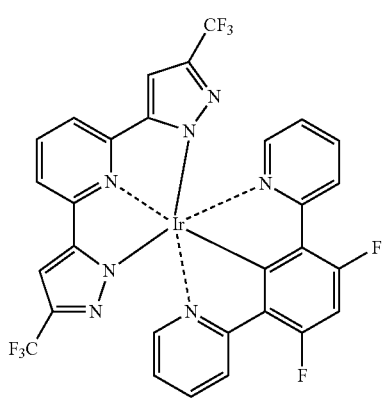
Compound (107)
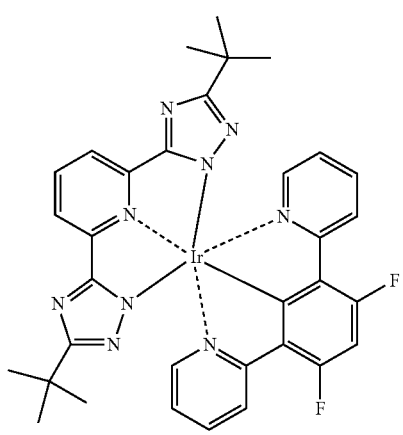
Compound (108)
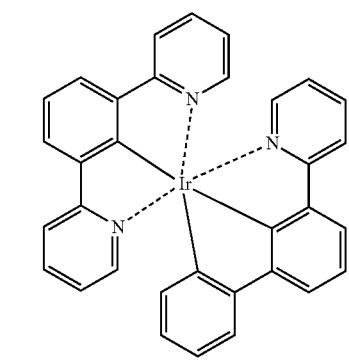
Compound (109)
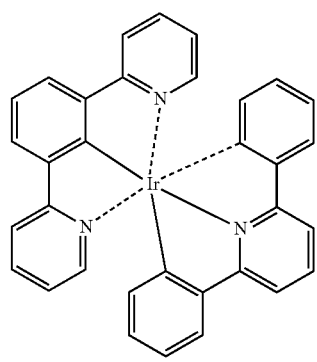
Compound (110)
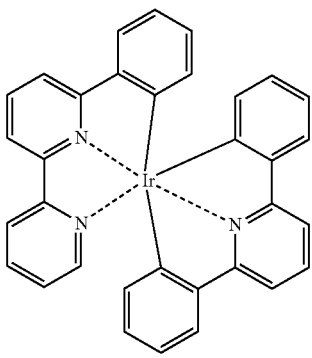
Compound (111)
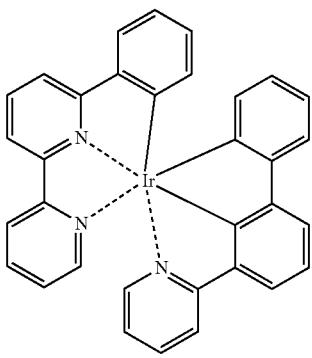
Compound (112)
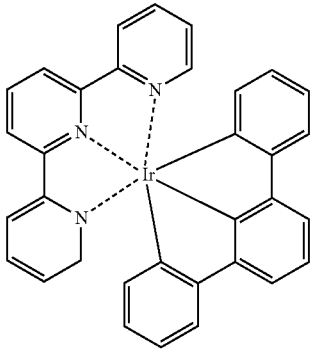
Compound (113)
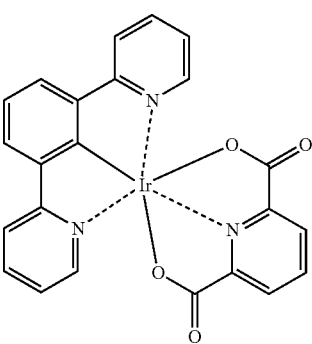

Compound (114)
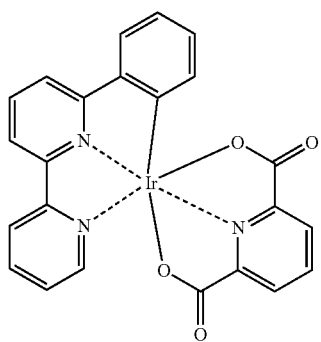
Compound (115)
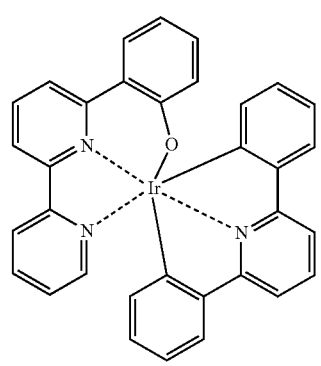
Compound (116)
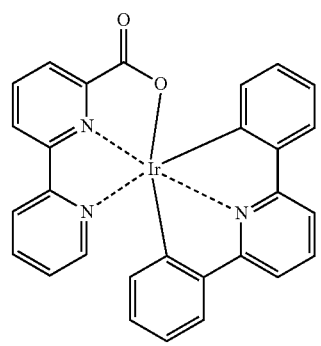
Compound (117)
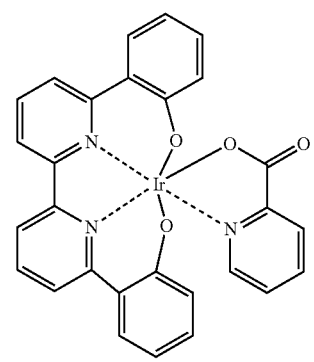
Compound (118)
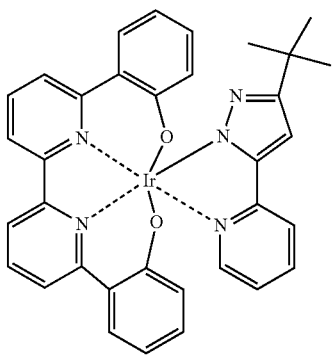
Compound (119)
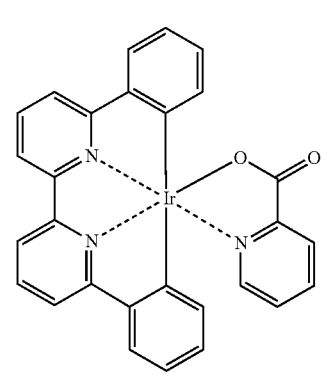
Compound (120)
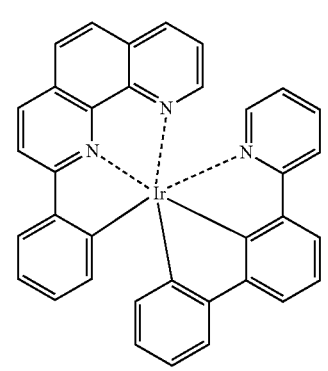
Compound (121)
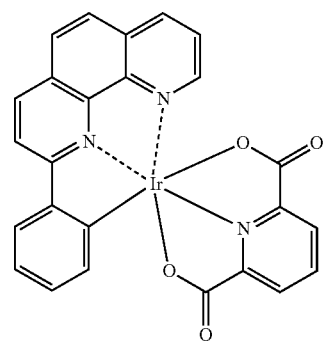

Compound (122)
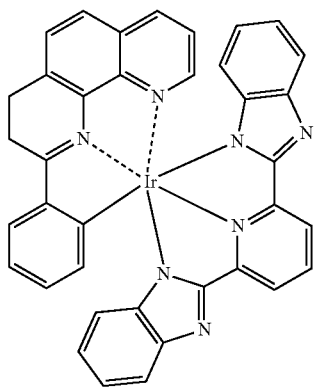
Compound (123)
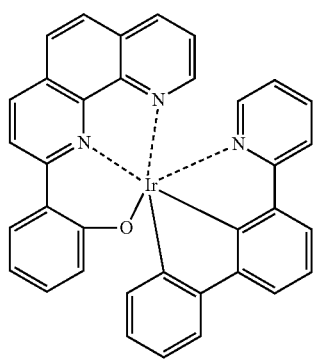
Compound (124)
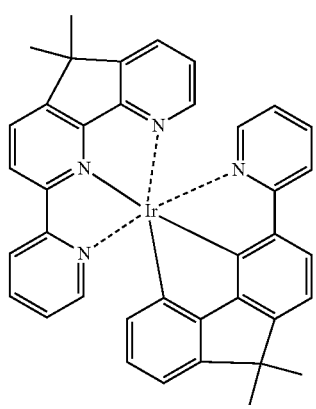
Compound (125)
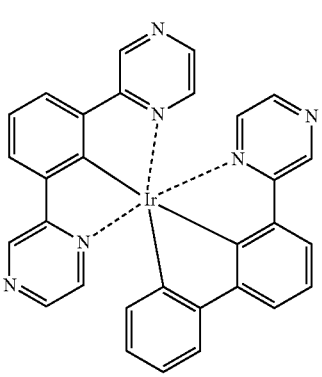
Compound (126)
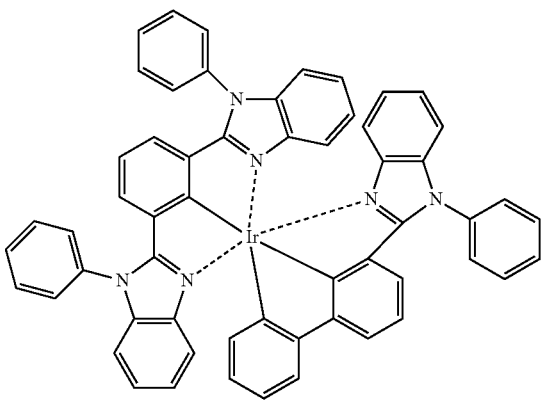
Compound (127)
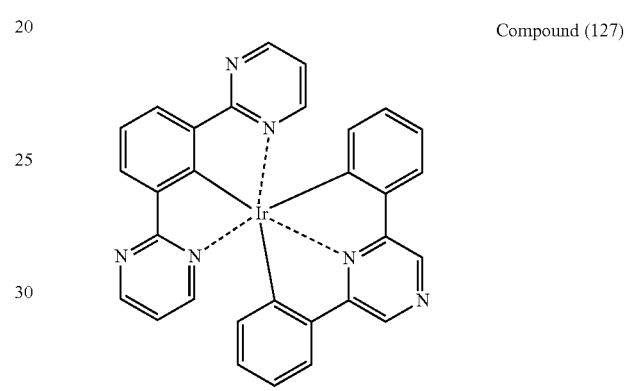
Compound (128)
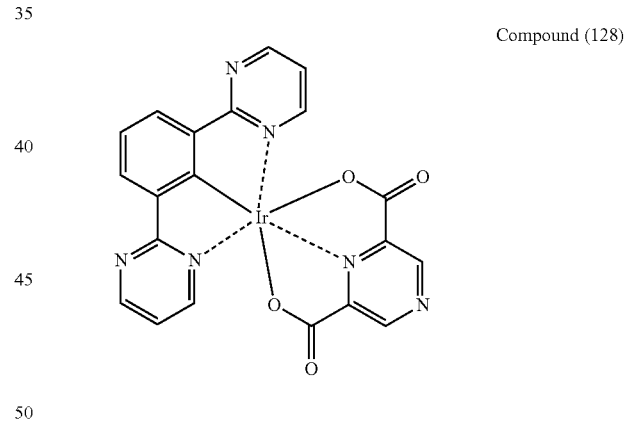
Compound (129)
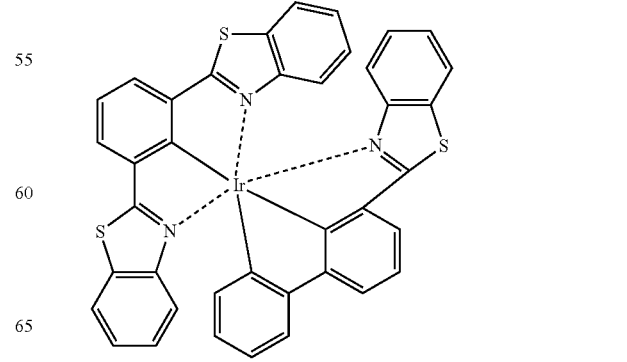

Compound (130)
Compound (131)
Compound (132)
Compound (133)
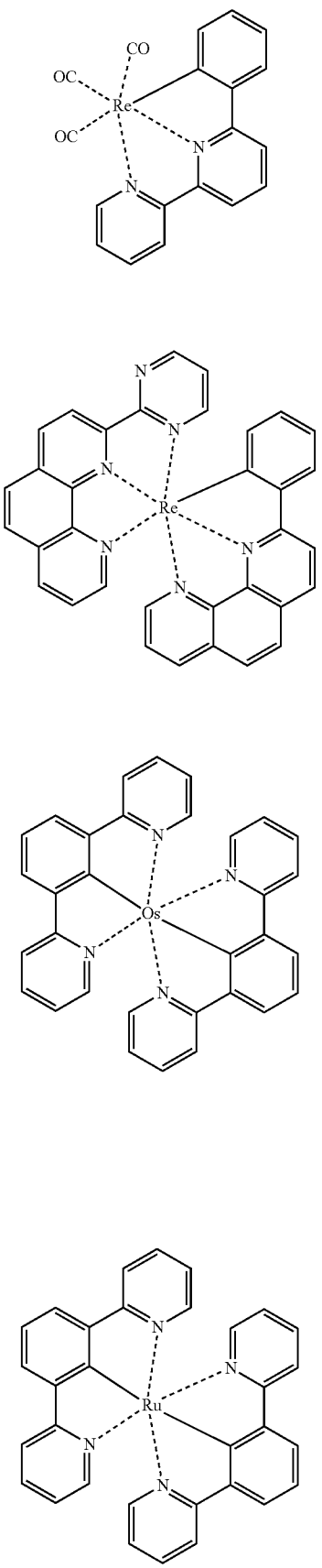
Compound (134)
Compound (135)
Compound (136)
Compound (137)
Compound (138)
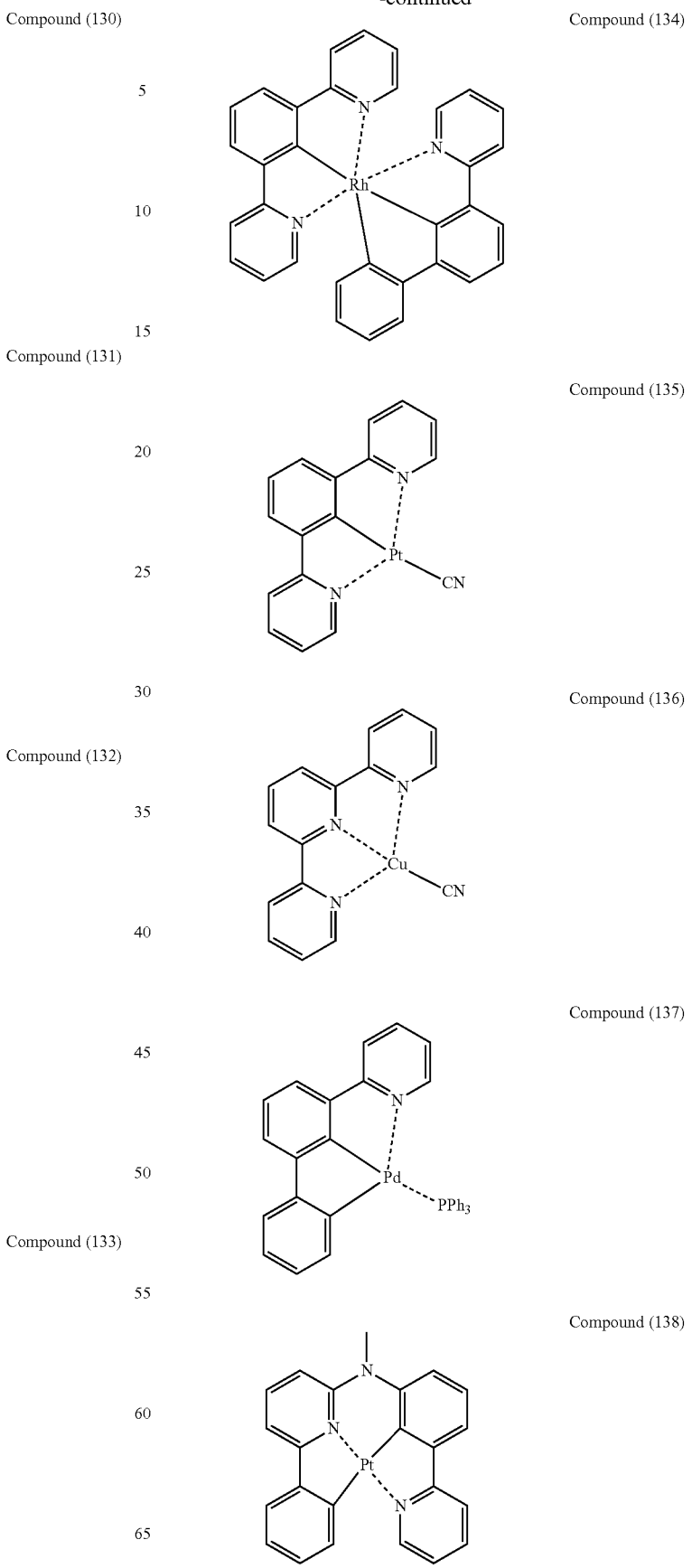

Compound (139)
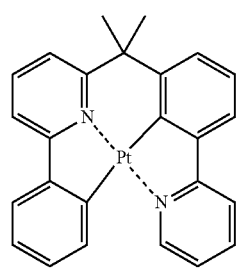
Compound (140)
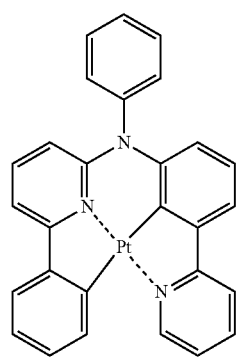
Compound (141)
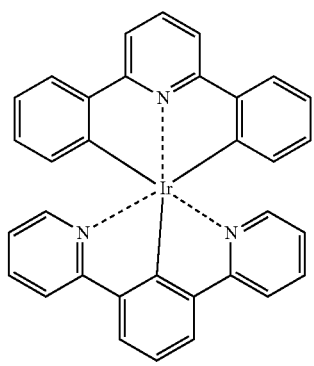
Compound (142)
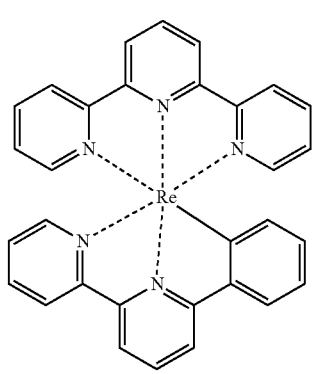
Compound (143)
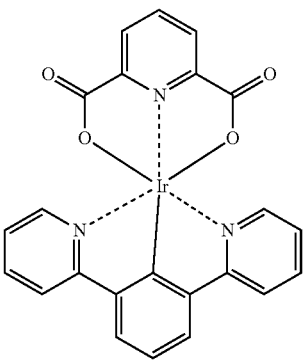
Compound (144)
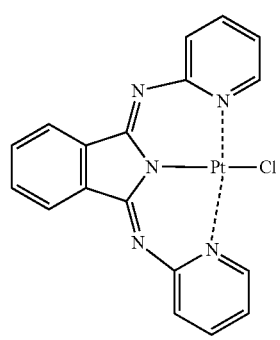
Compound (145)
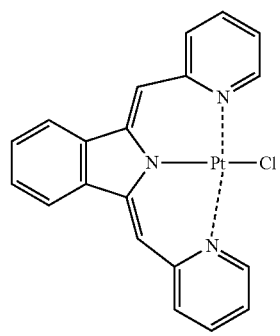
Compound (146)
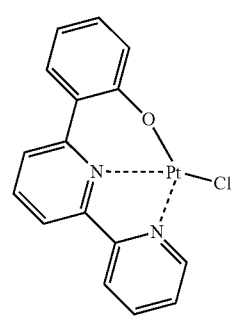

Compound (147)
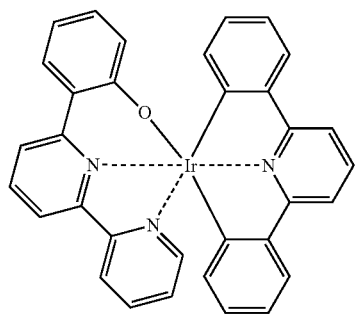
Compound (148)
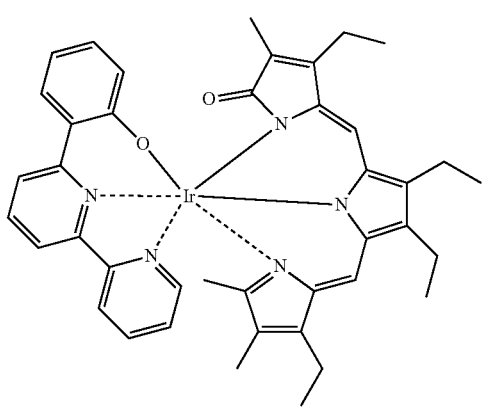
Compound (149)
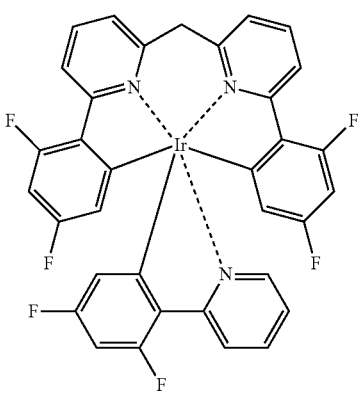
Compound (150)
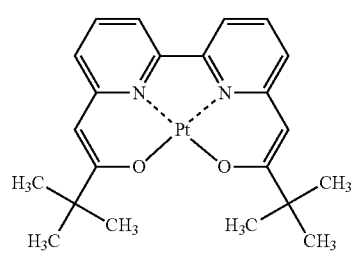
Compound (151)
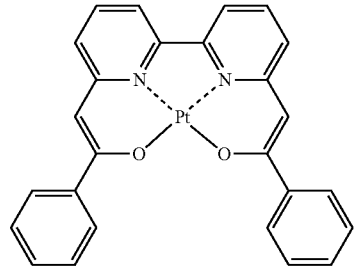
Compound (152)
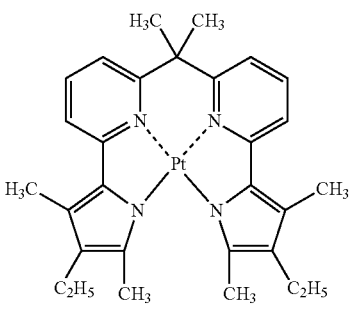
Compound (153)
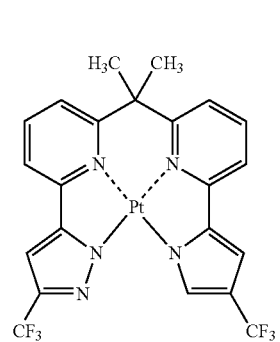
Compound (154)
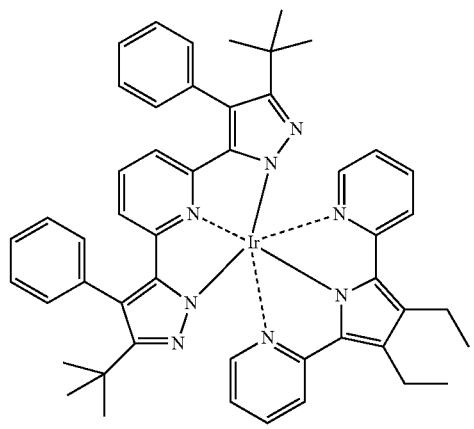
Compound (155)
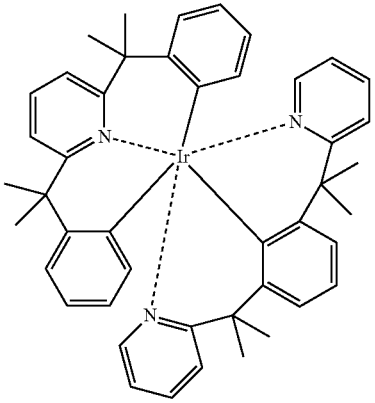

Compound (156)
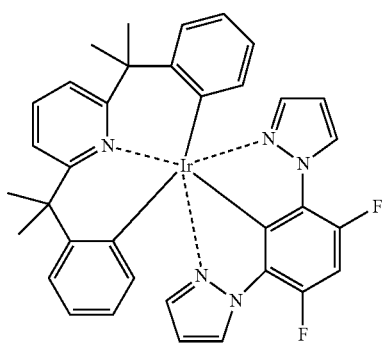
Compound (160)
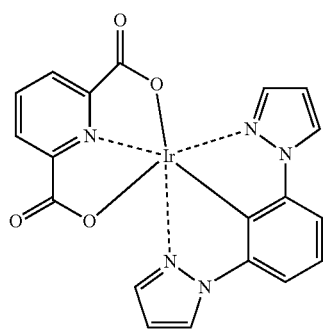
Compound (157)
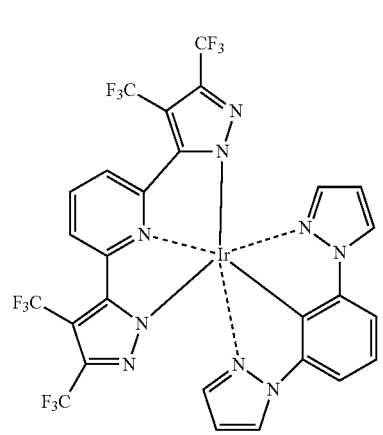
Compound (161)
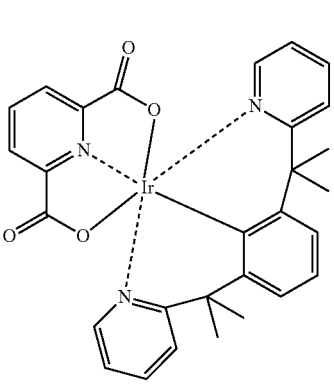
Compound (158)
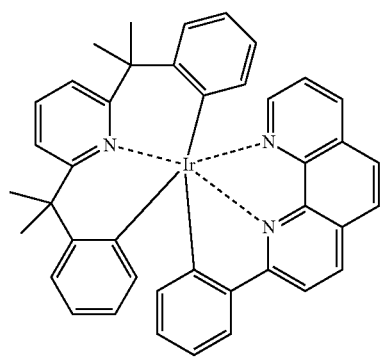
Compound (162)
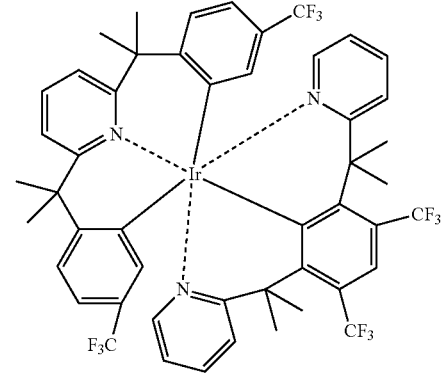
Compound (159)
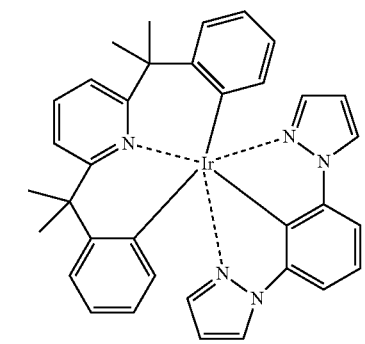
Compound (163)
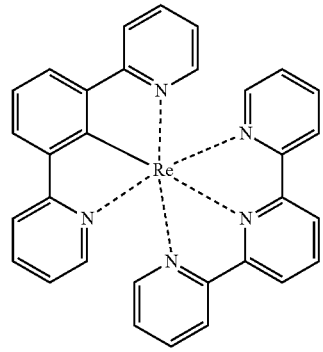

-continued
Compound (164)
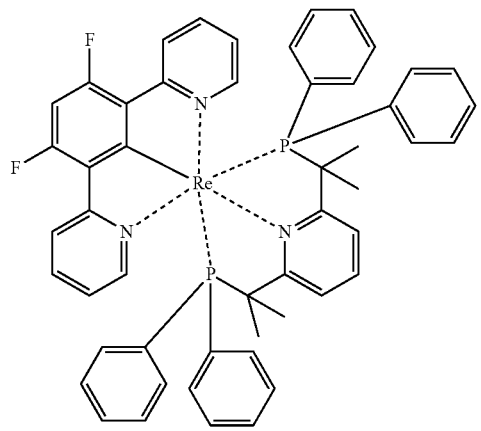
Compound (165)
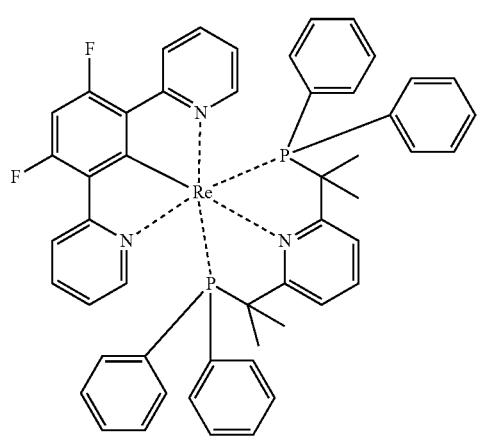
Compound (166)
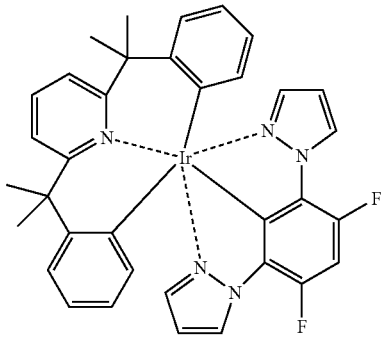
Compound (167)
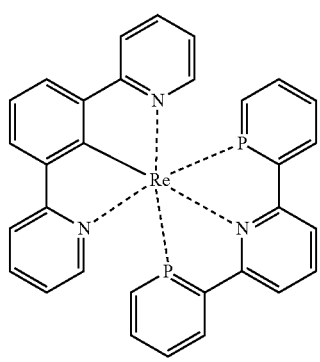
-continued
Compound (168)
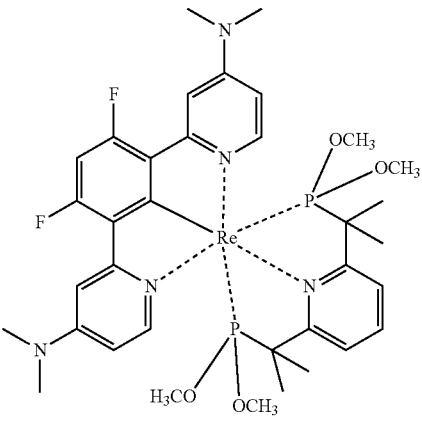
Compound (169)
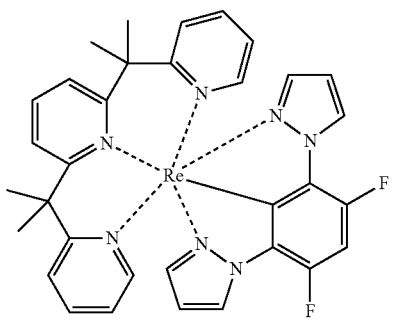
Compound (170)
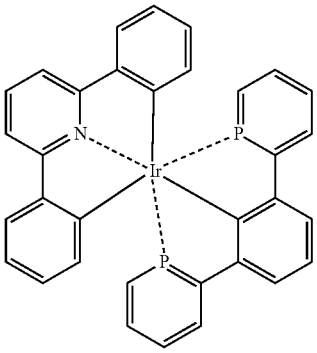
Compound (171)
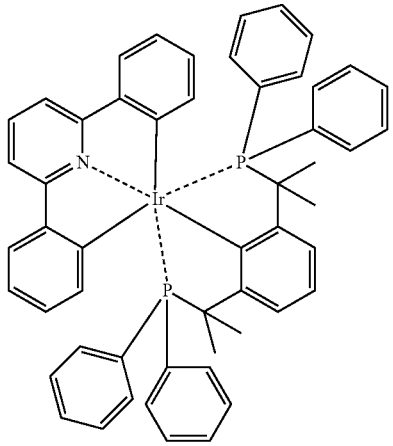

Compound (172)
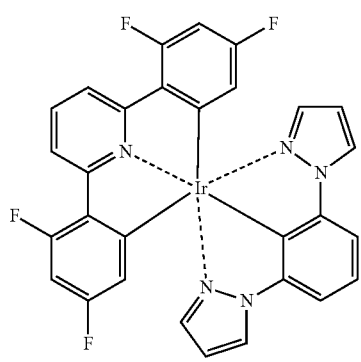
Compound (173)
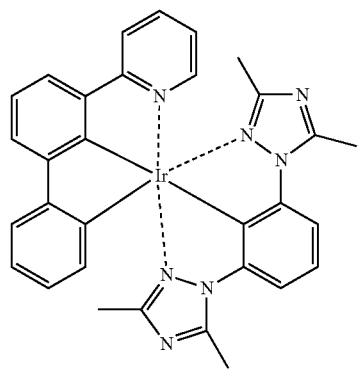
Compound (174)
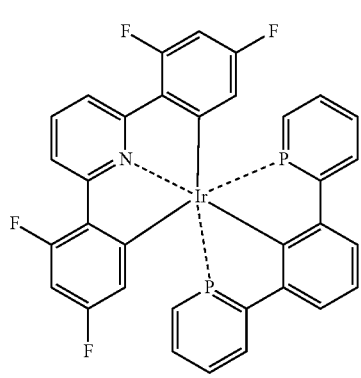
Compound (175)
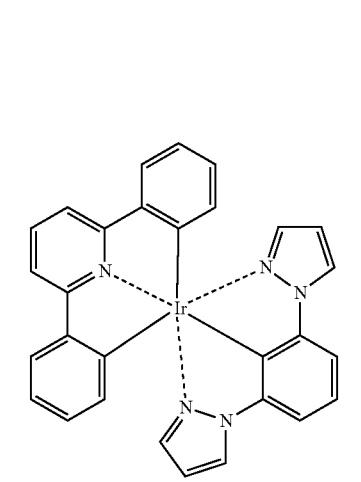
Compound (176)
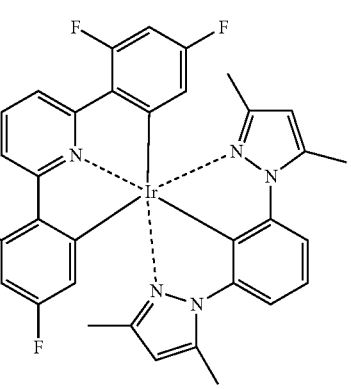
Compound (177)
Compound (178)
Compound (179)
Compound (180)
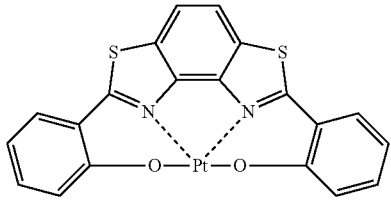

Compound (181)
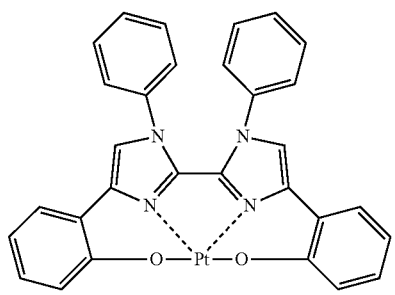
Compound (182)
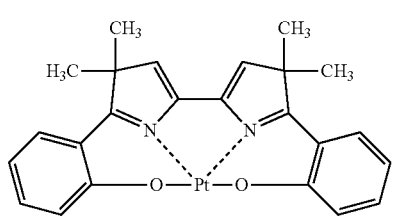
Compound (183)
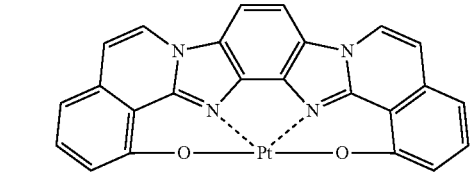
Compound (184)
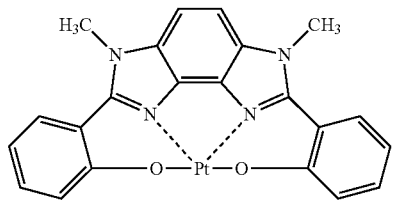
Compound (185)
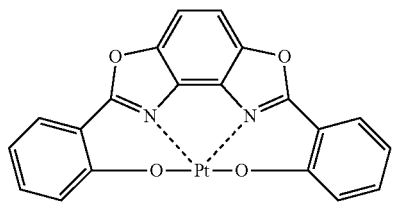
Compound (186)
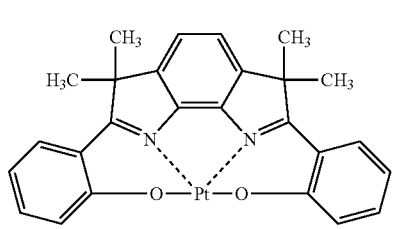
Compound (187)
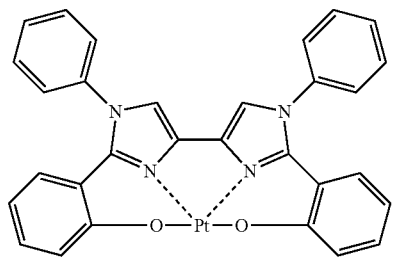
Compound (188)
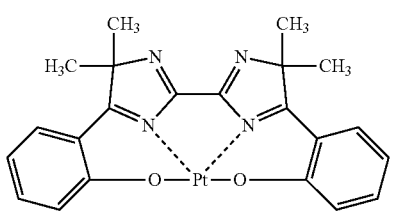
Compound (189)
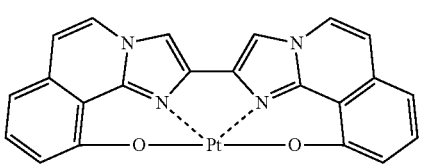
Compound (190)
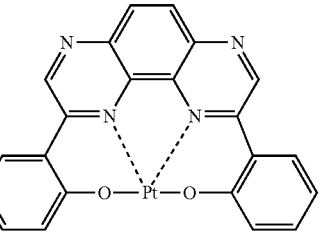
Compound (191)
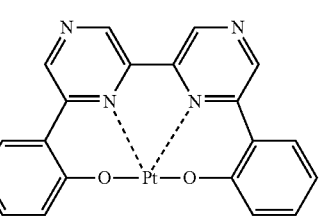
Compound (192)
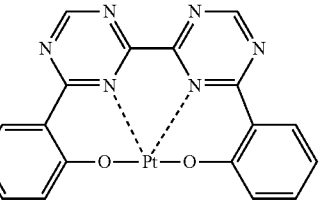
Compound (193)
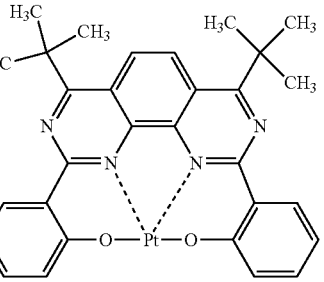
Compound (194)
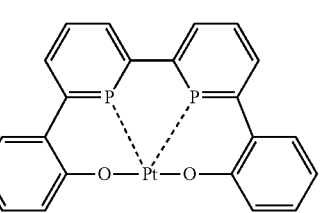

Compound (195)
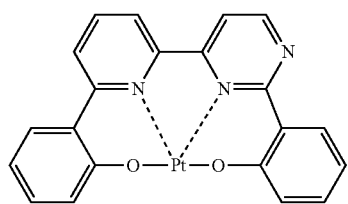
Compound (196)
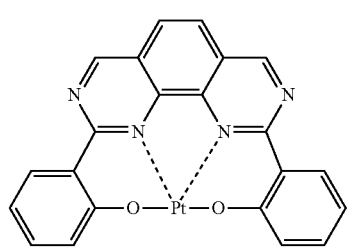
Compound (197)
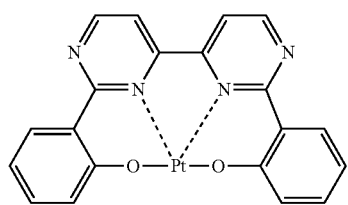
Compound (198)
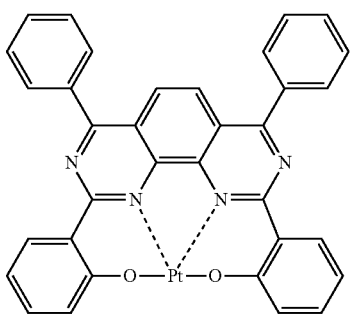
Compound (199)
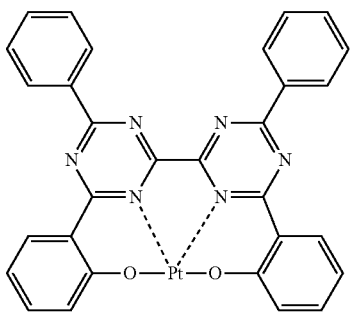
Compound (200)
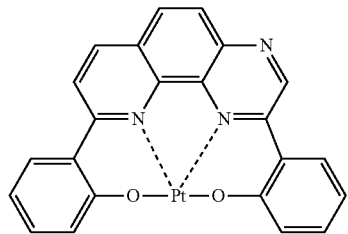
Compound (201)
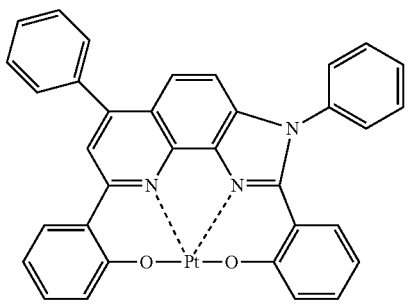
Compound (202)
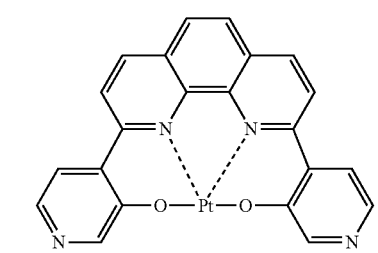
Compound (203)
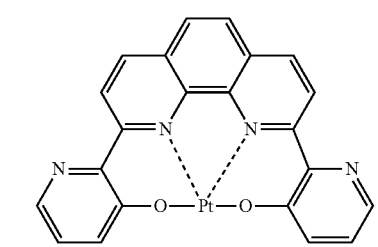
Compound (204)
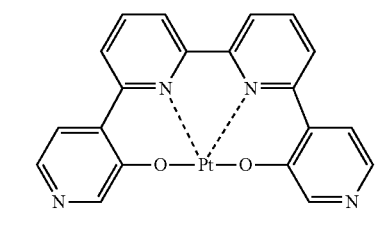
Compound (205)
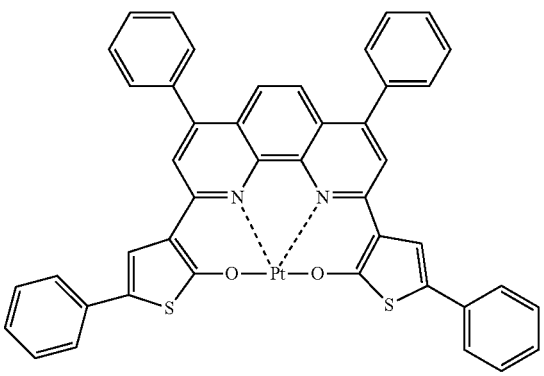

Compound (206)
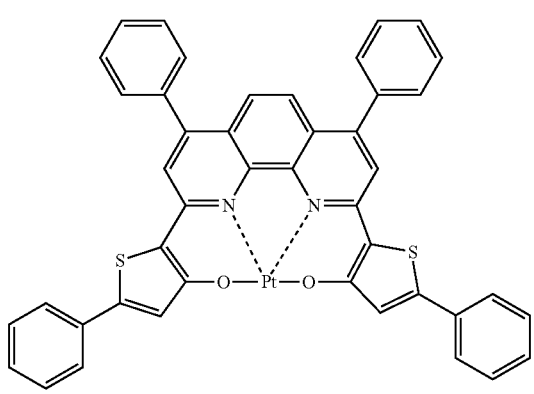
Compound (207)
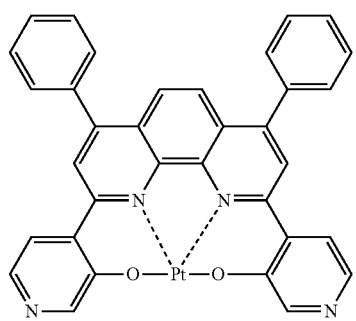
Compound (208)
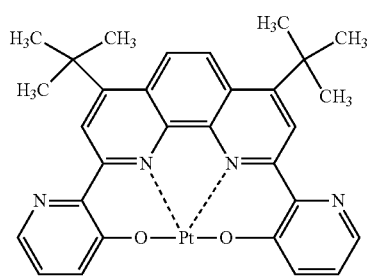
Compound (209)
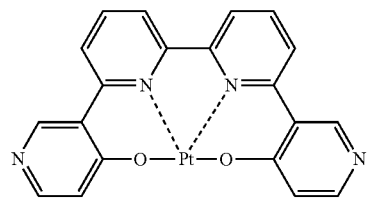
Compound (210)
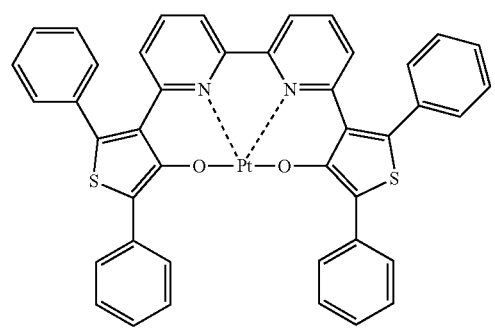
Compound (211)
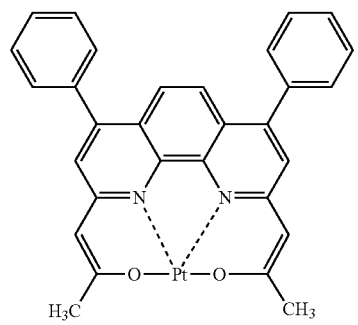
Compound (212)
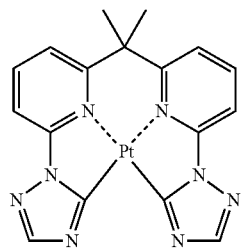
Compound (213)
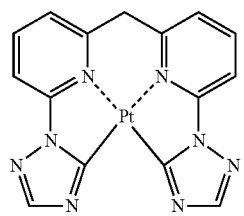
Compound (214)
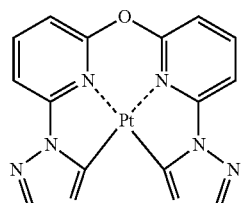
Compound (215)
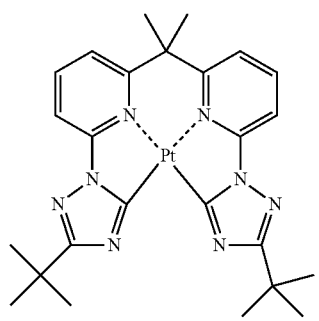
Compound (216)
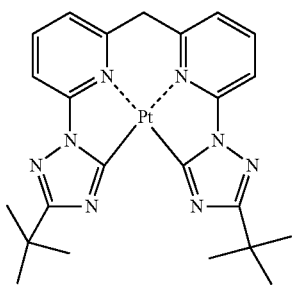

Compound (217)
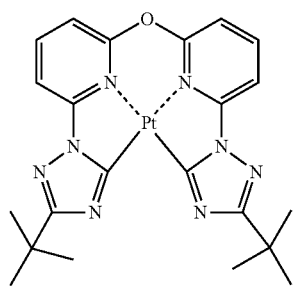
Compound (218)
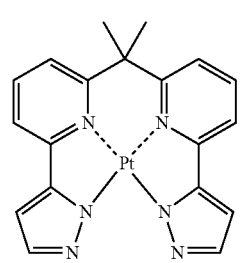
Compound (219)
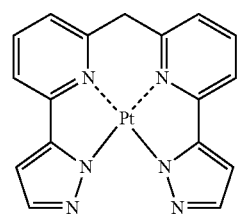
Compound (220)
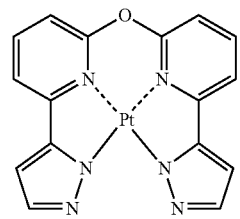
Compound (221)
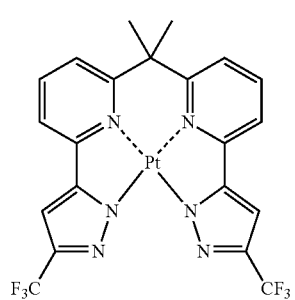
Compound (222)
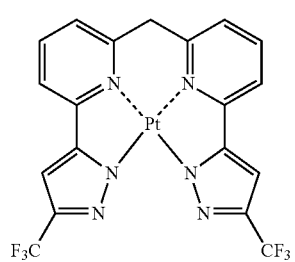
Compound (223)
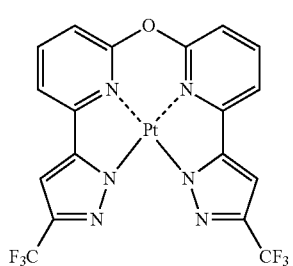
Compound (224)
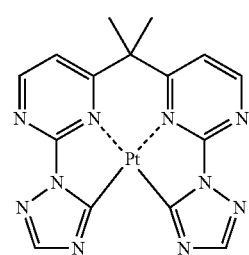
Compound (225)
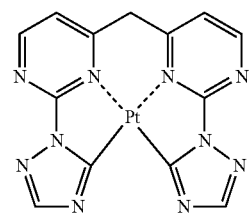
Compound (226)
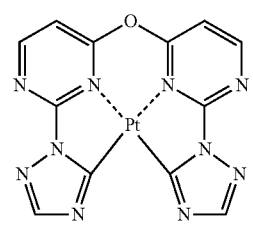
Compound (227)
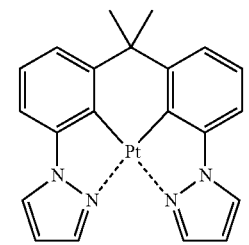
Compound (228)
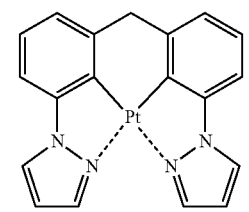

Compound (229)
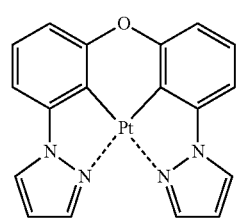
Compound (230)
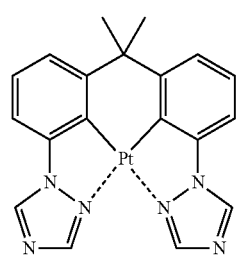
Compound (231)
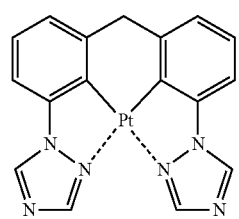
Compound (232)
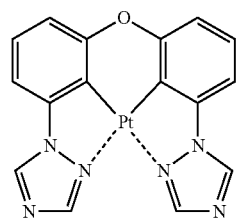
Compound (233)
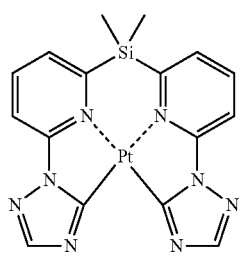
Compound (234)
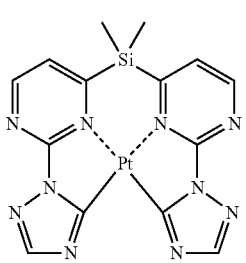
Compound (235)
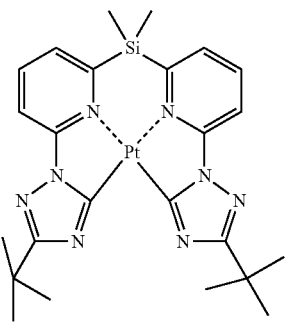
Compound (236)
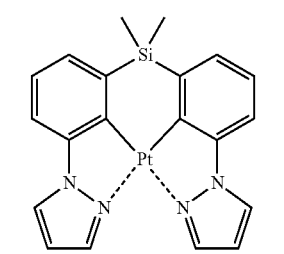
Compound (237)
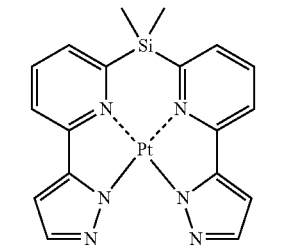
Compound (238)
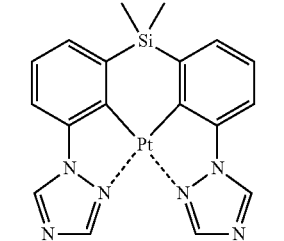
Compound (239)
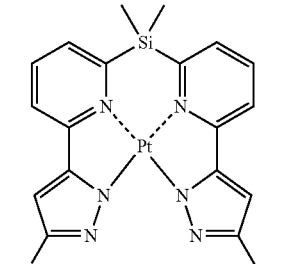
Compound (240)
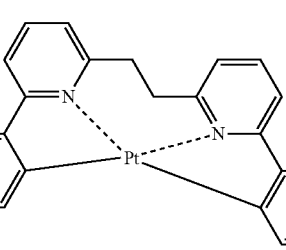

Compound (241)

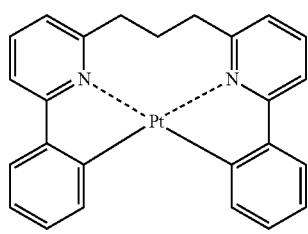

Compound (242)

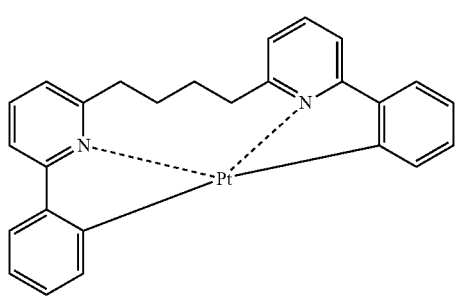

(Synthesis Methods of the Metal Complexes According to the Present Invention)

The metal complexes according to the present invention (i.e., compounds represented by any one of formulas (1) to (14) and formulas (X1) to (X3)) can be synthesized according to various methods.

For example, the compounds can be obtained by reacting a ligand or its dissociated product with a metal compound, in the presence of a solvent (e.g., a halogen-series solvent, an alcohol-series solvent, an ether-series solvent, an ester-series solvent, a ketone-series solvent, a nitrile-series solvent, an amide-series solvent, a sulfone-series solvent, a sulfoxide-series solvent and water), or in the absence of a solvent, in the presence of a base (various inorganic or organic bases, such as sodium methoxide, potassium t-butoxide, triethylamine and potassium carbonate), or in the absence of a base, at room temperature or below, or alternatively by heating (in addition to an ordinary heating, a method of heating by means of microwave is also effective).

A reaction time that is applied in synthesizing the metal complex of the present invention varies depending upon activity of raw materials, and there is no particular limitation as to the reaction time, but preferably the reaction time is in the range of from 1 minute to 5 days, more preferably in the range of from 5 minutes to 3 days, and furthermore preferably in the range of from 10 minutes to 1 day.

A reaction temperature that is applied in synthesizing the metal complex of the present invention varies depending upon reaction activity, and there is no particular limitation as to the reaction temperature, but the reaction temperature is preferably in the range of from 0° C. to 300° C., more preferably in the range of from 5° C. to 250° C., and furthermore preferably in the range of from 10° C. to 200° C.

The metal complexes of the present invention, such as the compounds represented by formulae (1) to (14) and formulae (X1) to (X3), can be synthesized by properly selecting a ligand that forms a partial structure of the objective complex. For example, the compounds represented by formula (3) can be synthesized by adding a ligand such as 6,6'-bis(2-hydroxyphenyl)-2,2'-bipyridyl or its derivatives (ligands such as 2,9-bis(2-hydroxyphenyl)-1,10-phenanthroline, 2,9-bis(2-hydroxyphenyl)-4,7-diphenyl-1,10-phenanthroline and 6,6'-bis(2-hydroxy-5-tert-butylphenyl)-2,2'-bipyridyl) in an amount of preferably from 0.1 to 10 equivalents, more preferably from 0.3 to 6 equivalents, furthermore preferably from 0.5 to 4 equivalents, to a metal compound, respectively. The reaction solvent, the reaction time and the reaction temperature that are used in the synthesis method of the compounds represented by formula (3) are each the same as described in the above-mentioned synthesis of the metal complexes of the present invention.

The derivatives of the 6,6'-bis(2-hydroxyphenyl)-2,2'-bipyridyl ligand can be synthesized according to various known methods. For example, they can be synthesized by subjecting 2,2'-bipyridyl derivatives (e.g., 1,10-phenanthroline) and anisole derivatives (e.g., 4-fluoroanisole) to a reaction according to the method described in Journal of Organic Chemistry, 741, 11 (1946). Alternatively, they can be synthesized by subjecting halogenated 2,2'-bipyridyl derivatives (e.g., 2,9-dibromo-1,10-phenanthroline) and 2-methoxyphenylboronic acid derivatives (e.g., 2-methoxy-5-fluorophenylboronic acid) as starting materials, to the Suzuki coupling reaction, followed by release of the methyl group as a protecting group according to, for example, the method described in Journal of organic Chemistry, 741, 11 (1946), or the method of heating the reaction mixture in the presence of pyridine hydrochloride. Alternatively, they can be synthesized by subjecting 2,2'-bipyridyl boronic acid derivatives (e.g., 6,6'-bis(4,4,5,5-tetramethyl-1,3,2-dioxaborolyl)-2,2'-bipyridyl) and halogenated anisole derivatives (e.g., 2-bromoanisole) as starting materials, to the Suzuki coupling reaction, followed by release of the methyl group as a protecting group according to, for example, the method described in Journal of Organic Chemistry, 741, 11 (1946), or the method of heating the reaction mixture in the presence of pyridine hydrochloride.

The luminescent devices containing the metal complex of the present invention are explained below.

The luminescent devices of the present invention are not particularly restricted, for example, in their system, driving method and form in use, so long as the metal complexes of the present invention are used therein. As a typical luminescent device, organic EL (electroluminescent) devices are recited.

The luminescent device of the present invention is an organic electroluminescent device comprising a pair of electrodes and at least one organic layer including a luminescent layer between the pair of electrodes. Said organic layer preferably contains a hole-transporting layer and a luminescent layer, and further at least one layer selected from an exciton-blocking layer, a hole injection layer, a hole-blocking layer and an electron-transporting layer.

The luminescent device of the present invention preferably has, between a negative electrode and a luminescent layer, a layer containing a compound having ionization potential of 5.9 eV or more (more preferably 6.0 eV or more), and more preferably has an electron-transporting layer having ionization potential of 5.9 eV or more.

A method of forming an organic layer of the luminescent device containing the metal complex of the present invention is not particularly limited. As the method, various methods, such as a resistance heating vapor deposition method, an electron-beam method, a sputtering method, a molecular lamination method, a coating method (e.g., a spray coating method, dip coating method, dipping method, roll coating method, gravure coating method, reverse coating method, roll brushing method, air knife coating method, curtain coating method, spin coating method, flow coating method, bar coating method, micro gravure coating method, air doctor coating method, blade coating method, squeeze coating method, transfer roll coating method, kiss coating method, cast coating method, extrusion coating method, wire bar coating method and screen coating method), an inkjet method, a printing method, and a transfer method, can be adopted. From the viewpoints of characteristics and production, a resistance heating vapor deposition method, a coating method and a transfer method are preferable.

The positive electrode is to supply positive holes to a positive hole-injecting layer, a positive hole-transporting layer, a luminescent layer, and the like; and metals, alloys, metal oxides, electrically conductive compounds, or mixtures of these can be used therefor, and materials having a work function of 4 eV or more are preferably used. Specific examples of the materials include electrically conductive metal oxides, such as tin oxide, zinc oxide, indium oxide, and indium tin oxide (ITO); metals, such as gold, silver, chromium, and nickel; mixtures or laminations of these metals with electrically conductive metal oxides; inorganic electrically conductive substances, such as copper iodide and copper sulfide; organic electrically conductive substances, such as polyaniline, polythiophene, and polypyrrole; and laminations of these materials with ITO. Electrically conductive metal oxides are preferably used, and ITO is particularly preferably used in view of producibility, high conductivity and transparency. The film thickness of the positive electrode can be selected arbitrarily according to materials to be used, but is generally preferably from 10 nm to 5 μm, more preferably from 50 nm to 1 μm, and still more preferably from 100 nm to 500 nm.

The positive electrode generally comprises a layer(s) formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently maintain mechanical strength. When glass is used, the thickness is generally 0.2 mm or more, preferably 0.7 mm or more.

Various processes are used in the manufacture of the positive electrode according to the materials to be used. In the case of using ITO, for example, a thin layer film(s) is formed by an electron beam process, a sputtering process, a resistance heating vapor deposition process, a chemical reaction process (e.g. a sol-gel process), or the process of coating a dispersion of an indium tin oxide.

It is possible to reduce the driving voltage or increase the luminescent efficacy of the device or element, by a process such as washing of the positive electrode. In the case of using ITO, for example, UV-ozone processing or plasma treatment is effective.

The negative electrode is to supply electrons to an electron-injecting layer, an electron-transporting layer, a luminescent layer, and the like, and the negative electrode is selected taking into consideration the adhesion with the layer adjacent to the negative electrode, such as an electron-injecting layer, electron-transporting layer, or luminescent layer; ionization potential, stability, and the like. As materials of the negative electrode, metals, alloys, metal halides, metal oxides, electrically conductive compounds, or mixtures of these materials can be used. Specific examples include alkali metals (e.g., Li, Na, K) or their fluorides or oxides, alkaline earth metals (e.g., Mg, Ca) or their fluorides or oxides, gold, silver, lead, aluminum, sodium-potassium alloys or mixed metals thereof, lithium-aluminum alloys or mixed metals thereof, magnesium-silver alloys or mixed metals thereof, and rare earth metals, such as indium, ytterbium, and the like; preferably materials having a work function of 4 eV or less, and more preferably aluminum, lithium-aluminum alloys or mixed metals thereof, and magnesium-silver alloys or mixed metals thereof. The negative electrode structure may be not only a single layer of the aforementioned compound or mixture thereof, but also a laminate comprised of the aforementioned compound or mixture thereof. For example, laminate structures of aluminum/lithium fluoride, or aluminum/lithium oxide are preferable. The film thickness of the negative electrode can be selected arbitrarily according to materials to be used, but is generally preferably from 10 nm to 5 μm, more preferably from 50 nm to 1 μm, and still more preferably from 100 nm to 1 μm.

Processes such as an electron beam process, a sputtering process, a resistance heating vapor deposition process, a coating process, and a transfer method are used in the manufacture of the negative electrode, and a single metal can be vapor-deposited or two or more components can be vapor-deposited at the same time. Further, a plurality of metals can be vapor-deposited at the same time to form an alloy electrode, alternatively a previously prepared alloy can be vapor-deposited.

It is preferred that the sheet resistance of the positive electrode and the negative electrode be low, preferably several hundreds Ω/□ or less.

The material for a luminescent layer may be any of materials capable of forming a layer that can function so as to accept both injection of holes from the positive electrode, the hole injection layer or the hole-transporting layer and injection of electrons from the negative electrode, the electron injection layer or the electron-transporting layer when electric field is applied thereto, or to let the charges injected therein to transfer, or to enable the emission of light by providing a cite for recombining the holes and the electrons. Besides the compound of the present invention, examples of the material include various metal complexes typically exemplified by metal complex or rare earth complex of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, and 8-quinolinol derivatives; polymeric compounds, such as polythiophene, polyphenylene, and polyphenylenevinylene; organic silanes; transition metal complexes (e.g., iridium trisphenylpyridine and platinum porphyrin, and derivatives thereof).

As the host material of the luminescent layer, there are preferably illustrated amine compounds (for example, triarylamine compounds); metal chelate oxynoid compounds (compounds having a metal-oxygen bond) in which the metal is aluminum, zinc or transition metals, and a ligand is 8-hydroxyquinoline derivatives, 2-(2-pyridino)phenol derivatives or the like; polyarylene compounds (for example, hexaphenyl benzene derivatives), condensed aromatic carbocyclic compounds and non-complex aromatic nitrogen-containing heterocyclic compounds (for example, carbazole derivatives). The host material of the luminescent layer may be a mixture of at least two compounds.

The film thickness of the luminescent layer is not particularly restricted, but it is generally preferably from 1 nm to 5 µm, more preferably from 5 nm to 1 µm, and still more preferably from 10 nm to 500 nm.

Although there is no particular limitation on methods for forming the luminescent (light emitting) layers, methods such as resistance heating vapor deposition, electron beam processing, sputtering, molecular lamination, coating, inkjet process, printing, LB (Langmuir-Blodgett) processing, and transfer process can be used. Preferred are a resistance heating vapor deposition method and a coating method.

The luminescent layer may be formed of a single compound, or two or more kinds of compounds. Further, the luminescent layer may have a single layer structure, or a multiple-layer structure made of at least two layers. Each layer may emit light of a different luminescent color so that the luminescent layer can emit, for example, a white light. A single luminescent layer may emit a white light. When the luminescent layer is a plurality of layers, each layer may be formed of a single material, or at least two compounds or materials.

Materials of the positive hole-injecting layer and the positive hole-transporting layer are sufficient if they have any of the functions of injecting positive holes from the positive electrode, transporting positive holes, and blocking the electrons injected from the negative electrode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-series compounds, porphyrin-series compounds, polysilane-series compounds, poly(N-vinylcarbazole) derivatives, aniline-series copolymers, electrically conductive high molecular weight oligomers, such as thiophene oligomers and polythiophene; organic silane compounds, carbon film, and the compounds of the present invention. The film thickness of the hole-injection layer is not particularly limited, and in general, it is preferably from 1 nm to 5 µm, more preferably from 5 nm to 1 µm, and further preferably from 10 nm to 500 nm. The film thickness of the hole-transporting layer is not particularly limited, and in general, it is preferably from 1 nm to 5 µm, more preferably from 5 nm to 1 µm, and further preferably from 10 nm to 500 nm. The hole-injecting layer or hole-transporting layer may have a single layer structure of one kind or two or more kinds of the above materials, or alternatively, a multilayer structure comprising plural layers having the same composition or different compositions.

As the materials for the hole-injunction layer, copper phthalocyanine and star burst-type amine compounds are preferable.

Examples of a method of forming the hole-injecting layer and the hole-transporting layer include a vacuum deposition method, an LB method, the process of dissolving or dispersing the above-described hole-injecting/transporting material in a solvent and coating; an ink jet method, a printing method, and a transfer method. In the case of a coating process, a positive hole-injecting/transporting material can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, and the like.

Materials of the electron-injecting layer and the electron-transporting layer are sufficient if they have any of the functions of injecting electrons from the negative electrode, transporting electrons, and blocking (as a barrier off) the positive holes injected from the positive electrode. As the materials for the electron-transporting layer, metal chelate oxynoid compounds, polyarylene compounds, condensed aromatic carbocyclic compounds and non-complex aromatic heterocyclic compounds are preferable. Specific examples of the materials include triazole derivatives, oxazole derivatives, oxadiazole derivatives, imidazole derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, tetracarboxylic acid anhydrides of aromatic rings such as naphthalene and perylene, phthalocyanine derivatives, various metal complexes represented by metal complexes of 8-quinolinol derivatives, metallophthalocyanines and metal complexes having benzoxazole or benzothiazole ligands, organosilane compounds. The film thickness of the electron-injecting layer and the electron-transporting layer is not particularly restricted, but it is generally preferably from 1 nm to 5 µm, more preferably from 5 nm to 1 µm, and still more preferably from 10 nm to 500 nm. The electron-injecting layer and the electron-transporting layer may be single layer structure comprising one or two or more of the above materials, or may be multilayer structure comprising a plurality of layers of the same composition or different compositions.

Examples of a method of forming the electron injecting layer and the electron transporting layer include a vacuum deposition method, an LB method, the process of dissolving or dispersing the above-described electron-injecting/transporting material in a solvent and coating; an ink jet method, a printing method, and a transfer method. In the case of a coating process, an electron injecting/transporting material can be dissolved or dispersed with a resin component. As the resin components, for example, those exemplified in the positive hole-injecting and transporting layers can be applied.

Materials of the protective layer are sufficient if they have the function of preventing substances which accelerate deterioration of the device or element, such as water or oxygen, from entering the device or element. Specific examples of the materials include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$, and $TiO_2$; metal fluorides such as $MgF_2$, LiF, $AlF_3$, and $CaF_2$; metal nitrides such as $SiN_x$ and $SiO_xN_y$; polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers prepared by copolymerizing a monomer mixture of tetrafluoroethylene and at least one comonomer, fluorine-containing copolymers having cyclic structures on the main chain, water-absorbing substances having a water absorption rate of at least 1%, and moisture-proof substances having a water absorption rate of at most 0.1%.

The forming process of the protective layer is also not particularly restricted, and, for example, a vacuum deposi-

EXAMPLES

The present invention will be explained in more detail with reference to the examples below, but the embodiments for carrying out the present invention should not be construed to be limited to these.

Synthesis of Compound (1)

To 6,6'-bis(2-hydroxyphenyl)-2,2'-bipyridyl (0.1 g) and $PtCl_2$ (0.16 g), benzonitrile (10 ml) was added and heated under reflux for 3 hours under a nitrogen atmosphere. After cooling the reaction solution to a room temperature, methanol was added to the reaction solution to cause precipitation, and the precipitate was suction filtered. The solid obtained was purified using silica gel chromatography (chloroform as a developing solvent), to obtain 0.06 g of Compound (1). The structure of Compound (1) was identified by mass spectrometry. Upon irradiation of UV light to a chloroform solution containing Compound (1) under a nitrogen atmosphere, reddish orange-colored light-emission ($\lambda_{max}$=624 nm) was obtained.

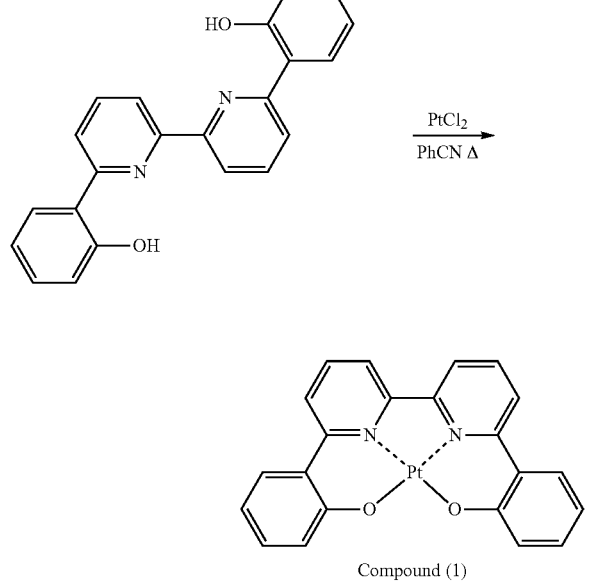

Compound (1)

6,6'-bis(2-hydroxyphenyl)-2,2'-bipyridyl used as a starting material in the aforementioned reaction, can be synthesized according to the method described in Journal of Organic Chemistry, 741, 11 (1946). Alternatively, the compound can be synthesized according to the scheme described below.

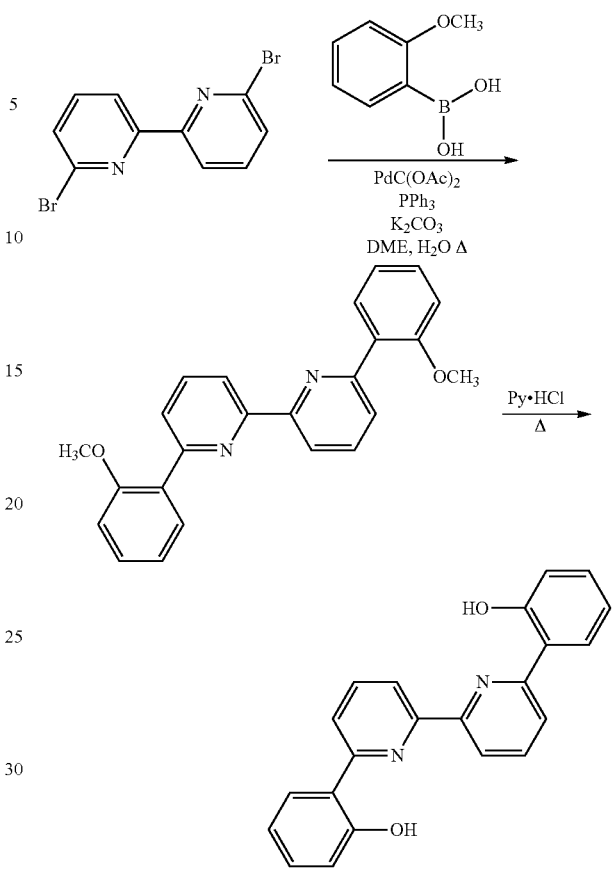

Synthesis of 6,6'-bis(2-methoxyphenyl)-2,2'-bipyridyl

To a mixture of 6,6'-dibromo-2,2'-bipyridyl (1.15 g), 2-methoxyphenyl boronic acid (1.45 g), $PPh_3$ (0.167 g), potassium carbonate (2.2 g) and $Pd(OAc)_2$ (36 mg), dimethoxyethane (10 ml) and water (10 ml) were added and heated under reflux for 4 hours under a nitrogen atmosphere. After cooling the reaction solution to a room temperature, chloroform (20 ml) and water (20 ml) were added to the reaction solution for separation. Thereafter, the organic layer was concentrated. Purification by silica gel chromatography (chloroform as a developing solvent) was carried out, to obtain 0.9 g of 6,6'-bis(2-methoxyphenyl)-2,2'-bipyridyl.

Synthesis of 6,6'-bis(2-hydroxyphenyl)-2,2'-bipyridyl

A mixture of a 6,6'-bis(2-methoxyphenyl)-2,2'-bipyridyl ligand (0.3 g) and pyridine hydrochloride (10 g) was heated for 4 hours at 160° C. under a nitrogen atmosphere. After cooling the reaction solution to a room temperature, chloroform (20 ml) and water (20 ml) were added to the reaction solution for separation. Thereafter, the organic layer was concentrated. Purification by silica gel chromatography (chloroform as a developing solvent) was carried out, to obtain 0.2 g of 6,6'-bis(2-hydroxyphenyl)-2,2'-bipyridyl.

Synthesis schemes of compound (79) and compound (88) that were synthesized according to the same method as mentioned above are shown below.

Synthesis scheme-1

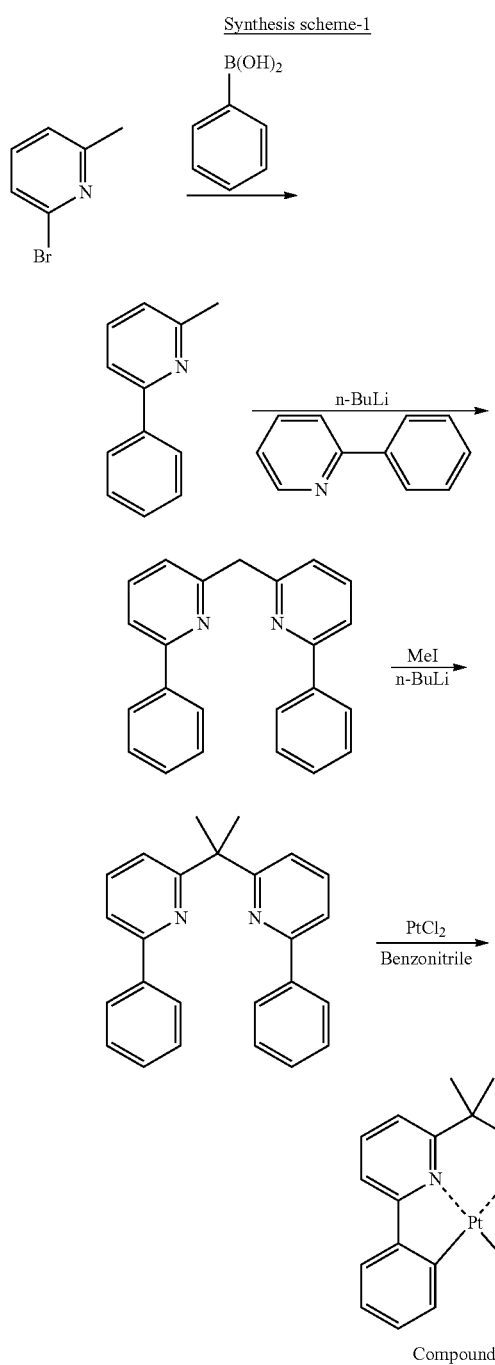

Compound (79)

Synthesis scheme-2

-continued

Compound (88)

$\lambda_{max}$ of light emitted from Compound (79) in dichloroethane was 512 nm, while $\lambda_{max}$ of light emitted from Compound (88) in dichloroethane was 620 nm.

The compounds represented by formula (11) or (12) in which the substituents each are an alkyl group, an aryl group, a heteroaryl group, or a halogen atom, can be also synthesized according to the aforementioned method.

Comparative Example 1

A cleaned ITO substrate was placed in a vacuum evaporator, and onto the substrate TPD (N,N-diphenyl-N,N-di(m-tolyl)benzidine) was evaporated to form a film having a thickness of 50 nm, then PtOEP (octaethyl porphyrin platinum complex) and Compound A (a ratio by mass of 1:17) were co-evaporated to form a film having a thickness of 36 nm, and then Compound A was evaporated to form a film having a thickness of 36 nm. Then, a patterned mask (for adjusting each emission area to 4 mm×5 mm) was set on the organic thin layers, and further thereon, inside the vacuum evaporator, lithium fluoride was evaporated to form a film having a thickness of 3 nm, followed by deposition of a 400 nm-thick aluminum.

The thus produced EL device was subjected to luminescence by applying thereto a DC constant voltage by means of a source measure unit, Model 2400 (trade name), made by Toyo Technica Co., Ltd. and the luminance that the EL device showed was measured using a luminometer BM-8 (trade name), made by Topcon Co. As a result of the measurement, the light emission that the EL device gave was found to be a luminescence of 200 cd/m² with external quantum efficiency of 1.1% and the maximum luminance of 390 cd/m².

Example 1

A cleaned ITO substrate was placed in a vacuum evaporator, and onto the substrate TPD (N,N-diphenyl-N,N-di(m-tolyl)benzidine) was evaporated to form a film having a thickness of 50 nm, then Compound (1) according to the present invention and Compound A (a ratio by mass of 1:17) were co-evaporated to form a film having a thickness of 36 nm, and then Compound B was evaporated to form a film having a thickness of 36 nm. Then, a patterned mask (for adjusting each emission area to 4 mm×5 mm) was set on the organic thin layers, and further thereon, inside the vacuum evaporator, lithium fluoride was evaporated to form a film having a thickness of 3 nm, followed by deposition of a 400 nm-thick aluminum film.

The thus produced EL device was subjected to luminescence by applying thereto a DC constant voltage by means of a source measure unit, Model 2400 (trade name), made by Toyo Technica Co., Ltd. and the luminance that the EL device showed was measured using a luminometer BM-8

(trade name), made by Topcon Co. As a result of the measurement, the light emission that the EL device gave was found to be a luminescence of 200 cd/m² with external quantum efficiency of 2.8% and the maximum luminance of 1090 cd/m².

Example 2

A cleaned ITO substrate was placed in a vacuum evaporator, and onto the substrate TPD (N,N-diphenyl-N,N-di(m-tolyl)benzidine) was evaporated to form a film having a thickness of 50 nm, then Compound (1) according to the present invention and Compound A (a ratio by mass of 1:2) were co-evaporated to form a film having a thickness of 36 nm, and then Compound B was evaporated to form a film having a thickness of 36 nm in this order. Then, a patterned mask (for adjusting each emission area to 4 mm×5 mm) was set on the organic thin layers, and further thereon, inside the vacuum evaporator, lithium fluoride was evaporated to form a film having a thickness of 3 nm, followed by deposition of a 400 nm-thick aluminum film.

The thus produced EL device was subjected to luminescence by applying thereto a DC constant voltage by means of a source measure unit, Model 2400 (trade name), made by Toyo Technica Co., Ltd. and the luminance that the EL device showed was measured using a luminometer BM-8 (trade name), made by Topcon Co. As a result of the measurement, the light emission that the EL device gave was found to be a luminescence of 200 cd/m² with external quantum efficiency of 4.4% and the maximum luminance of 3820 cd/m².

Comparative Example 2

An EL device (Device No-101) was prepared according to the method described in Example 8 of U.S. Pat. No. 6,653,654 B1.

Comparative Example 3

A cleaned ITO substrate was placed in a vacuum evaporator, and onto the substrate α-NPD was evaporated to form a hole-transporting layer having a thickness of 50 nm. Then Bepp$_2$ as a host and Compound (65) as a luminescent material were co-evaporated for 0.4 nm/sec and 0.02 nm/sec respectively so as to become 40 nm in film thickness, thereby to form a luminescent layer. Then, a patterned mask (for adjusting each emission area to 2 mm×2 mm) was set on the organic thin layers, and further thereon, inside the vacuum evaporator, lithium fluoride was evaporated to form a film having a thickness of 1.5 nm, followed by deposition of a 200 nm-thick aluminum film. Subsequently, the device was sealed after incorporation of a drying agent therein, to prepare an EL device (Device No-102). In addition, another EL device (Device No-103) was prepared in the same manner as described above, except that the luminescent material was replaced with Compound (1).

Example 3

A luminescent layer was formed in the same manner as in Comparative Example 3, except for changing the film thickness of host to 36 nm. Thereon, compound B was evaporated to form an electron-transporting layer having a thickness of 36 nm. Then, a patterned mask (for adjusting each emission area to 2 mm×2 mm) was set on the organic thin layers, and further thereon, inside the vacuum evaporator, lithium fluoride was evaporated to form a film having a thickness of 5 nm, followed by deposition of a 500 nm-thick aluminum film. Subsequently, the device was sealed after incorporation of a drying agent therein, to prepare an EL device (Device No-104). In addition, another EL device (Device No-105) was prepared in the same manner as described above, except that the host material was replaced with Compound A.

Example 4

A cleaned ITO substrate was placed in a vacuum evaporator, and onto the substrate copper phthalocyanine was evaporated to form a film having a thickness of 10 nm, and thereon α-NPD was evaporated to be a thickness of 20 nm thereby to form a hole-transporting layer. Thereon, Compound A as a host and Compound (1) as a luminescent material were co-evaporated for 0.4 nm/sec and 0.02 nm/sec respectively so as to become 30 nm in film thickness, thereby to form a luminescent layer. On the luminescent layer, BAlq was evaporated to form a hole-blocking layer having a thickness of 10 nm, and then Alq was evaporated to form an electron-transporting layer having a thickness of 40 nm. Then, a patterned mask (for adjusting each emission area to 2 mm×2 mm) was set on the organic thin layers, and further thereon, inside the vacuum evaporator, lithium fluoride was evaporated to form a film having a thickness of 5 nm, followed by deposition of a 500 nm-thick aluminum film. Subsequently, the device was sealed after incorporation of a drying agent therein, to prepare an EL device (Device No-201). In addition, other EL devices (Device No-202 to 206) were prepared in the same manner as described above, except for changing the host material as shown in Table 2.

Compound A

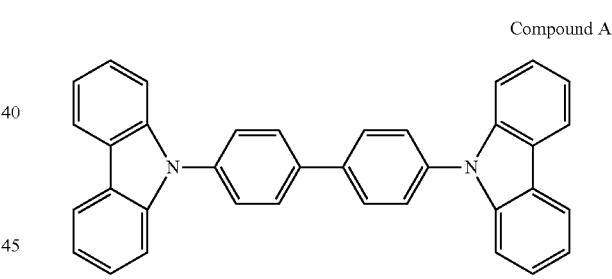

Compound B

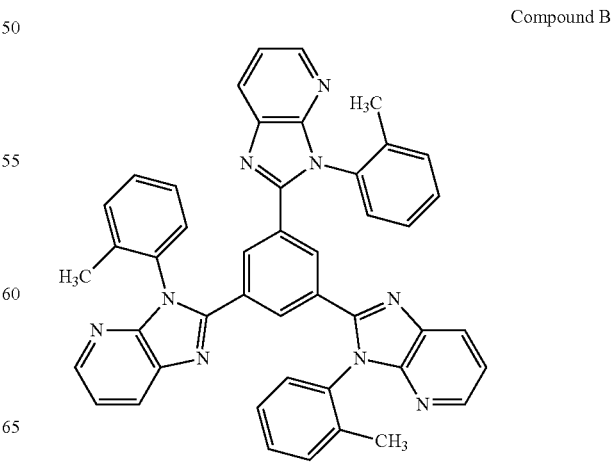

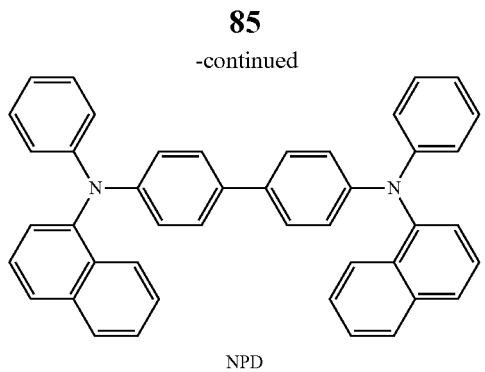

NPD

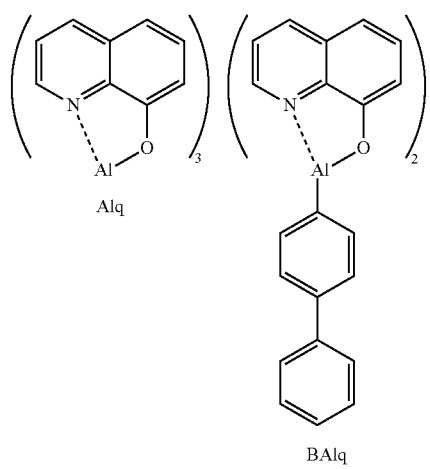

Alq   BAlq

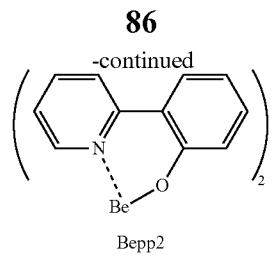

Bepp2

Next, each EL device thus produced was evaluated as shown below:

The EL devices of the present invention and of comparison were subjected to luminescence by applying thereto a DC constant voltage by means of a source measure unit, Model 2400 (trade name), made by Toyo Technica Co., Ltd. and the luminance that each EL device showed was measured using a luminometer BM-8 (trade name), made by Topcon Co. and emission wavelength was measured using a spectrum analyzer PMA-11 (trade name), made by Hamamatsu Photonics KK, to obtain luminous efficiency. Next, durability was evaluated as follows: First, the device was driven at the rate of 1 mA/4 mm$^2$, and the initial luminance was measured. Then, after 200 h low-current driving of the device at the rate of 1 mA/4 mm$^2$, luminance was measured. The maintenance rate of luminance was obtained by comparing the 200 h luminance with the initial luminance. The results are shown in Tables 1 and 2.

TABLE 1

| Element Nos. | Luminescent material (Dope concentration) | Host material (Film thickness) | Electron-transporting layer (Film thickness) | Maintenance rate of luminance | Remarks |
| --- | --- | --- | --- | --- | --- |
| 101 | Compound (65) 2% | Bepp$_2$ (40 nm) | — | 6% | Comparative example (The element described in U.S. Pat. No. 6,653,564 B1) |
| 102 | Compound (65) 5% | Bepp$_2$ (40 nm) | — | 11% | Comparative example (The element described in U.S. Pat. No. 6,653,564 B1) |
| 103 | Compound (1) 5% | Bepp$_2$ (40 nm) | — | 8% | Comparative example (The element described in U.S. Pat. No. 6,653,564 B1) |
| 104 | Compound (1) 5% | Bepp$_2$ (36 nm) | Compound B (36 nm) | 21% | This invention |
| 105 | Compound (1) 5% | Compound A (36 nm) | Compound B (36 nm) | 32% | This invention |

Element configuration: ITO/NPD (50 nm)/5 wt % Luminescent material-Host material/Electron-transporting material/LiF—Al The results demonstrate that the devices of the present invention, containing an electron-transporting layer, exhibited an enhanced maintenance rate of luminance that led to excellent durability of the device, compared with the devices of the Comparative Examples. In addition, the durability of the device was further improved by altering the host material to a non-complex aromatic heterocyclic compound such as Compound A.

TABLE 2

| Element Nos. | Luminescent material | Host material | Light Emission $\lambda_{max}$ | Maintenance rate of luminance | Remarks |
|---|---|---|---|---|---|
| 201 | Compound (1) | Compound A | 615 nm | 81% | This invention |
| 202 | Compound (15) | Compound A | 586 nm | 88% | This invention |
| 204 | Compound (79) | Compound A | 509 nm | 83% | This invention |
| 205 | Compound (88) | Compound A | 620 nm | 79% | This invention |
| 206 | Compound (15) | BAlq | 585 nm | 92% | This invention |

Element configuration: ITO/CuPc(10 nm)/NPD(20 nm)/5 wt % Luminescent material-Host material (30 nm)/BAlq (10 nm)/Alq (40 nm)/LiF—Al Further, the results demonstrate that the use of both copper phthalocyanine (CuPc), acting as a hole-injunction layer, and BAlq, acting as a hole-blocking layer, further improved on the durability of the device, and the compounds of the present invention enabled emitting red light and green light with excellent color purity. Further, the compounds of the present invention also enable emitting light of a shorter wavelength.

INDUSTRIAL APPLICABILITY

The luminescent devices of the present invention are high in both external quantum efficiency and maximum luminance, and excellent in luminescent characteristics (performances). Further, the luminescent devices are excellent in durability. The luminescent device of the present invention can be preferably used in such fields as display devices, displays, backlights, electrophotography, illuminating light sources, recording light sources, exposing light sources, reading light sources, signs, signboards, interiors, and optical communications. Further, the compounds of the present invention can be utilized for the electroluminescent devices, as well as medical usage, brightening agents, photographic materials, UV absorbing materials, laser dyes, recording media materials, inkjet pigments, color filter dyes, color conversion filters, and the like. The novel complexes of the present invention are suitable for producing such excellent luminescent devices as described above.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. An organic electroluminescent device, comprising:
a pair of electrodes and at least one organic layer including a luminescent layer between the pair of electrodes,
wherein at least one layer between the pair of electrodes comprises at least one metal complex represented by formula (6) having a tetradentate or higher polydentate chain structure ligand:

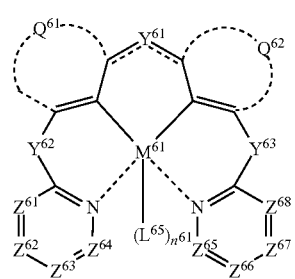

Formula (6)

wherein $M^{61}$ represents a metal ion;
$Q^{61}$ and $Q^{62}$ each represent a group to form a ring;
the ring formed by $Q^{61}$ or $Q^{62}$ may bond to $Z^{61}$ or $Z^{68}$ respectively via a linking bond, to form a ring;
$Y^{61}$ represents a linking group, a single bond or a double bond;
$Y^{62}$ and $Y^{63}$ each represent a linking group or a single bond;
$L^{65}$ represents a ligand to coordinate to $M^{61}$;
$Z^{61}$, $Z^{62}$, $Z^{63}$, $Z^{64}$, $Z^{65}$, $Z^{66}$, $Z^{67}$, and $Z^{68}$ each represent a substituted or unsubstituted carbon atom or a nitrogen atom;
$Z^{61}$ and $Z^{62}$, $Z^{62}$ and $Z^{63}$, $Z^{63}$ and $Z^{64}$, $Z^{65}$ and $Z^{66}$, $Z^{66}$ and $Z^{67}$, $Z^{67}$ and $Z^{68}$ each may bond to each other via a linking group, to form a condensed ring; and
$n^{61}$ represents 0 to 4.

2. The organic electroluminescent device of claim 1, wherein in the complex represented by formula (6), at least one ring formed with $Q^{61}$ or $Q^{62}$ is a benzene ring, a pyridine ring, a thiophene ring, a thiazole ring, or a condensed ring thereof.

3. The organic electroluminescent device of claim 1, wherein in the complex represented by formula (6), $Y^{62}$ and $Y^{63}$ each independently represent a single bond, a carbonyl-linking group, an alkylene linking group, or an alkenylene group.

4. The organic electroluminescent device of claim 1, wherein in the complex represented by formula (6), $Y^{61}$ is a single bond or an alkylene group.

5. The organic electroluminescent device of claim 1, wherein the organic layer comprises at least one luminescent layer and a hole transporting layer, and the organic layer further comprises at least one layer selected from the group consisting of an exciton-blocking layer, a hole injection layer, a hole-blocking layer and an electron-transporting layer.

6. The organic electroluminescent device of claim 1, wherein the organic layer comprises at least one luminescent layer, and a host material of the luminescent layer is selected from the group consisting of an amine compound, a metal chelate oxynoid compound in which the metal is aluminum, zinc or a transition metal, a polyarylene compound, a condensed aromatic carbocyclic compound, and a non-complex aromatic heterocyclic compound.

7. The organic electroluminescent device of claim 1, wherein the organic layer comprises at least one electron-transporting layer in which an electron-transporting material is selected from the group consisting of a metal chelate oxynoid compound, a polyarylene compound, a condensed aromatic carbocyclic compound, and a non-complex aromatic heterocyclic compound.

8. An organic electroluminescent device, comprising:
a pair of electrodes and at least one organic layer including a luminescent layer between the pair of electrodes, wherein at least one layer between the pair of electrodes comprises at least one metal complex represented by formula (7) having a tetradentate or higher polydentate chain structure ligand:

Formula (7)

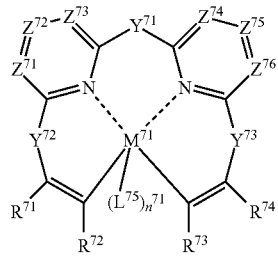

Formula (7)

wherein $M^{71}$ represents a metal ion;
$Y^{71}$, $Y^{72}$, and $Y^{73}$ each represent a linking group or a single bond;
$L^{75}$ represents a ligand to coordinate to $M^{71}$;
$Z^{71}$, $Z^{72}$, $Z^{73}$, $Z^{74}$, $Z^{75}$, and $Z^{76}$ each represent a substituted or unsubstituted carbon atom or a nitrogen atom;
$Z^{71}$ and $Z^{72}$, and $Z^{73}$ and $Z^{74}$ each may bond to each other via a linking group to form a condensed ring;
$R^{71}$, $R^{72}$, $R^{73}$, and $R^{74}$ each represent a hydrogen atom or a substituent; and
$n^{71}$ represents 0 to 4.

9. The organic electroluminescent device of claim 8, wherein in the complex represented by formula (7), $R^{71}$, $R^{72}$, $R^{73}$, and $R^{74}$ are each an alkyl group, an aryl group, or a group that forms a condensed ring by forming a bond between $R^{71}$ and $R^{72}$, or between $R^{73}$ and $R^{74}$.

10. The organic electroluminescent device of claim 8, wherein in the complex represented by formula (7), $Y^{72}$ and $Y^{73}$ each independently represent a single bond, a carbonyl-linking group, an alkylene linking group, or an alkenylene group.

11. The organic electroluminescent device of claim 8, wherein in the complex represented by formula (7), $Y^{71}$ is a single bond or an alkylene group.

12. The organic electroluminescent device of claim 8, wherein the organic layer comprises at least one luminescent layer and a hole transporting layer, and the organic layer further comprises at least one layer selected from the group consisting of an exciton-blocking layer, a hole injection layer, a hole-blocking layer and an electron-transporting layer.

13. The organic electroluminescent device of claim 8, wherein the organic layer comprises at least one luminescent layer, and a host material of the luminescent layer is selected from the group consisting of an amine compound, a metal chelate oxynoid compound in which the metal is aluminum, zinc or a transition metal, a polyarylene compound, a condensed aromatic carbocyclic compound, and a non-complex aromatic heterocyclic compound.

14. The organic electroluminescent device of claim 8, wherein the organic layer comprises at least one electron-transporting layer in which an electron-transporting material is selected from the group consisting of a metal chelate oxynoid compound, a polyarylene compound, a condensed aromatic carbocyclic compound, and a non-complex aromatic heterocyclic compound.

15. The organic electroluminescent device of claim 8, wherein the organic layer comprises at least one luminescent layer, and a host material of the luminescent layer is composed of at least two compounds.

16. A metal complex represented by formula (6) having a tetradentate or higher polydentate chain structure ligand:

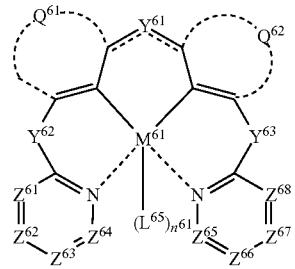

Formula (6)

wherein $M^{61}$ represents a metal ion;
$Q^{61}$ and $Q^{62}$ each represent a group to form a ring;
the ring formed by $Q^{61}$ or $Q^{62}$ may bond to $Z^{61}$ or $Z^{68}$ respectively via a linking bond, to form a ring;
$Y^{61}$ represents a linking group, a single bond or a double bond;
$Y^{62}$ and $Y^{63}$ each represent a linking group or a single bond;
$L^{65}$ represents a ligand to coordinate to $M^{61}$;
$Z^{61}$, $Z^{62}$, $Z^{63}$, $Z^{64}$, $Z^{65}$, $Z^{66}$, $Z^{67}$, and $Z^{68}$ each represent a substituted or unsubstituted carbon atom or a nitrogen atom;
$Z^{61}$ and $Z^{62}$, $Z^{62}$ and $Z^{63}$, $Z^{63}$ and $Z^{64}$, $Z^{65}$ and $Z^{66}$, $Z^{66}$ and $Z^{67}$, $Z^{67}$ and $Z^{68}$ each may bond to each other via a linking group, to form a condensed ring; and
$n^{61}$ represents 0 to 4.

17. The metal complex of claim 16, wherein in the complex represented by formula (6), at least one ring formed with $Q^{61}$ or $Q^{62}$ is a benzene ring, a pyridine ring, a thiophene ring, a thiazole ring, or a condensed ring thereof.

18. The metal complex of claim 16, wherein in the complex represented by formula (6), $Y^{62}$ and $Y^{63}$ each independently represent a single bond, a carbonyl-linking group, an alkylene linking group, or an alkenylene group.

19. The metal complex of claim 16, wherein in the complex represented by formula (6), $Y^{61}$ is a single bond or an alkylene group.

20. A metal complex represented by formula (7):

Formula (7) having a tetradentate or higher polydentate chain structure ligand:

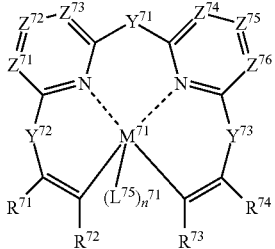

Formula (7)

wherein $M^{71}$ represents a metal ion;

$Y^{71}$, $Y^{72}$, and $Y^{73}$ each represent a linking group or a single bond;

$L^{75}$ represents a ligand to coordinate to $M^{71}$;

$Z^{71}$, $Z^{72}$, $Z^{73}$, $Z^{74}$, $Z^{75}$, and $Z^{76}$ each represent a substituted or unsubstituted carbon atom or a nitrogen atom;

$Z^{71}$ and $Z^{72}$, and $Z^{73}$ and $Z^{74}$ each may bond to each other via a linking group to form a condensed ring;

$R^{71}$, $R^{72}$, $R^{73}$, and $R^{74}$ each represent a hydrogen atom or a substituent; and $n^{71}$ represents 0 to 4.

21. The metal complex of claim 20, wherein in the complex represented by formula (7), $R^{71}$, $R^{72}$, $R^{73}$, and $R^{74}$ are each an alkyl group, an aryl group, or a group that forms a condensed ring by forming a bond between $R^{71}$ and $R^{72}$, or between $R^{73}$ and $R^{74}$.

22. The metal complex of claim 20, wherein in the complex represented by formula (7), $Y^{72}$ and $Y^{73}$ each independently represent a single bond, a carbonyl-linking group, an alkylene linking group, or an alkenylene group.

23. The metal complex of claim 20, wherein in the complex represented by formula (7), $Y^{71}$ is a single bond or an alkylene group.

* * * * *